(12) United States Patent
Yamanaka et al.
::::

(10) Patent No.: US 12,012,615 B2
(45) Date of Patent: *Jun. 18, 2024

(54) METHOD OF MAKING INDUCED PLURIPOTENT STEM CELLS USING P53 INHIBITORS

(71) Applicant: Kyoto University, Kyoto (JP)

(72) Inventors: Shinya Yamanaka, Kyoto (JP); Kazutoshi Takahashi, Kyoto (JP); Keisuke Okita, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,054

(22) Filed: Nov. 19, 2018

(65) Prior Publication Data

US 2019/0309263 A1 Oct. 10, 2019

Related U.S. Application Data

(60) Continuation of application No. 13/942,208, filed on Jul. 15, 2013, now abandoned, which is a division of application No. 12/672,042, filed as application No. PCT/JP2009/062173 on Jun. 26, 2009, now Pat. No. 8,530,238.

(60) Provisional application No. 61/209,686, filed on Mar. 10, 2009, provisional application No. 61/200,307, filed on Nov. 25, 2008, provisional application No. 61/194,700, filed on Sep. 30, 2008, provisional application No. 61/095,573, filed on Sep. 9, 2008, provisional application No. 61/076,487, filed on Jun. 27, 2008.

(51) Int. Cl.
| | |
|---|---|
| *C12N 5/00* | (2006.01) |
| *C12N 5/074* | (2010.01) |
| *C12N 15/85* | (2006.01) |

(52) U.S. Cl.
CPC ........... *C12N 5/0696* (2013.01); *C12N 15/85* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/11* (2013.01); *C12N 2510/00* (2013.01)

(58) Field of Classification Search
USPC .................................................. 435/325, 455
See application file for complete search history.

(56) References Cited

U.S. PATENT DOCUMENTS

| | | | | |
|---|---|---|---|---|
| 7,695,426 | B2 * | 4/2010 | O'Neill | A61K 31/4188 600/33 |
| 8,530,238 | B2 * | 9/2013 | Yamanaka | A61P 43/00 435/455 |
| 8,900,871 | B2 | 12/2014 | Okita et al. | |
| 2007/0006223 | A1 | 1/2007 | Wetherly et al. | |
| 2007/0006332 | A1 * | 1/2007 | O'Neill | C07K 14/4746 800/14 |
| 2007/0202590 | A1 | 8/2007 | Shinohara et al. | |
| 2007/0254309 | A1 * | 11/2007 | O'Neill | G01N 33/689 435/7.2 |
| 2008/0233610 | A1 | 9/2008 | Thomson et al. | |
| 2009/0047263 | A1 | 2/2009 | Yamanaka et al. | |
| 2010/0093090 | A1 | 4/2010 | Deng et al. | |
| 2011/0223669 | A1 | 9/2011 | Yamanaka et al. | |
| 2012/0196360 | A1 | 8/2012 | Okita et al. | |

FOREIGN PATENT DOCUMENTS

| | | |
|---|---|---|
| CN | 101550406 A | 10/2009 |
| EP | 1970446 A1 * | 9/2008 |
| EP | 1970446 A1 | 9/2008 |
| WO | WO 2000/044364 * | 8/2000 |
| WO | WO 2000/044364 A3 | 8/2000 |
| WO | WO 2007/069666 A1 | 6/2007 |
| WO | WO 2009/157593 A1 | 12/2009 |

OTHER PUBLICATIONS

Walton (Mol. Cancer Therapy, 2005, vol. 4, No. 9, p. 1369-1377).*
Takahashi (Cell, 2006, vol. 126:663-676).*
Yu (Science, 2007, vol. 318, p. 1917-1920).*
Aoi (Science, Aug. 1, 2008, vol. 321, No. 5889, p. 699-702, available online Feb. 14, 2008).*
Nakagawa (Nat Biotechnol, Jan. 2008, vol. 26: 101-106).*
Feng (Cell Stem Cell, Apr. 3, 2009, vol. 4, p. 301-312).*
Gonzalez (PNAS, Jun. 2, 2009, vol. 106, No. 22, p. 8918-8922).*
Yamanaka (Nature, Jul. 2, 2009, vol. 460, No. 7251, p. 12759-12764).*
Hotta (J. Cell. Biochem., Sep. 2008, vol. 105, p. 940-948).*
Papapetrou (PNAS, Aug. 4, 2009, vol. 106, No. 31, p. 12759-12764).*
Strom (Nature Chem. Biol., 2006, vol. 2, p. 474-479).*
Mali (Stem Cells, May 2008, vol. 26, No. 8, p. 1998-2005).*
Dobbelstein (J. General Virol., 1998, vol. 79, p. 3079-3083).*
Bowman (Genes & Development, 1996, vol. 10, p. 826-835).*
Willis (Oncogene, 2004, vol. 23, p. 2330-2338).*
De Vries (PNAS, 2002, vol. 99, No. 5, p. 2948-2953).*
Aoi et al., *Science*, 321(5889): 699-702 (Aug. 1, 2008) [available on-line Feb. 14, 2008].
Blelloch et al., *Cell Stem Cell*, 1: 245-247 (2007).
Bowman et al., *Genes Dev.*, 10(7): 826-835 (1996).

(Continued)

*Primary Examiner* — Michael C Wilson
(74) *Attorney, Agent, or Firm* — Leydig, Voit & Mayer, Ltd.

(57) ABSTRACT

The invention provides an in vitro method of improving the efficiency of establishment of induced pluripotent stem (iPS) cells. The method comprises contacting an isolated somatic cell being reprogrammed into an iPS cell with an inhibitor of p53 function. The invention also provides an in vitro method of producing iPS cells. The method comprises bringing (a) nuclear reprogramming substances or nucleic acids encoding the nuclear reprogramming substances and (b) an inhibitor of p53 function into contact with a somatic cell.

4 Claims, 20 Drawing Sheets
(13 of 20 Drawing Sheet(s) Filed in Color)
Specification includes a Sequence Listing.

(56) References Cited

OTHER PUBLICATIONS

Brambrink et al., *Cell Stem Cell*, 2(2): 151-159 (Feb. 7, 2008).
Dobbelstein et al., *Journal of General Virology*, 79: 3079-3083 (1998).
Feng et al., *Cell Stem Cell*, 4: 301-312 (2009).
Gonzalez et al., *PNAS*, 106(22): 8918-8922 (2009).
Hanna et al., *Cell*, 133(2): 250-264 (Apr. 18, 2008).
He et al., *Biochem. Biophys. Res. Commun.*, 335: 676-683 (2005).
Hong et al., *Nature*, 460: 1132-1135 (Aug. 27, 2009).
Hotta et al., *J. Cell. Biochem.*, 105: 940-948 (2008).
Huangfu et al., *Nature Biotechnology*, 26(7): 795-797 (2008).
Inoue et al., *Curr. Biol.*, 15: 1114-1118 (2005).
Jin et al., *Exp. Mol. Med.*, 42: 574-582 (2010).
Kaji et al., *Nature*, 458: 771-775 (Apr. 9, 2009).
Kanatsu et al., *Cell*, 119: 1001-1012 (Dec. 29, 2004).
Kawamura et al., *Nature*, 460: 1140-1144 (Aug. 27, 2009).
Lee et al., *J. Cell Sci.*, 121: 1899-1906 (2008).
Mali et al., *Stem Cells*, 26(8): 1998-2005 (2008).
Marion et al., *Nature*, 460: 1149-1153 (Aug. 27, 2009).
Marson et al., *Cell Stem Cell*, 3: 132-135 (Aug. 7, 2008).
Meissner et al., *Nature Biotechnology*, 25: 1177-1181 (2007).
Mietz et al., *EMBO J.*, 11(13): 5013-5020 (1992).
Nakagawa et al., *Nature Biotechnology*, 26(1): 101-106 (Jan. 2008).
Okita et al., *Nature*, 448: 313-317 (Jul. 19, 2007).
Okita et al., *Science*, 322: 949-953 (Nov. 7, 2008).
Papapetrou et al., *PNAS*, 106(31): 12759-12764 (2009).
Park et al., *Nature*, 451: 141-146 (2008).
Qin et al., *The Journal of Biological Chemistry*, 282(8): 5842-5852 (2007).
Rao et al., *Advanced Drug Delivery Reviews*, 61: 746-759 (2009).
Ries et al., *Cell*, 103: 321-330 (2000).
Shi et al., *Cell Stem Cell*, 2: 525-528 (Jun. 2008).
Shi et al., *Cell Stem Cell*, 3: 568-574 (Nov. 6, 2008).
Silva et al., *PLoS Biology*, 6(10): 2237-2247 (Oct. 2008).
Takahashi et al., *Cell*, 126: 663-676 (Aug. 25, 2006).
Takahashi et al., *Cell*, 131: 861-872 (Nov. 30, 2007).
Walton et al., *Molecular Cancer Therapeutics*, 4: 1369-1377 (2005).
Willis et al., *Oncogene*, 23: 2330-2338 (2004).
Wernig et al., *Nature*, 448: 318-324 (Jul. 19, 2007).
Wernig et al., *Cell Stem Cell*, 2: 10-12 (2008).
Woltjen et al., *Nature*, 458: 766-770 (Apr. 9, 2009).
Xu et al., *Cancer Lett.*, 317: 33-40 (2012).
Yamanaka, Shinya, *Cell Stem Cell*, 1(1): 39-49 (Jul. 2007).
Yamanaka et al., *Nature*, 460(7251): 12759-12764 (2009).
Yu et al., *Science*, 318: 1917-1920 (Dec. 21, 2007).
Yu et al., *Science*, 324: 797-801 (May 8, 2009).
Zhao et al., *Cell Stem Cell*, 3(5): 475-479 (Nov. 6, 2008).
Zhao et al., *Journal of Cellular Biochemistry*, 105(4): 949-955 (Jul. 30, 2008).
Zdanov et al., *Ann. NY Acad. Sci.*, 1100: 316-322 (2007).
EMD Millipore, "Pifithrin-α, p-Nitro, Cyclic—CAS 60477-38-5—Calbiochem," Information for Catalog No. 506154 (2015) [downloaded from internet on Dec. 1, 2015 at http://www.merckmillipore.com/GB/en/product/Pifithrin-%CE%B1%2C-p-Nitro%2C-Cyclic---CAS-60477-38-5---Calbiochem,EMD_BIO-506154?bd=1].
Newspaper Article entitled "Improved Efficiency of Establishment of iPS Cells" in Hokkaido-Shinbun (afternoon paper), p. 4 (Mar. 17, 2009).
Newspaper Article entitled "Improved Efficiency of Establishment of iPS Cells" in Kahoku-Shinpo, p. 11 (Feb. 11, 2009).
European Patent Office, Extended European Search Report in European Patent Application No. 09770303.7 (dated Dec. 13, 2012).
Japanese Patent Office, Office Action in Japanese Patent Application No. 2010-506749 (dated Apr. 2, 2013).
Japanese Patent Office, International Search Report in International Patent Application No. PCT/JP2009/062173 (dated Oct. 6, 2009).
International Bureau of WIPO, International Search Report in International Patent Application No. PCT/JP2009/062173 (dated Jan. 5, 2011).
Intellectual Property Office of Singapore, Office Action in Singapore Patent Application No. 201000645-0 (dated Dec. 24, 2013).
Kareta et al., "Inhibition of Pluripotency Networks by the Rb Tumor Suppressor Restricts Reprogramming and Tumorigenesis," *Cell Stem Cell*, 16(1): 39-50 (2015).
Rand et al., "MYC Releases Early Reprogrammed Human Cells from Proliferation Pause via Retinoblastoma Protein Inhibition," *Cell Rep.*, 23(2): 361-375 (2018).

\* cited by examiner

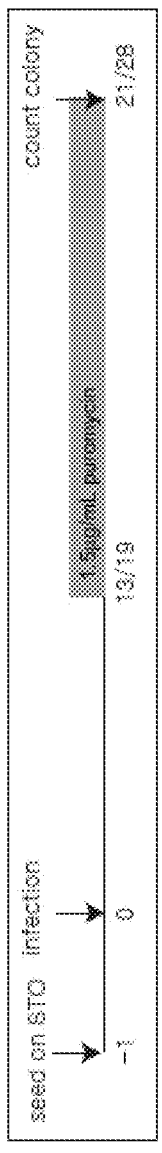
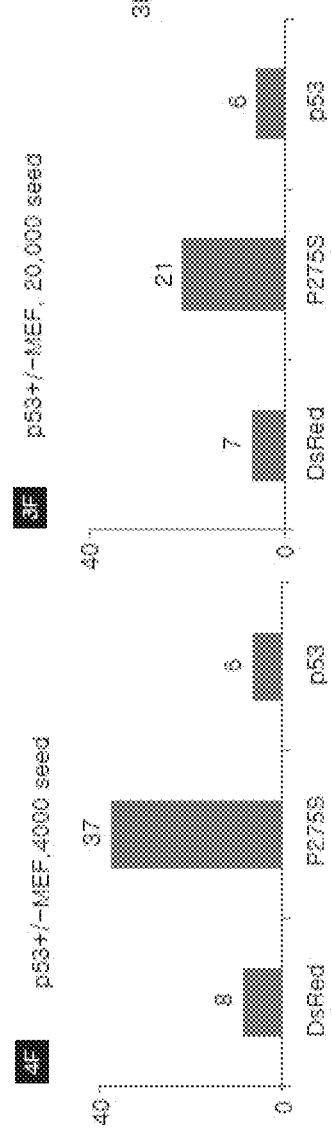
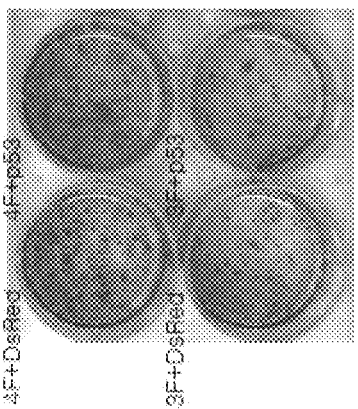
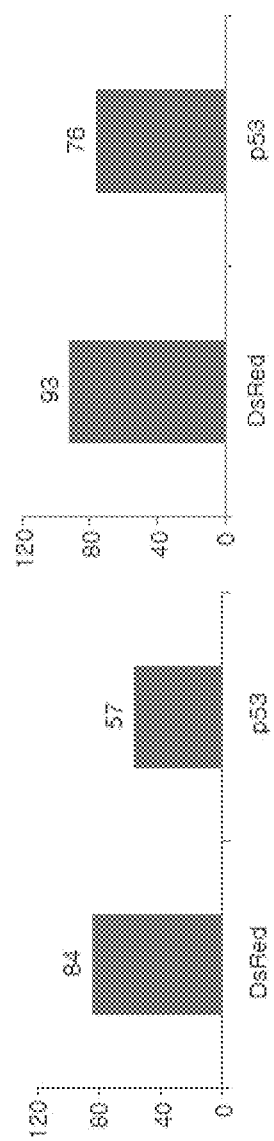
FIG. 3A
FIG. 3B
FIG. 3C
FIG. 3D
FIG. 3E
FIG. 3F
FIG. 3G

SSEA1

AP

FIG. 13A
FIG. 13B
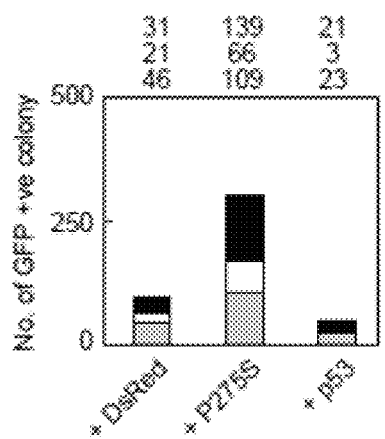
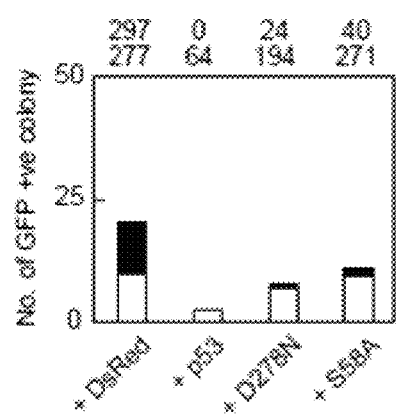

METHOD OF MAKING INDUCED
PLURIPOTENT STEM CELLS USING P53
INHIBITORS

CROSS-REFERENCE TO RELATED APPLICATIONS

This patent application is a continuation of U.S. patent application Ser. No. 13/942,208, filed Jul. 15, 2013, which is a divisional of U.S. patent application Ser. No. 12/672,042, filed Apr. 1, 2010, now U.S. Pat. No. 8,530,238, which is the U.S. national phase of International Patent Application No. PCT/JP2009/062173, filed on Jun. 26, 2009, which claims the benefit of U.S. Provisional Patent Application No. 61/076,487, filed on Jun. 27, 2008, U.S. Provisional Patent Application No. 61/095,573, filed on Sep. 9, 2008, U.S. Provisional Patent Application No. 61/194,700, filed on Sep. 30, 2008, U.S. Provisional Patent Application No. 61/200,307, filed on Nov. 25, 2008, and U.S. Provisional Patent Application No. 61/209,686, filed on Mar. 10, 2009, which are incorporated by reference in their entireties herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 45,041 bytes ASCII (Text) file named "741205SequenceListing.TXT," created on Nov. 16, 2018.

TECHNICAL FIELD OF THE INVENTION

The present invention relates to a method of improving the efficiency of establishment of induced pluripotent stem (hereinafter referred to as iPS) cells and a drug therefor. More specifically, the present invention relates to a method of improving the efficiency of establishment of iPS cells by inhibiting the p53 function in the step of somatic cell nuclear reprogramming, and an agent for improving the efficiency of establishment of iPS cells with an inhibitor of p53 function as an active ingredient.

BACKGROUND OF THE INVENTION

In recent years, mouse and human iPS cells have been established one after another. Yamanaka et al. induced iPS cells by introducing the Oct3/4, Sox2, Klf4 and c-Myc genes into fibroblasts derived from a reporter mouse wherein the neomycin resistance gene is knocked-in into the Fbx15 locus, and forcing the cells to express the genes (1,2). Okita et al. (3) succeeded in establishing iPS cells (Nanog iPS cells) that show almost the same gene expression and epigenetic modification as those in embryonic stem (ES) cells by producing a transgenic mouse wherein the green fluorescent protein (GFP) and puromycin-resistance genes are integrated into the locus of Nanog, whose expression is more localized in pluripotent cells than Fbx15 expression, forcing the fibroblasts derived from the mouse to express the above-mentioned 4 genes, and selecting puromycin-resistant and GFP-positive cells. Similar results were confirmed by other groups (4,5). Thereafter, it was revealed that iPS cells could also be produced with 3 factors other than the c-Myc gene (6).

Furthermore, Yamanaka et al. succeeded in establishing iPS cells by introducing the same 4 genes as those used in the mouse into human skin fibroblasts (1,7). On the other hand, a group of Thomson et al. produced human iPS cells using Nanog and Lin28 in place of Klf4 and c-Myc (8,9). Park et al. (10) produced human iPS cells using TERT, which is known as the human cell immortalizing gene, and the SV40 large T antigen, in addition to the 4 factors Oct3/4, Sox2, Klf4 and c-Myc. Hence, it has been demonstrated that iPS cells comparable to ES cells in pluripotency can be produced in both humans and mice by introducing defined factors into somatic cells.

However, the efficiency of iPS cell establishment is low at less than 1%. Especially, a problem of extremely low efficiency of iPS cell establishment occurs when they are produced by introducing 3 factors (Oct3/4, Sox2 and Klf4) other than c-Myc, which is feared to cause tumorigenesis in tissues or individuals differentiated from iPS cells, into somatic cells.

REFERENCES CITED

1. WO 2007/069666 A1
2. Takahashi, K. and Yamanaka, S., *Cell*, 126: 663-676 (2006)
3. Okita, K. et al., *Nature*, 448: 313-317 (2007)
4. Wernig, M. et al., *Nature*, 448: 318-324 (2007)
5. Maherali, N. et al., *Cell Stem Cell*, 1: 55-70 (2007)
6. Nakagawa, M. et al., *Nat. Biotethnol.*, 26: 101-106 (2008)
7. Takahashi, K. et al., *Cell*, 131: 861-872 (2007)
8. WO 2008/118820 A2
9. Yu, J. et al., *Science*, 318: 1917-1920 (2007)
10. Park, I. H. et al., *Nature*, 451: 141-146 (2008)

SUMMARY OF THE INVENTION

It is an object of the present invention to provide a means of improving the efficiency of establishment of iPS cells; another object of the present invention is to provide a method of efficiently producing iPS cells using the means.

The present inventors conducted extensive investigations with the aim of accomplishing the above-described objects, and found that by inhibiting the p53 function in the step of somatic cell nuclear reprogramming, the efficiency of establishment of iPS cells can be remarkably increased. The effect was particularly remarkable in human cells. Also, by inhibiting the p53 function, even with 3 factors, an establishment efficiency closer to the efficiency with 4 factors was obtained, than by a conventional method. Furthermore, the present inventors succeeded in establishing iPS cells with ease by deleting the p53 function even for T lymphocytes, for which it has conventionally been thought to be difficult to establish iPS cells, and have developed the present invention.

Accordingly, the present invention provides:

[1] A method of improving the efficiency of establishment of iPS cells, comprising inhibiting the p53 function in the step of somatic cell nuclear reprogramming.

[2] The method according to [1] above, wherein the p53 function is inhibited by bringing a chemical inhibitor of p53 into contact with a somatic cell.

[3] The method according to [1] above, wherein the p53 function is inhibited by bringing a dominant negative mutant of p53 or a nucleic acid that encodes the same into contact with a somatic cell.

[4] The method according to [1] above, wherein the p53 function is inhibited by bringing a nucleic acid selected from the group consisting of siRNAs and shRNAs against p53 and DNAs that encode the same into contact with a somatic cell.

[5] The method according to [1] above, wherein the p53 function is inhibited by bringing an inhibitor of p53 pathway into contact with a somatic cell.

[6] An agent for improving the efficiency of establishment of iPS cells, the agent comprising an inhibitor of p53 function.

[7] The agent according to [6] above, wherein the inhibitor is a chemical inhibitor.

[8] The agent according to [6] above, wherein the inhibitor is a dominant negative mutant of p53 or a nucleic acid that encodes the same.

[9] The agent according to [6] above, wherein the inhibitor is a nucleic acid selected from the group consisting of siRNAs and shRNAs against p53 and DNAs that encode the same.

[10] The agent according to [6] above, wherein the inhibitor is an inhibitor of p53 pathway.

[11] A method of producing iPS cells, comprising bringing a nuclear reprogramming substance and an inhibitor of p53 functional into contact with a somatic cell.

[12] The method according to [11] above, wherein the inhibitor is a chemical inhibitor.

[13] The method according to [11] above, wherein the inhibitor is a dominant negative mutant of p53 or a nucleic acid that encodes the same.

[14] The method according to [11] above, wherein the inhibitor is a nucleic acid selected from the group consisting of siRNAs and shRNAs against p53 and DNAs that encode the same.

[15] The method according to [11] above, wherein the inhibitor is an inhibitor of p53 pathway.

[16] The method according to [11] above, wherein the nuclear reprogramming substances are Oct3/4, Klf4 and Sox2, or nucleic acids that encode the same.

[17] The method according to [11] above, wherein the nuclear reprogramming substances are Oct3/4, Klf4, Sox2 and c-Myc, or nucleic acids that encode the same.

[18] The method according to [11] above, wherein the somatic cell is a T cell.

[19] An iPS cell wherein a T cell antigen receptor (TCR) gene is rearranged, the iPS cell being obtained by reprogramming a T cell.

[20] An iPS cell comprising a dominant negative mutant of p53 or an exogenous nucleic acid that encodes an siRNA or shRNA against p53.

Because inhibitors of p53 function make it possible to remarkably increase the efficiency of establishment of iPS cells, the same are particularly useful in the induction of iPS cells by means of 3 factors except c-Myc, for which the efficiency of establishment has conventionally been very low. Because c-Myc is feared to cause tumorigenesis when reactivated, the improvement in the efficiency of establishment of iPS cells using the 3 factors is of paramount utility in applying iPS cells to regenerative medicine.

Because the iPS cells derived from a finally differentiated T cell have TCR already rearranged therein, the iPS cells are useful as a T cell immunotherapeutic agent, provided that the iPS cells are induced from a T cell that recognizes a cell that presents a particular antigen (e.g., cancer cells, infected cells and the like), amplified in large amounts, and allowed to re-differentiate into cytotoxic T cells (CTLs).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A and FIG. 1B show results of introduction of 4 factors (Oct3/4, Sox2, Klf4, c-Myc) to induce iPS cells, and results of introduction of 3 factors (Oct3/4, Sox2, Klf4) to induce iPS cells, respectively. In the figures, "p53+/−" shows results for p53-hetero-deficient cells (control); "p53−/−" shows results for p53-homo-deficient cells. In the figures, the axis of ordinates indicates the number of GFP-positive colonies. Each graph shows a total of three experiments.

FIGS. 3A-3D show results of an examination of effects of introduction of a dominant negative mutant of p53 (p53P275S) on the establishment of iPS cells. FIG. 3A shows an outline of the experimental procedure. FIG. 3B and FIG. 3C show results of introduction of 4 factors and results of introduction of 3 factors, respectively. In the figures, "P275S" shows results of introduction of p53P275S. In the figures, "DsRed" and "p53" show results of introduction of DsRedExpress and mutation-free wild-type p53, respectively, in place of p53P275S. The axis of ordinates indicates the number of GFP-positive colonies. FIG. 3D shows photographs of colonies corresponding to the respective results.

FIGS. 3E-3G show results of an examination of effects of introduction of p53 into p53-homo-deficient mice on the establishment of iPS cells. FIG. 3E and FIG. 3F show results of introduction of 4 factors and 3 factors, respectively. In the figures, "DsRed" shows results of introduction of DsRedExpress; "p53" shows results of introduction of wild-type p53. The axis of ordinates indicates the number of GFP-positive colonies. FIG. 3G shows photographs of colonies corresponding to the respective results.

FIG. 4A shows an outline of the experimental procedure; FIG. 4B shows experimental results. In FIG. 4B, "DMSO" shows results of treatment with DMSO (control); "Pifithrin α, p-cyclic, nitro" shows results of treatment with Pifithrin. The axis of ordinates indicates the number of GFP-positive colonies.

FIG. 12A shows iPS cells which were generated from Nanog-GFP reporter MEF, which were either p53 wild-type, heterozygous, or homozygous, by the three factors. After retroviral transduction, 5000 live cells were collected by a flowcytometer. GFP-positive colonies were counted 28 days after the transduction and shown of the top of the graphs. Data of three independent experiments are shown. FIG. 12B shows iPS cells which were generated by the three factors from single sorted cells in wells of 96-well plates. GFP-positive colonies were counted 28 days after the transduction. Data from three independent experiments are shown. FIG. 12C shows iPS cells which were generated by the four factors, including c-Myc, from single sorted cells in wells of 96-well plates. GFP-positive colonies were counted 21 days after the transduction. Data from three independent experiments are shown.

FIGS. 13A and 13B show iPS generation from p53 heterozygous or homozygous MEFs by the three factors co-transduced with wild-type or mutant p53. FIG. 13A shows Retrovirus expressing either the dominant negative p53 mutant (P275S) or wild-type was co-transduced with the three factors into Oct3/4-GFP, p53 heterozyous MEFs. After retroviral transduction, 5000 cells were collected and GFP-positive colonies were counted 28 days after the transduction. Data of three independent experiments are shown. FIG. 13B shows Retrovirus expressing either the wild-type or mutant p53 was co-tranduced with the three factors into Nanog-GFP, p53 homozyous MEFs. After retroviral transduction, 5000 live cells were collected and GFP-positive colonies were counted 28 days after the transduction. Data of two independent experiments are shown.

FIGS. 14-16B show characterization of iPS cells derived from p53 hetrozygous or homozygous MEFs.

FIG. 14 shows phase contrast images (upper) and fluorescent images (lower) of iPS cells derived from Nanog-GFP, p53-null MEFs by the three or four factors. Bars indicate 100 μm.

FIG. 15 shows RT-PCR analysis of the expression of ES cell marker genes, p53 and the four factors. By using specific sets of primers, the total expression, endogenous expression and transgene expression of the four factors were distinguished.

FIGS. 16A and 16B show histological examination of teratomas derived from p53-null iPS cells with the three (FIG. 16A) or four (FIG. 16B) factors. FIG. 16A shows hematoxylin-eosin staining of neural tissues (upper left), cartilage (upper right), muscle (lower left), and gut-like epithelial tissues (lower right). FIG. 16B shows hematoxylin-eosin staining of undifferentiated cells (upper) and neural tissues (lower).

FIGS. 17A-20B show increased efficiency of human iPS cell generation by p53 suppression.

FIGS. 17A-17C show effects of mutant p53 co-transduction on iPS generation from HDFs by the four or three factors. The retroviral vector expressing either P275S or DD was transduced into HDFs together with the four or three reprogramming factors. Shown are the numbers of iPS cell colonies by the four factors ((FIG. 17A), from 5×10$^3$ HDFs) and by the three factors ((FIG. 17B), from 4×10$^4$ HDFs). FIG. 17C shows teratomas derived from human iPS cells, which were generated with the three reprogramming factors and the p53DD mutant. Shown are hematoxylin-eosin staining of neural tissues (upper left), cartilage (upper right), muscle (lower left), and gut-like epithelial tissues (lower right).

FIG. 18 shows suppression of p53 production by p53 shRNA. Retroviral vectors for p53 shRNA or control RNA were transduced into HDFs. Six days after the transduction, p53 protein levels were determined by western blot analyses.

FIG. 19 shows effects of p53 shRNA co-transduction on iPS generation from HDFs by the four factors. The retroviral vector expressing either p53 shRNA or control RNA was transduced into HDFs together with the four reprogramming factors. To rescue RNAi-mediated knockdown, a retroviral vector for mouse p53 was co-introduced. Shown are the numbers of iPS colonies in four experiments.

FIGS. 20A-20B show effects of p53 shRNA co-transduction on iPS generation from HDFs by the three factors. The retroviral vector expressing either p53 shRNA or control RNA was transduced into HDFs together with the three reprogramming factors. To rescue RNAi-mediated knockdown, a retroviral vector for mouse p53 was co-introduced. Shown are the numbers of iPS colonies from 5×10$^4$ HDFs (FIG. 20A) or 5×10$^5$ HDFs (FIG. 20B) in two experiments.

DETAILED DESCRIPTION OF THE INVENTION

Figure 1A:
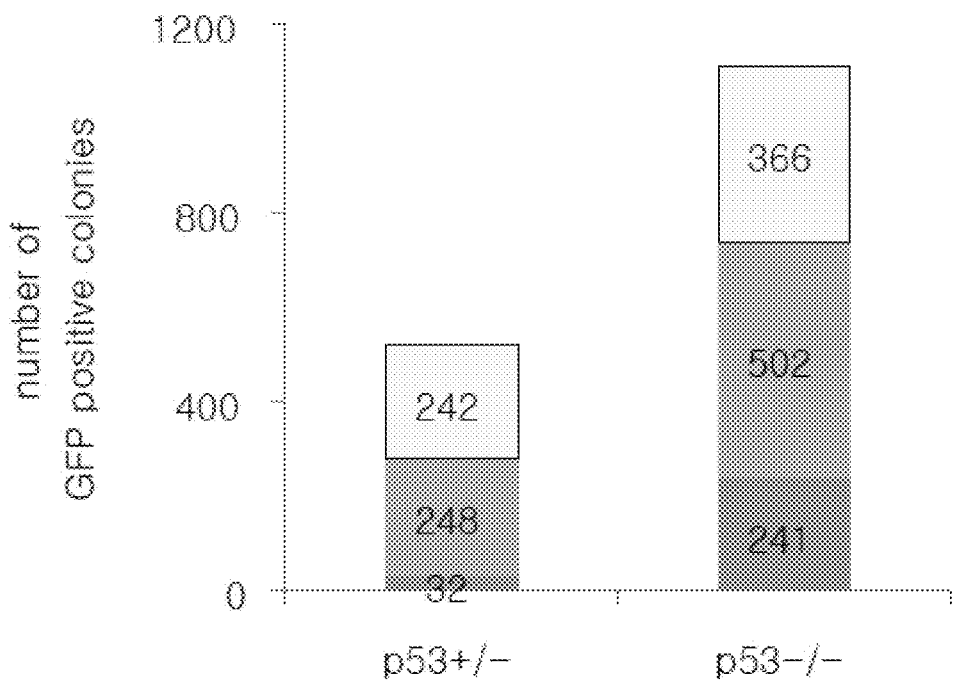
FIGS. 1A and 1B shows results of an examination of effects of p53 deficiency on the establishment of iPS cells.

The present invention provides a method of improving the efficiency of establishment of iPS cells by inhibiting the p53 function in the step of somatic cell nuclear reprogramming. The choice of means of inhibiting the p53 function is not particularly limited; preferably, a method wherein an inhibitor of p53 function is brought into contact with a somatic cell can be mentioned.

As mentioned herein, "an inhibitor of p53 function" may be any substance, as far as it is capable of inhibiting either (a) the function of the p53 protein or (b) the expression of the p53 gene. That is, not only substances that act directly on the p53 protein to inhibit the function thereof and substances that act directly on the p53 gene to inhibit the expression thereof, but also substances that act on a factor involved in p53 signal transduction to result in inhibition of the function of the p53 protein or the expression of the p53 gene, are also included in the scope of "an inhibitor of p53 function" as mentioned herein.

Examples of substances that inhibit the function of the p53 protein include, but are not limited to, a chemical inhibitor of p53, a dominant negative mutant of p53 or a nucleic acid that encodes the same, an anti-p53 antagonist antibody or a nucleic acid that encodes the same, a decoy nucleic acid comprising a consensus sequence of a p53-responsive element, a substance that inhibits the p53 pathway, and the like. Preferably, a chemical inhibitor of p53, a dominant negative mutant of p53 or a nucleic acid that encodes the same, and a p53 pathway inhibitor can be mentioned.

(a1) Chemical Inhibitors of p53

Examples of chemical inhibitors of p53 include, but are not limited to, p53 inhibitors typified by pifithrin (PFT)-α and -β, which are disclosed in WO 00/44364, PFT-µ disclosed in Storm et al. (*Nat. Chem. Biol.* 2, 474 (2006)), analogue thereof and salts thereof (for example, acid addition salts such as hydrochlorides and hydrobromides, and the like) and the like. Thereof, PFT-α and analogues thereof [2-(2-Imino-4,5,6,7-tetrahydrobenzothiazol-3-yl)-1-p-tolylethanone, HBr (product name: Pifithrin-α) and 1-(4-Nitrophenyl)-2-(4,5,6,7-tetrahydro-2-imino-3(2H)-benzothiazolyl)ethanone, HBr (product name: Pifithrin-α, p-Nitro)], PFT-β and analogues thereof [2-(4-Methylphenyl)imidazo[2,1-b]-5,6,7,8-tetrahydrobenzothiazole, HBr (product name: Pifithrin-α, Cyclic) and 2-(4-Nitrophenyl)imidazo[2,1-b]-5,6,7,8-tetrahydrobenzothiazole(product name: Pifithrin-α, p-Nitro, Cyclic)], and PFT-µ [Phenylacetylenylsulfonamide (product name: Pifithrin-t)] are commercially available from Merck.

Contact of a chemical inhibitor of p53 with a somatic cell can be performed by dissolving the inhibitor at an appropriate concentration in an aqueous or non-aqueous solvent, adding the solution of the inhibitor to a medium suitable for cultivation of somatic cells isolated from a human or mouse (for example, minimal essential medium (MEM), Dulbecco's modified Eagle medium (DMEM), RPMI1640 medium, 199 medium, F12 medium and the like supplemented with about 5 to 20% fetal bovine serum) so that the inhibitor concentration will fall in a range that fully inhibits the p53 function and does not cause cytotoxicity, and culturing the cells for a given period. The inhibitor concentration varies depending on the kind of inhibitor used, and is chosen as appropriate over the range of about 0.1 nM to about 100 nM. Duration of contact is not particularly limited, as far as it is sufficient to achieve nuclear reprogramming of the cells; usually, the inhibitor may be allowed to co-present in the medium until a pluripotent marker positive colony emerges.

The p53 gene is known as a tumor suppressor gene; permanent inhibition of p53 function potentially increases the risk of carcinogenesis. Chemical inhibitors of p53 are extremely useful, not only because of the advantage of permitting introduction into cells simply by the addition to the medium, but also because of the ability to terminate the inhibition of p53 function, easily and quickly, by removing the medium containing the inhibitor after induction of iPS cells.

(a2) Dominant Negative Mutants of p53

The choice of dominant negative mutant of p53 is not particularly limited, as far as the mutant is capable of competitively acting against the wild-type p53 protein endogenously expressed in somatic cells to inhibit the function thereof, for example, p53P275S, resulting from point mutation of the proline at the position 275 (in the case of humans, position 278) located in the DNA-binding region of mouse p53 to serine (de Vries, A., *Proc. Natl. Acad. Sci. USA*, 99, 2948-2953 (2002)); p53DD, resulting from deletion of the amino acids at the positions 14-301 of mouse p53 (in human p53, corresponds to the positions 11-304) (Bowman, T., *Genes Develop.*, 10, 826-835 (1996)), and the like can be mentioned. Other known mutants include, for example, p53S58A, resulting from point mutation of the serine at the position 58 of mouse p53 (in the case of humans, position 61) to alanine; p53C135Y, resulting from point mutation of the cysteine at the position 135 of human p53 (in the case of mice, position 132) to tyrosine; p53A135V, resulting from point mutation of the alanine at the position 135 of mouse p53 (in the case of humans, position 138) to valine; p53R172H, resulting from point mutation of the arginine at the position 172 (in the case of humans, position 175) to histidine; p53R270H, resulting from point mutation of the arginine at the position 270 (in the case of humans, position 273) to histidine; p53D278N, resulting from point mutation of the aspartic acid at the position 278 of mouse p53 (in the case of humans, position 281) to asparagine, and the like; these can be used in the same way.

A dominant negative mutant of p53 can be obtained by for example, the technique described below. First, an appropriate oligonucleotide is synthesized as a probe or primer on the basis of the mouse or human p53 cDNA sequence information shown by SEQ ID NO: 1 or 3, and a mouse or human p53 cDNA is cloned from a mRNA, cDNA or cDNA library derived from a mouse or human cell or tissue, using the hybridization method or the (RT-)PCR method, and is subcloned into an appropriate plasmid. In a form wherein a codon of the site into which a mutation is to be introduced (for example, in the case of p53P275S, cct, which is shown by nucleotide numbers 951-953 in the nucleotide sequence shown by SEQ ID NO:1) is replaced with a codon that encodes another desired amino acid (for example, in the case of p53P275S, tct), a primer comprising the site is synthesized, and inverse PCR is performed using this primer with the plasmid incorporating the p53 cDNA as a template, whereby a nucleic acid that encodes the desired dominant negative mutant is acquired. In the case of a deletion mutant like p53DD, a primer may be designed outside the site to be deleted, and inverse PCR may be performed as described above. By introducing the thus-obtained nucleic acid that encodes the dominant negative mutant into a host cell, and recovering a recombinant protein from the cultured cell or its conditioned medium, the desired dominant negative mutant can be acquired.

Contact of a dominant negative mutant with a somatic cell can be achieved using a method known per se for protein transfer into a cell. Such methods include, for example, the method using a protein transfer reagent, the method using a protein transfer domain (PTD)- or cell penetrating peptide (CPP)-fusion protein, the microinjection method and the like. Protein transfer reagents are commercially available, including BioPOTER Protein Delivery Reagent (Gene Therapy Systems), Pro-Ject™ Protein Transfection Reagent (PIERCE) and ProVectin (IMGENEX), which are based on a cationic lipid; Profect-1 (Targeting Systems), which is based on a lipid; Penetrain Peptide (Q biogene) and Chariot Kit (Active Motif), which are based on a membrane-permeable peptide, and GenomONE (Ishihara Sangyo), which is based on HVJ envelop (inactivated Sendai virus), and the like. The transfer can be achieved per the protocols attached to these reagents, a common procedure being as described below. A dominant negative mutant of p53 is diluted in an appropriate solvent (for example, a buffer solution such as PBS or HEPES), a transfer reagent is added, the mixture is incubated at room temperature for about 5 to 15 minutes to form a complex, this complex is added to the cells after medium exchange with a serum-free medium, and the cells are incubated at 37° C. for one to several hours. Thereafter, the medium is removed and replaced with a serum-containing medium.

Developed PTDs include those using the cell penetrating domain of a protein, such as drosophila-derived AntP, HIV-derived TAT (Frankel, A. et al, Cell 55,1189-93 (1988) or Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. Nature Biotechnol. 19, 1173-6 (2001)), Pep-7 (Gao, C. et al. Bioorg. Med. Chem. 10, 4057-65 (2002)), SynB1 (Rousselle, C. et al. MoI. Pharmacol. 57, 679-86 (2000)), HN-I (Hong, F. D. & Clayman, G L. Cancer Res. 60, 6551-6 (2000)), and HSV-derived VP22. CPPs derived from the PTDs include polyarginines such as 11R (Cell Stem Cell, 4:381-384(2009)) and 9R (Cell Stem Cell, doi: 10.1016/j.stem.2009.05.005 (2009)). A fusion protein expression vector incorporating a cDNA of a dominant negative mutant of p53 and a PTD or CPP sequence is prepared to allow recombinant expression of the fusion protein, and the fusion protein is recovered for use in the transfer. This transfer can be achieved as described above, except that no protein transfer reagent is added.

Microinjection, a method of placing a protein solution in a glass needle having a tip diameter of about 1 µm, and injecting the solution into a cell, ensures the transfer of the protein into the cell.

As described above, permanent inhibition of p53 function potentially increases the risk of carcinogenesis; however, because a dominant negative mutant of p53 undergoes degradation by protease in the transfected cell and disappears gradually, and correspondingly the p53 function endogenously occurring in the cell is restored, use of the mutant protein can be suitable in cases where high safety is required as in the case where the iPS cells obtained are utilized for therapeutic purposes.

(a3) Nucleic Acids that Encode a Dominant Negative Mutant of p53

However, taking into account the ease of introduction into a somatic cell, a dominant negative mutant of p53 may be used in the form of a nucleic acid that encodes a protein, rather than of the protein itself. Therefore, in another preferred mode of embodiment of the present invention, the inhibitor of p53 function is a nucleic acid that encodes a dominant negative mutant of p53. The nucleic acid may be a DNA or an RNA, or a DNA/RNA chimera, and is preferably a DNA. The nucleic acid may be double-stranded or single-stranded. A cDNA that encodes a dominant negative mutant of p53 can be cloned by the technique described above with respect to preparation of the mutant protein.

The cDNA isolated is inserted into an appropriate expression vector comprising a promoter capable of functioning in a target somatic cell. Useful expression vectors include, for example, viral vectors such as retrovirus, lentivirus, adenovirus, adeno-associated virus, herpesvirus and Sendai virus, plasmids for the expression in animal cells (e.g., pAl-11, pXT1, pRc/CMV, pRc/RSV, pcDNAI/Neo) and the like. A kind of vector used can be chosen as appropriate according to the intended use of the iPS cells obtained.

Useful promoters used in the expression vector include, for example, SRa promoter, SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter, EF-alpha promoter, CAG promoter and the like. Preference is given to MoMuLV LTR, CMV promoter, SRa promoter, EF-alpha promoter, CAG promoter and the like.

The expression vector may harbor, as desired, in addition to a promoter, an enhancer, a polyadenylation signal, a selectable marker gene, an SV40 replication origin and the like. Examples of the selectable marker gene include the dihydrofolate reductase gene, the neomycin resistance gene, the puromycin resistance gene and the like.

An expression vector harboring a nucleic acid encoding a dominant negative mutant of p53 can be introduced into a cell by a technique known per se according to the kind of the vector. In the case of a viral vector, for example, a plasmid containing the nucleic acid encoding a dominant negative mutant of p53 is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector as a vector are disclosed in WO2007/69666, *Cell*, 126, 663-676 (2006) and *Cell*, 131, 861-872 (2007); when a lentiviral vector is used as a vector, a disclosure is available in *Science*, 318, 1917-1920 (2007). When iPS cells are utilized for therapeutic purposes, permanent inhibition of the p53 function potentially increases the risk of carcinogenesis in tissues and organs differentiated from iPS cells; therefore, the nucleic acid that encodes a dominant negative mutant of p53 is preferably expressed transiently, without being integrated into the chromosome of the cells. From this viewpoint, use of an adenoviral vector, whose integration into chromosome is rare, is preferred. Specific means using an adenoviral vector is disclosed in *Science*, 322, 945-949 (2008). Because adeno-associated virus is also low in the frequency of integration into chromosome, and is lower than adenoviral vectors in terms of cytotoxicity and inflammation-causing activity, it can be mentioned as another preferred vector. Because persistent expression type Sendai viral vector is capable of being stably present outside the chromosome, and can be degraded and removed using an siRNA as required, it is preferably utilized as well. Regarding persistent expression type Sendai viral vector, one described in J Biol. Chem., 282, 27383-27391 (2007) can be used.

When a retroviral vector or a lentiviral vector is used, even if silencing of the transgene has occurred, it possibly becomes reactivated; therefore, for example, a method can be used preferably wherein a nucleic acid that encodes a dominant negative mutant of p53 is cut out using the Cre/loxP system, when becoming unnecessary. That is, with a loxP sequence arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Chang et al., Stem Cells, 27: 1042-1049 (2009).

Meanwhile, in the case of a plasmid vector, which is a non-viral vector, the vector can be introduced into a cell using the lipofection method, liposome method, electroporation method, calcium phosphate co-precipitation method, DEAE dextran method, microinjection method, gene gun method and the like. Also when a plasmid vector is used, its integration into chromosome is rare, the transgene is degraded and removed by DNase in the cells; therefore, when iPS cells are utilized for therapeutic purposes, use of a plasmid vector can be a preferred mode of embodiment. A specific means using a plasmid as a vector is described in, for example, *Science*, 322, 949-953 (2008) and the like.

Another preferable non-integration type vector is an episomal vector, which is autonomously replicable outside chromosome. Specific means using an adenoviral vector is disclosed in *Science*, 324, 797-801(2009).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transferase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji et al., Nature advance online publication 1 Mar. 2009 (doi: 10.1038/nature07864), Woltjen et al., Nature advance online publication 1 Mar. 2009 (doi: 10.1038/nature07863). In another embodiment, tetracycline responsive element in promoter region (Tet-On® & Tet-Off® Gene Expression Systems, Clontech) can be used for the excision of transgenes.

(a4) p53 Pathway Inhibitors

Here, the term p53 pathway is used with a meaning including all upstream signal cascades that can activate p53 and all downstream signal cascades mediated by activated p53. Therefore, p53 pathway inhibitors include all substances that inhibit any one of the aforementioned signal transduction pathways, but in a preferred mode of embodiment, the p53 pathway inhibitor is a substance that inhibits the expression or function (Myc inhibitory activity) of p21, whose transcription is activated by p53; for example, siRNA, shRNA, antisense nucleic acids, ribozymes against p21 and the like can be mentioned. These nucleic acids that inhibit the expression of p21 can be designed and synthesized in the same manner as the method for siRNA, shRNA, antisense nucleic acids, and ribozymes against p53 described below, and can be introduced into a somatic cell. The nucleic acids may be provided in the form of a vector that expresses them, the vector can be constructed in the same manner as the method for a vector that expresses an siRNA, shRNA, antisense nucleic acid, or ribozyme against p53 described below, and introduced into a somatic cell.

In another preferred mode of embodiment, the p53 pathway inhibitor is a substance that inhibits the ARF-MDM2-p53 pathway; for example, as ARF-MDM2-p53 pathway inhibitors, MDM2, which binds directly to p53 to promote the extranuclear transportation or ubiquitination thereof or a nucleic acid that encodes the same, $p19^{ARF}$, which inhibits the action of MDM2 on p53, a substance that inhibits the expression or function of ATM (ataxia-telangiectasia mutated) (for example, siRNAs and shRNAs against these factors) and the like can be mentioned.

(a5) Other Substances

As examples of other substances that inhibit the function of the p53 protein, anti-p53 antagonist antibody or a nucleic acid that encodes the same can be mentioned. The anti-p53 antagonist antibody may be a polyclonal antibody or a monoclonal antibody. The isotype of the antibody is not particularly limited, and is preferably IgG, IgM or IgA, particularly preferably IgG. The antibody may be, in addition to a complete antibody molecule, for example, a fragment such as Fab, Fab', or F(ab')2, a conjugate molecule prepared by a gene engineering technique, such as scFv, scFv-Fc, minibody, or diabody, or a derivative thereof modified with a molecule having protein-stabilizing action, such as polyethylene glycol (PEG). An anti-p53 antagonist antibody can be produced using p53 or a partial peptide thereof as an antigen, by a method of antibody or anti-serum production known per se. As examples of known anti-p53 antagonist antibodies, PAb1801 (Oncogene Science Ab-2) and DO-1 (Oncogene Science Ab-6) (Gire and Wynford-Thomas, *Mol. Cell. Biol.*, 18, 1611-1621 (1998)) and the like can be mentioned. A nucleic acid that encodes an anti-p53 antagonist antibody can be isolated from a hybridoma that produces an anti-p53 monoclonal antibody by a conventional method. The H-chain and L-chain genes obtained may be joined together to prepare a nucleic acid that encodes a single-chain antibody. Preferably, these antibodies are fused with aforementioned PTD or CPP.

As another substance that inhibits the function of the p53 protein, an anti-p21 antagonist antibody or a nucleic acid that encodes the same can be mentioned. An anti-p21 antagonist antibody and a nucleic acid that encodes the same can also be prepared as with the aforementioned anti-p53 antagonist antibody and nucleic acid that encodes the same.

Still another substance that inhibits the function of the p53 protein is a decoy nucleic acid comprising a consensus sequence of p53-responsive element (e.g., Pu-Pu-Pu-G-A/T-T/A-C-Py-Py-Py (Pu: purine base, Py: pyrimidine base); SEQ ID NO:27). Such a nucleic acid can be synthesized on the basis of the aforementioned nucleotide sequence information using an automated DNA/RNA synthesizer. Alternatively, such a decoy nucleic acid is commercially available (e.g., p53 transcription factor decoy (GeneDetect.com)).

An anti-p53 antagonist antibody and an anti-p21 antagonist antibody, or a nucleic acid that encodes the antibody can be introduced into a cell with the method described in the statement of a dominant negative mutant of p53 or a nucleic acid that encodes the mutant, respectively. The aforementioned decoy nucleic acid can be introduced into a cell by lipofection method and the like.

Meanwhile, as examples of substances that inhibit the expression of the p53 gene, siRNAs or shRNAs against p53, vectors that express an siRNA or shRNA against p53, antisense nucleic acids against p53 and ribozymes against p53, and the like can be mentioned, and siRNAs and shRNAs against p53 and vectors that express an siRNA or an shRNA are preferable.

(b1) siRNA and shRNA Against p53

An siRNA against p53 can be designed on the basis of the mouse or human p53 cDNA sequence information shown by SEQ ID NO: 1 or 3, in accordance with, for example, the rules proposed by Elbashir et al. (*Genes Dev.*, 15, 188-200 (2001)). The target sequence for the siRNA is, as a general rule, AA+$(N)_{19}$, but may be AA+$(N)_{21}$ or NA+$(N)_{21}$. The 5' end of the sense strand need not to be AA. Although the position of the target sequence is not particularly limited, it is desirable that the target sequence be selected between 5'-UTR and about 50 bases from the start codon, as well as from a region other than 3'-UTR. The GC content of the target sequence is also not particularly limited, but the content is preferably about 30 to about 50%; a sequence with no irregularity in GC distribution and with only a few repeats is desirable. When a polIII promoter is used as a promoter in designing a vector that expresses an siRNA or shRNA of (b2) below, a sequence of 4 or more T or A bases in succession should not be chosen, so as to prevent polymerase transcription from ceasing.

The target sequence candidates selected on the basis of the above-described rules are examined for homology to sequences of 16-17 bases in succession in mRNAs other than the target, using a homology search software program such as BLAST (http://www.ncbi.nlm.nih.gov/BLAST/), so as to confirm the specificity of the target sequences selected. For the target sequences for which the specificity has been confirmed, a double-stranded RNA consisting of a sense strand having a 3'-terminal overhang of TT or UU in 19-21 bases after AA (or NA) and a sequence complementary to the 19-21 bases, and an antisense strand having a 3'-terminal overhang of TT or UU, is designed as an siRNA. Also, an shRNA can be designed by choosing as appropriate an optionally chosen linker sequence capable of forming a loop structure (for example, about 8-25 bases), and ligating the aforementioned sense strand and antisense strand via the linker sequence.

Sequences of siRNAs and/or shRNAs can be searched for using search software programs available at no cost on various websites. Examples of such sites include, but are not limited to, the siRNA Target Finder (http://www.ambion-.com/jp/techlib/misc/siRNA_finder.html) and insert design tool for pSilencer™ Expression Vector (http://www.ambion.com/jp/techlib/misc/psilencer_converter.html), both provided by Ambion, and GeneSeer (http://codex.cshl.edu/scripts/newsearchhairpin.cgi), provided by RNAi Codex; and similar search is possible on the websites of QIAGEN, Takara Bio, SiSearch, Dharmacon, Whitehead Institute, Invitrogen, Promega and the like.

Shown below are the sequences of shRNAs against mouse p53 designed using software programs available on the websites of Ambion (SEQ ID NO:5-24) and RNAi Codex (SEQ ID NO:25 and 26). The underlined sequences are sense strands (bald letters) and antisense strands of dsRNAs resulting after cleavage with a dicer (not containing the 3'-overhang "TT"). Small letters indicate a mismatch or a loop.

[SEQ ID NO: 5]
5'-TTTGACTGGATGACTGCCATGGttcaagagaCCATGGCAGTCATCCAGTCTTTTTT-3'

[SEQ ID NO: 6]
5'-TTTGATATCCTGCCATCACCTCttcaagagaGAGGTGATGGCAGGATATCTTTTTT-3'

[SEQ ID NO: 7]
5'-TTTGGCCCAAGTGAAGCCCTCCttcaagagaGGAGGGCTTCACTTGGGCCTTTTTT-3'

[SEQ ID NO: 8]
5'-TTTGTGAAGCCCTCCGAGTGTCttcaagagaGACACTCGGAGGGCTTCACTTTTTT-3'

[SEQ ID NO: 9]
5'-TTTGCCCTCCGAGTGTCAGGAGttcaagagaCTCCTGACACTCGGAGGGCTTTTTT-3'

[SEQ ID NO: 10]
5'-TTTGTCTGTTATGTGCACGTACttcaagagaGTACGTGCACATAACAGACTTTTTT-3'

-continued

```
                                                             [SEQ ID NO: 11]
5'-TTTGTACTCTCCTCCCCTCAATttcaagagaATTGAGGGGAGGAGAGTACTTTTTT-3'

[SEQ ID NO: 12]
5'-TTTGCTATTCTGCCAGCTGGCGttcaagagaCGCCAGCTGGCAGAATAGCTTTTTT-3'

[SEQ ID NO: 13]
5'-TTTGACGTGCCCTGTGCAGTTGttcaagagaCAACTGCACAGGGCACGTCTTTTTT-3'

[SEQ ID NO: 14]
5'-TTTGAAGTCACAGCACATGACGttcaagagaCGTCATGTGCTGTGACTTCTTTTTT-3'

[SEQ ID NO: 15]
5'-TTTGTCACAGCACATGACGGAGttcaagagaCTCCGTCATGTGCTGTGACTTTTTT-3'

[SEQ ID NO: 16]
5'-TTTGGAAATTTGTATCCCGAGTttcaagagaACTCGGGATACAAATTTCCTTTTTT-3'

[SEQ ID NO: 17]
5'-TTTGTACATGTGTAATAGCTCCttcaagagaGGAGCTATTACACATGTACTTTTTT-3'

[SEQ ID NO: 18]
5'-TTTGACTCCAGTGGGAACCTTCttcaagagaGAAGGTTCCCACTGGAGTCTTTTTT-3'

[SEQ ID NO: 19]
5'-TTTGTCCTTTGCCCTGAACTGCttcaagagaGCAGTTCAGGGCAAAGGACTTTTTT-3'

[SEQ ID NO: 20]
5'-TTTGATCCGCGGGCGTAAACGCttcaagagaGCGTTTACGCCCGCGGATCTTTTTT-3'

[SEQ ID NO: 21]
5'-TTTGACCAAGAAGGGCCAGTCTttcaagagaAGACTGGCCCTTCTTGGTCTTTTTT-3'

[SEQ ID NO: 22]
5'-TTTGAAAGTGGGGCCTGACTCAttcaagagaTGAGTCAGGCCCCACTTTCTTTTTT-3'

[SEQ ID NO: 23]
5'-TTTGTTGGGGAATAGGTTGATAttcaagagaTATCAACCTATTCCCCAACTTTTTT-3'

[SEQ ID NO: 24]
5'-TTTGATTCTATCTTGGGCCCTCttcaagagaGAGGGCCCAAGATAGAATCTTTTTT-3'

[SEQ ID NO: 25]
5'-TTTGCAuTACAgGTACgTGTGTAgtgtgctgtccTACACATGTACTTGTAGTGTTTTTT-3'

[SEQ ID NO: 26]
5'-TTTGCAGTuTACTTuCCGCCgTAgtgtgctgtccTATGGCGGGAAGTAGACTGTTTTTT-3'
```

An siRNA against p53 can be prepared by synthesizing a sense strand oligonucleotide and antisense strand oligonucleotide designed as described above using an automated DNA/RNA synthesizer, respectively, and, for example, denaturing the oligonucleotides in an appropriate annealing buffer solution at about 90 to about 95° C. for about 1 minute, thereafter annealing the same at about 30 to about 70° C. for about 1 to about 8 hours. An shRNA against p53 can be prepared by synthesizing oligonucleotides having an shRNA sequence, designed as described above, using an automated DNA/RNA synthesizer, and allowing the same to self-anneal as described above.

Although the nucleotide molecules that constitute the siRNA and shRNA may be naturally occurring RNAs, the molecules can comprise various chemical modifications in order to increase the stability (chemical and/or to-enzyme) or specific activity (affinity for mRNA). For example, to prevent degradation by hydrolylases such as nuclease, the phosphoric acid residue (phosphate) of each nucleotide that constitutes the siRNA or shRNA can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —H or —OR (R represents, for example, $CH_3$(2'-O-Me), $CH_2CH_2OCH_3$(2'-O-MOE), $CH_2CH_2NHC(NH)NH_2$, $CH_2CONHCH_3$, $CH_2CH_2CN$ or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl and the like can be mentioned.

Regarding the conformation of the sugar moiety of RNA, two types are dominant: C2'-endo (S type) and C3'-endo (N type); in a single-stranded RNA, the sugar moiety occurs in an equilibrium of both, but when a double strand is formed, the conformation is fixed at the N type. Therefore, BNA (LNA) (Imanishi, T. et al., *Chem. Commun.*, 1653-9, 2002; Jepsen, J. S. et al., *Oligonucleotides*, 14, 130-46, 2004) and ENA (Morita, K. et al., *Nucleosides Nucleotides Nucleic Acids*, 22, 1619-21, 2003), which are RNA derivatives wherein the conformation of the sugar moiety is fixed at the N type by bridging the 2' oxygen and 4' carbon so as to confer strong bindability to the target RNA, can also be used preferably.

However, because replacing all ribonucleoside molecules in a naturally occurring RNA with modified type molecules can lead to the loss of RNAi activity, it is necessary to introduce a nucleoside modified to the minimum possible extent that allows the RISC complex to function.

An siRNA against p53 can also be purchased from, for example, Ambion (e.g., Ambion Cat #AM16708, an siRNA ID #69659, 69753, 69843, 187424, 187425, 187426), Santa Cruz (e.g., Santa Cruz Cat #sc-29436, 44219) and the like.

An siRNA and shRNA against human p53 can also be designed and synthesized using one of the aforementioned search software programs, by inputting the sequence of human p53 cDNA shown by SEQ ID NO:3 or Refseq. No. (NM 000546) and the like as a query, or can also be purchased from Ambion and the like. Specifically, an shRNA against human p53 having the sequence 5'-GACTCCAGTGGTAATCTACTGCTCGAGCAGTA-GATTACCACTGGAGTC-3' (SEQ ID NO: 28; the bald letters indicate the target sequence for p53; underlined are the portions where a dsRNA is formed), the shRNA against p53 described in *Science*, 296, 550-553 (2002), and the like can be mentioned.

Contact of an siRNA or shRNA against p53 with a somatic cell can be achieved by, as in the case of plasmid DNA, introducing the nucleic acid into the cell using the liposome method, polyamine method, electroporation method, beads method and the like. The method using a cationic liposome is the most common and offers high transfer efficiency. In addition to common transfection reagents such as Lipofectamine2000 and Oligofectamine (Invitrogen), for example, transfer reagents suitable for introduction of an siRNA, such as the GeneEraser™ siRNA transfection reagent (Stratagene), are also commercially available.

(b2) Vectors that Express an siRNA or shRNA Against p53

Vectors that express an siRNA are available in the tandem type and the stem loop (hairpin) type. The former is the type in which an expression cassette for a sense strand of an siRNA and an expression cassette for an antisense strand are ligated tandem, each strand being expressed in the cell and undergoing annealing to form a double-stranded siRNA (dsRNA). Meanwhile, the latter is the type in which an expression cassette for an shRNA is inserted into a vector, the shRNA being expressed in the cell and undergoing processing by a dicer to form a dsRNA. Although a polII promoter (for example, immediate-early promoter of CMV) may be used as the promoter, it is common practice to use a polIII promoter in order to allow the accurate transcription of short RNA. As the polIII promoter, mouse and human U6-snRNA promoters, human H1-RNase P RNA promoter, human valine-tRNA promoter and the like can be mentioned. As a transcription termination signal, a sequence of 4 or more T residues in succession is used.

The siRNA or shRNA expression cassette thus constructed is then inserted into a plasmid vector or a viral vector. As such vectors, the same as those described with respect to a nucleic acid that encodes a dominant negative mutant of p53 can be utilized preferably (viral vectors such as retrovirus, lentivirus, adenovirus, adeno-associated virus, herpesvirus, and Sendai virus; animal cell expression plasmids and the like). The vector used can be chosen as appropriate according to the intended use of the iPS cell obtained, as in the case of a dominant negative mutant. Alternatively, as an expression vector that encodes an shRNA against p53, a viral vector such as retrovirus, prepared on the basis of a commercially available plasmid (for example, pMKO.1-puro p53 shRNA2: #10672, commercially available from Addgene, and the like) or the like can also be used. The aforementioned Cre-loxP system or piggyBac transposon system can also be utilized as required.

Contact of a vector that expresses an siRNA or shRNA against p53 with a somatic cell is achieved by introducing a plasmid vector or viral vector prepared as described above into the cell. Transfer of these genes can be achieved by the same technique as that described with respect to a nucleic acid that encodes a dominant negative mutant of p53.

(b3) Other Substances

As other substances that inhibit the expression of the p53 gene, antisense nucleic acids against p53 and ribozymes can be mentioned.

The antisense nucleic acid may be a DNA or an RNA, or a DNA/RNA chimera. When the antisense nucleic acid is a DNA, an RNA:DNA hybrid formed by a target RNA and the antisense DNA is capable of being recognized by endogenous RNase H to cause selective degradation of the target RNA. Therefore, in the case of an antisense DNA to be degraded with RNase H, the target sequence may be not only a sequence in p53 mRNA, but also a sequence in the intron region of the primary transcript of the p53 gene. The length of the target region for the antisense nucleic acid is not particularly limited, as far as hybridization of the antisense nucleic acid results in an inhibition of the translation into the p53 protein; the target region may be the entire sequence or a partial sequence of p53 mRNA, and may be a sequence of about 15 bases for the shortest, or of the entire sequence of the mRNA or primary transcript for the longest. Considering the ease of synthesis, antigenicity, transferability in cells and other issues, an oligonucleotide consisting of about 15 to about 40 bases, particularly about 18 to about 30 bases, is preferable. Positions of the target sequence include, but are not limited to, 5'- and 3'-UTR, vicinities of the start codon and the like.

A ribozyme refers to an RNA possessing an enzyme activity to cleave a nucleic acid in the narrow sense, and is herein understood to be used as a concept encompassing a DNA, as far as the ribozyme possesses sequence-specific nucleic acid cleavage activity. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends adjoining to the hammerhead structure portion (about 10 bases in total) be a sequence complementary to the desired cleavage site of the mRNA.

An antisense nucleic acid or a ribozyme can be synthesized using an automated DNA/RNA synthesizer. The nucleotide molecules that constitute them may also have the same modifications as those for siRNA, so as to increase the stability, specific activity and the like.

Alternatively, the antisense nucleic acid or ribozyme can also be used in the form of a nucleic acid that encodes the same, as in the case of siRNA.

The aforementioned inhibitor of p53 function needs to be brought into contact with a somatic cell in a way sufficient to inhibit the p53 function in the step of somatic cell nuclear reprogramming. Here, nuclear reprogramming of the somatic cell can be achieved by bringing a nuclear reprogramming substance into contact with the somatic cell.

(c) Nuclear Reprogramming Substances

In the present invention, "a nuclear reprogramming substance" refers to any substance capable of inducing an iPS cell from a somatic cell, such as a proteinous factor or a nucleic acid that encodes the same (including forms incorporated in a vector), or a low-molecular compound. When the nuclear reprogramming substance is a proteinous factor or a nucleic acid that encodes the same, the following combinations can be mentioned as preferable examples (hereinafter, only the names for proteinous factors are shown).

(1) Oct3/4, Klf4, c-Myc
(2) Oct3/4, Klf4, c-Myc, Sox2 (here, Sox2 is replaceable with Sox1, Sox3, Sox15, Sox17 or Sox18. Also, Klf4 is replaceable with Klf1, Klf2 or Klf5. Furthermore, c-Myc is replaceable with T58A (active mutant), N-Myc, L-Myc.)
(3) Oct3/4, Klf4, c-Myc, Sox2, Fbx15, Nanog, Eras, ECAT15-2, TclI, β-catenin (active mutant S33Y)
(4) Oct3/4, Klf4, c-Myc, Sox2, TERT, SV40 Large T
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmi1
(for all above, see WO 2007/069666 (however, in the combination (2) above, for replacement of Sox2 with Sox18, and replacement of Klf4 with Klf1 or Klf5, see Nature Biotechnology, 26, 101-106 (2008)). For combinations of "Oct3/4, Klf4, c-Myc, Sox2", see also *Cell*, 126, 663-676 (2006), Cell, 131, 861-872 (2007) and the like. For combinations of "Oct3/4, Klf2 (or Klf5), c-Myc, Sox2", see also *Nat. Cell Biol.*, 11, 197-203 (2009). For combinations of "Oct3/4, Klf4, c-Myc, Sox2, hTERT, SV40 Large T", see also Nature, 451, 141-146 (2008).) (9) Oct3/4, Klf4, Sox2 (see *Nature Biotechnology*, 26, 101-106 (2008)) (10) Oct3/4, Sox2, Nanog, Lin28 (see *Science*, 318, 1917-1920 (2007)) (11) Oct3/4, Sox2, Nanog, Lin28, hTERT, SV40 Large T (see *Stem Cells*, 26, 1998-2005 (2008))
(12) Oct3/4, Klf4, c-Myc, Sox2, Nanog, Lin28 (see *Cell Research*(2008) 600-603)
(13) Oct3/4, Klf4, c-Myc, Sox2, SV40 Large T (see also *Stem Cells*, 26, 1998-2005 (2008))
(14) Oct3/4, Klf4 (see *Nature* 454:646-650 (2008), Cell Stem Cell, 2:525-528(2008)))
(15) Oct3/4, c-Myc (see *Nature* 454:646-650 (2008))
(16) Oct3/4, Sox2 (see Nature, 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (here, Esrrb is replaceable with Esrrg; see *Nat. Cell Biol.*, 11, 197-203 (2009))
(20) Oct3/4, Sox2, Esrrb (see *Nat. Cell Biol.*, 11, 197-203 (2009))
(21) Oct3/4, Klf4, L-Myc
(22) Oct3/4, Nanog
(23) Oct3/4
(24) Oct3/4, Klf4, c-Myc, Sox2, Nanog, Lin28, SV40LT (see *Science*, 324: 797-801 (2009))

In (1)-(24) above, in place of Oct3/4, other members of the Oct family, for example, Oct1A, Oct6 and the like, can also be used. In place of Sox2 (or Sox1, Sox3, Sox15, Sox17, Sox18), other members of the Sox family, for example, Sox7 and the like, can also be used. In place of c-Myc, other members of the Myc family, for example, L-Myc and the like, can also be used. In place of Lin28, other members of the Lin family, for example, Lin28b and the like, can also be used.

A combination that does not fall in (1)-(24) above, but contains all the constituents in any one thereof and further comprises an optionally chosen other substance, can also be included in the scope of "nuclear reprogramming substances" in the present invention. Under conditions wherein the somatic being the subject of nuclear reprogramming is endogenously expressing one or more of the constituents in any one of (1)-(24) above at a level sufficient to secure nuclear reprogramming, a combination of the remaining constituents excluding the one or more constituents can also be included in the scope of "nuclear reprogramming substances" in the present invention.

Among these combinations, as examples of preferable nuclear reprogramming substances, at least one, preferably two or more, more preferably 3 or more selected from Oct3/4, Sox2, Klf4, c-Myc, Nanog, Lin28 and SV40LT can be mentioned.

With the use of the iPS cells obtained for therapeutic purposes in mind, of these combinations, the combination of the 3 factors Oct3/4, Sox2 and Klf4 (that is, (9) above) is preferable. In the method of the present invention, with the aforementioned 3 factors only, iPS cells can be obtained at sufficiently high efficiency. That is, even with the 3 factors only, iPS cells can be established at an efficiency closer to the efficiency with 4 factors (Oct3/4, Sox2, Klf4 and c-Myc). Meanwhile, when the use of the iPS cells for therapeutic purposes is not in mind (for example, used as an investigational tool for drug discovery screening and the like), as well as the aforementioned 4 factors, the 5 factors Oct3/4, Klf4, c-Myc, Sox2 and Lin28, or the 6 factors including the 5 factors plus Nanog (that is, (12) above), are preferable. In these preferred combinations, L-Myc can also be used in place of c-Myc.

Mouse and human cDNA sequence information on the aforementioned proteinous factors can be acquired by referring to the NCBI accession numbers mentioned in WO 2007/069666 (in the publication, Nanog is mentioned with the designation "ECAT4"; mouse and human cDNA sequence information on Lin28, Lin28b, Esrrb, and Esrrg can be acquired by referring to the following NCBI accession numbers, respectively); those skilled in the art are easily able to isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

When a proteinous factor itself is used as a nuclear reprogramming substance, the factor can be prepared by inserting the cDNA obtained into an appropriate expression vector, introducing the vector into a host cell, culturing the cell, and recovering the recombinant proteinous factor from the culture obtained. Meanwhile, when a nucleic acid that encodes a proteinous factor is used as a nuclear reprogramming substance, the cDNA obtained is inserted into a viral vector or a plasmid vector to construct an expression vector as in the aforementioned case of a nucleic acid that encodes a dominant negative mutant of p53, and the vector is subjected to the step of nuclear reprogramming. The aforementioned Cre-loxP system or piggyBac transposon system can be utilized as required. When nucleic acids that encode 2 or more proteinous factors are introduced into a cell as nuclear reprogramming substances, the nucleic acids may be carried by separate vectors, and a plurality of nucleic acids may be joined tandem to obtain a polycistronic vector. In the latter case, to enable efficient polycistronic expression, it is desirable that the 2A self-cleaving peptide of foot-and-mouth disease virus (see *Science*, 322, 949-953, 2008 and the like), IRES sequence and the like, preferably the 2A sequence be ligated between the individual nucleic acids.

When p53 function is inhibited, transgenes integrated into chromosomes via retroviral or lentiviral vectors tend to resistant to gene silencing. Therefore, use of a plasmid vector is advantageous for preventing unnecessary persistent expression of exogenous nuclear reprogramming substances.

Contact of a nuclear reprogramming substance with a somatic cell can be achieved as with the aforementioned dominant negative mutant of p53 (a) when the substance is a proteinous factor; as with the aforementioned nucleic acid that encodes a dominant negative mutant of p53 (b) when the substance is a nucleic acid that encodes the proteinous factor (a); and as with the aforementioned chemical inhibitor of p53 (c) when the substance is a low-molecular compound.

As described above, an inhibitor of p53 function needs to be brought into contact with a somatic cell in a way sufficient to inhibit the p53 function in the step of somatic cell nuclear reprogramming. As far as this requirement is met, the nuclear reprogramming substance and the inhibitor of p53 function may be brought into contact with the somatic cell simultaneously, or either one may be brought into contact in advance. In a mode of embodiment, for example, when the nuclear reprogramming substance is a nucleic acid that encodes a proteinous factor, and the inhibitor of p53 function is a chemical inhibitor, the former involves a given length of time lag from the transfection treatment to the mass-expression of the proteinous factor, whereas the latter is capable of rapidly inhibiting the p53 function, so that after the cell is cultured for a given length of time after the transfection treatment, the chemical inhibitor of p53 can be added to the medium. In another mode of embodiment, for example, when the nuclear reprogramming substance and the inhibitor of p53 function are used in the form of viral vectors or plasmid vectors, both may be simultaneously introduced into the cell.

The number of repeats of the manipulation to introduce an adenoviral or non-viral expression vector into a somatic cell is not particularly limited, the transfection can be performed once or more optionally chosen times (e.g., once to 10 times, once to 5 times or the like). When two or more kinds of adenoviral or non-viral expression vectors are introduced into a somatic cell, it is preferable that these all kinds of adenoviral or non-viral expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

(d) iPS Cell Establishment Efficiency Improvers

By bringing, in addition to an inhibitor of p53 function, another publicly known iPS cell establishment efficiency improver, into contact with a somatic cell, the efficiency of establishment of iPS cells is expected to be increased more. Examples of iPS cell establishment efficiency improvers include, but are not limited to, histone deacetylase (HDAC) inhibitors [e.g., valproic acid (VPA) (*Nat. Biotechnol.*, 26(7): 795-797 (2008)), low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC 1 (OriGene) and the like), and the like], G9a histone methyltransferase inhibitors [for example, low-molecular inhibitors such as BIX-01294 (*Cell Stem Cell*, 2: 525-528 (2008)), nucleic acid-based expression inhibitors such as siRNAs and shRNAs against G9a (e.g., G9a siRNA (human) (Santa Cruz Biotechnology) and the like) and the like], L-channel calcium agonists (for example, Bayk8644) (Cell Stem Cell, 3, 568-574 (2008)), UTF1 (Cell Stem Cell, 3, 475-479 (2008)), Wnt Signaling (for example, soluble Wnt3a) (Cell Stem Cell, 3, 132-135 (2008)), 2i/LIF (2i is an inhibitor of mitogen-activated protein kinase signaling and glycogen synthase kinase-3, PloS Biology, 6(10), 2237-2247 (2008)) and the like, and the like. As mentioned above, the nucleic acid-based expression inhibitors may be in the form of expression vectors harboring a DNA that encodes an siRNA or shRNA.

Of the aforementioned constituents of nuclear reprogramming substances, SV40 large T, for example, can also be included in the scope of iPS cell establishment efficiency improvers because they are auxiliary factors unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances, or deemed iPS cell establishment efficiency improvers. Hence, because the somatic cell nuclear reprogramming process is visualized as an overall event resulting from contact of nuclear reprogramming substances and an iPS cell establishment efficiency improver with somatic cells, it does not always seem necessary for those skilled in the art to distinguish both.

Contact of these other iPS cell establishment efficiency improvers with a somatic cell can be achieved as described above with respect to functional inhibitors of p53, respectively, when the improver is (a) a proteinous factor, (b) a nucleic acid that encodes the proteinous factor, or (c) a low-molecular compound.

(e) Source of Somatic Cells

The somatic cells that can be used as a starting material for the preparation of iPS cells in the present invention may be any cells, other than germ cells, derived from a mammal (for example, mouse or human); for example, keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), and progenitor cells thereof (tissue progenitor cells) and the like can be mentioned. There is no limitation on the degree of cell differentiation; even undifferentiated progenitor cells (including somatic stem cells) and finally differentiated mature cells can be used alike as a source of somatic cells in the present invention. Here, as examples of undifferentiated progenitor cells, tissue stem cells (somatic stem cells) such as nerve stem cells, hematopoietic stem cells, mesenchymal stem cells, and dental pulp stem cells can be mentioned.

According to the method of the present invention, iPS cells can be efficiently obtained even from finally differentiated somatic cells, for which iPS cells are reportedly generally difficult to establish. In a preferred mode of embodiment of the present invention, a T cell is used as a somatic cell. The T cell may be CD4-positive or CD8-positive, and may be a cell in a CD4/CD8 double-positive differentiation stage. T cells can be isolated from the spleen, lymph node, peripheral blood, cord blood and the like by a method known per se, for example flow cytometry using an antibody against a cell surface marker such as CD4, CD8, or CD3, and a cell sorter. In the case of mice, it is preferable that a somatic cell be collected from the spleen or lymph node, in which the content ratio of T cells is high; however, in the case of humans, it is desirable, from the viewpoint of the low invasiveness and the ease of preparation, that a T cell be prepared from peripheral blood, cord blood or the like.

The choice of mammal serving as a source of somatic cells collected is not particularly limited; however, when the iPS cells obtained are used for regenerative medicine in humans, it is particularly preferable, from the viewpoint of non-occurrence of graft rejection, that a somatic cell be collected from a patient or another person of the same HLA type. When the IPS cells are not administered (transplanted) to a human, but used as, for example, a source of cells for screening for evaluating a patient's drug susceptibility or the presence or absence of an adverse reaction, it is likewise necessary to collect a somatic cell from a patient or another person with the same genetic polymorphism correlating to the drug susceptibility or adverse reaction.

Somatic cells separated from a mouse or a human can be pre-cultured using a medium known per se suitable for the cultivation thereof depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium and the like. Reports are available that by conducting pre-culture at a low serum concentration of 5% or less, the efficiency of establishment of iPS cells was improved (for example, WO 2009/006997). When a T cell is used as the somatic cell, it is desirable that the cell be pre-cultured using a medium containing a cytokine such as interleukin (IL)-2, IL-7, stem cell factor (SCF), or Flt3 ligand. When using, for example, a transfection reagent such as a cationic liposome in the contact with a nuclear reprogramming substance and an inhibitor of p53 function (and another substance that improves the efficiency of establishment of iPS cells), it is sometimes preferable that the medium be previously replaced with a serum-free medium to prevent a reduction in the transfer efficiency. After the nuclear reprogramming substance is brought into contact, the cell can be cultured under conditions suitable for cultivation of, for example, ES cells. In the case of mouse cells, it is preferable that the culture be carried out with the addition of Leukemia Inhibitory Factor (LIF) as a differentiation suppression factor to an ordinary medium. Meanwhile, in the case of human cells, it is desirable that basic fibroblast growth factor (bFGF) and/or stem cell factor (SCF) be added in place of LIF. Usually, the cell is cultured in the co-presence of fetal-mouse-derived fibroblasts (MEF) treated with radiation or an antibiotic to terminate the cell division, as feeder cells. As the MEF, usually STO cells and the like are commonly used, but for inducing iPS cells, SNL cells (McMahon, A. P. & Bradley, A. Cell 62, 1073-1085 (1990)) and the like are commonly used. Co-culture with feeder cells may be started before contact of the nuclear reprogramming substance, at the time of the contact, or after the contact (for example, 1-10 days later).

A candidate colony of iPS cells can be selected by a method with drug resistance and reporter activity as indicators, and also by a method based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (for example, Fbx15, Nanog, Oct3/4 and the like, preferably Nanog or Oct3/4). As examples of such recombinant cells, a mouse-derived MEF wherein the βgeo (which encodes a fusion protein of β-galactosidase and neomycin phosphotransferase) gene is knocked-in to the Fbx15 gene locus (Takahashi & Yamanaka, Cell, 126, 663-676 (2006)), or a transgenic mouse-derived MEF wherein green the fluorescent protein (GFP) gene and the puromycin resistance gene are integrated in the Nanog gene locus (Okita et al., Nature, 448, 313-317 (2007)) and the like can be mentioned. Meanwhile, methods of macroscopic examination of morphology include, for example, the method described by Takahashi et al. in Cell, 131, 861-872 (2007). Although methods using reporter cells are convenient and efficient, colony selection by macroscopic examination is desirable from the viewpoint of safety when iPS cells are prepared for the purpose of human treatment. When the 3 factors Oct3/4, Klf4 and Sox2 are used as nuclear reprogramming substances, the number of clones established sometimes decreases, but the resulting colonies are for the most part iPS cells whose quality is as high as that of ES cells; therefore, it is possible to efficiently establish iPS cells even without using reporter cells.

The identity of the cells of the selected colony as iPS cells can be confirmed by positive responses to Nanog (or Oct3/4, Fbx15) reporters (GFP positivity, β-galactosidase positivity and the like) and positive responses to selection markers (puromycin resistance, G418 resistance and the like), as well as by the formation of a visible ES cell-like colony, as described above; however, to increase the accuracy, it is possible to perform tests such as analyzing the expression of various ES-cell-specific genes, and transplanting the cells selected to a mouse and confirming teratoma formation. These test methods are obvious to those skilled in the art, representative confirmatory tests being described in Examples below.

The iPS cells thus established can be used for various purposes. For example, by utilizing a method of differentiation induction reported with respect to ES cells, differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

When inhibition of p53 is achieved in a mode wherein a dominant negative mutant of p53 or a nucleic acid that encodes an siRNA or shRNA against p53 or the like is introduced into a somatic cell and forcibly expressed therein, the iPS cell obtained is a novel cell distinct from conventionally known iPS cells because of the containment of the exogenous nucleic acid. In particular, when the exogenous nucleic acid is introduced into the somatic cell using a retrovirus, lentivirus or the like, the exogenous nucleic acid is usually integrated in the genome of the iPS cell obtained, so that the phenotype of containing the exogenous nucleic acid is stably retained. When the exogenous nucleic acid is introduced into the somatic cell using a persistent Sendai viral vector, the exogenous nucleic acid can occur stably in the cytoplasm of the iPS cell obtained, so that the phenotype of containing the exogenous nucleic acid is likewise stably retained.

The present invention also provides an iPS cell wherein the TCR gene has been rearranged, the cell obtained by reprogramming a T cell. As a method of T cell reprogramming, a method wherein a T cell is brought into contact with a nuclear reprogramming substance under conditions for inhibiting the p53 function as described above can be mentioned. In the iPS cell induced from a T cell (T-iPS cell), the TCR rearrangement in the T cell from which it is derived is conserved. Although there have been some cases where iPS cells were induced from B cells so far, no report has been presented regarding the establishment of iPS cells derived from a T cell. Because the rearrangement of TCR is conserved even in the cells differentiated from a T-iPS cell, T cells capable of specifically injuring cells that present one of the above-described peptides (e.g., cancer cells, infected cells and the like) can be produced in large amounts by, for example, establishing a T-iPS cell from a T cell clone capable of specifically recognizing antigen-presenting cells (e.g., macrophages, dendritic cells and the like) pulsated with a cancer antigen peptide or with a peptide derived from a cell surface antigen of a pathogen such as a virus, amplifying the iPS cell to large amounts in vitro using the method of the present invention, then inducing their differentiation into T cells, and can be prepared as a T cell immunotherapeutic agent as with conventional T cell immunotherapy.

The present invention is explained in more detail in the following by referring to Examples, which are not to be construed as limitative.

EXAMPLES

Example 1: Effects of p53 Deficiency

A p53 homo-deficient mouse or hetero-deficient mouse having a Nanog reporter was used as an experimental system. p53 is a gene that is expressed in almost all cells and controls cell cycle termination or apoptosis induction during repair of damaged cells. These mice have been deprived of the function of the p53 gene by replacing the exon 5 with the neomycin resistance gene (Lawrence A. Donehower (1992). Nature 356, 215-221). It has been reported that p53 homo-deficient mice are born normally but frequently suffer from tumorigenesis. The Nanog reporter was prepared by inserting green fluorescent protein (EGFP) and the puromycin resistance gene into the Nanog locus of a BAC (bacterial artificial chromosome) purchased from BACPAC Resources (Okita K. et al., Nature 448, 313-317(2007)). The mouse Nanog gene is a gene expressed specifically in pluripotent cells such as ES cells and early embryos. The mouse iPS cells that have become positive for this reporter are known to have a potential for differentiation nearly equivalent to that of ES cells. By preparing a Nanog reporter mouse having this Nanog reporter (Okita K. et al., Nature 448, 313-317(2007)), and mating this mouse with p53 deficient mice, p53 homo-deficient mice and hetero-deficient mice having the Nanog reporter were prepared.

The retroviruses used for reprogramming were prepared by introducing respective retrovirus expression vectors (pMXs-Oct3/4, pMXs-Sox2, pMXs-Klf4, pMXs-cMyc: Cell, 126, 663-676 (2006)) into Plat-E cells (Morita, S. et al., Gene Ther. 7, 1063-1066) that had been sown to 6-well culture plates (Falcon) at $0.6 \times 10^6$ cells per well on the day before. The culture broth used was DMEM/10% FCS (DMEM (Nacalai tesque) supplemented with 10% fetal bovine serum), and the cells were cultured at 37° C. and 5% $CO_2$. For vector transfer, 4.5 µL of the FuGene6 transfection reagent (Roche) was placed in 100 µL of Opti-MEM I Reduced-Serum Medium (Invitrogen), and this mixture was allowed to stand at room temperature for 5 minutes. Thereafter, 1.5 µg of each expression vector was added, and the mixture was further allowed to stand at room temperature for 15 minutes, and then added to the Plat-E culture broth. On day 2, the Plat-E supernatant was replaced with a fresh supply of the medium; on day 3, the culture supernatant was recovered and filtered through a 0.45 µm sterile filter (Whatman), polybrene (Nacalai) was added to obtain a concentration of 4 µg/mL, and this was used as the viral liquid.

Fibroblasts (MEFs) were isolated from a fetal p53 homo-deficient mouse having the mouse Nanog reporter (13.5 days after fertilization). Because of the absence of expression of the Nanog gene, MEFs do not express EGFP and do not emit green fluorescence. Because of the absence of expression of the puromycin resistance gene as well, MEFs are susceptible to puromycin, an antibiotic. As such, the MEFs were sown to a 6-well culture plate (Falcon) coated with 0.1% gelatin (Sigma) at $1 \times 10^5$ per well. The culture broth used was DMEM/10% FCS, and the cells were cultured at 37° C. and 5% $CO_2$. The following day, the retrovirus liquid was added to cause overnight infection to introduce the gene.

Starting on day 3 after the viral infection, the cells were cultured using an LIF-supplemented ES cell culture medium (one prepared by adding to DMEM (Nacarai tesque) 15% fetal bovine serum, 2 mM L-glutamine (Invitrogen), 100 µM non-essential amino acids (Invitrogen), 100 µM 2-mercaptoethanol (Invitrogen), 50 U/mL penicillin (Invitrogen) and 50 µg/mL streptomycin (Invitrogen)). On day 5 after the infection, the medium for the MEFs was removed, and the cells were washed by the addition of 1 mL of PBS. After the PBS was removed, 0.25% Trypsin/1 mM EDTA (Invitrogen) was added, and a reaction was allowed to proceed at 37° C. for about 5 minutes. After the cells floated up, the cells were suspended by the addition of ES cell culture medium, and $5 \times 10^1$ cells were sown to a 100-mm dish with feeder cells sown thereto previously. The feeder cells used were SNL cells that had been treated with mitomycin C to terminate the cell division (McMahon, A. P. & Bradley, A. Cell 62, 1073-1085 (1990)). Subsequently, the ES cell culture medium was exchanged with a fresh supply every two days until a colony was observable. Selection with puromycin (1.5 µg/mL) was performed, starting on day 13 for the cells infected with 4 factors (Oct3/4, Sox2, Klf4, c-Myc), and on day 19 for the cells infected with 3 factors (Oct3/4, Sox2, Klf4). Colonies were visible about on day 10 for the 4 factors, and about on day 20 for the 3 factors, and became GFP-positive gradually.

Figure 1B:
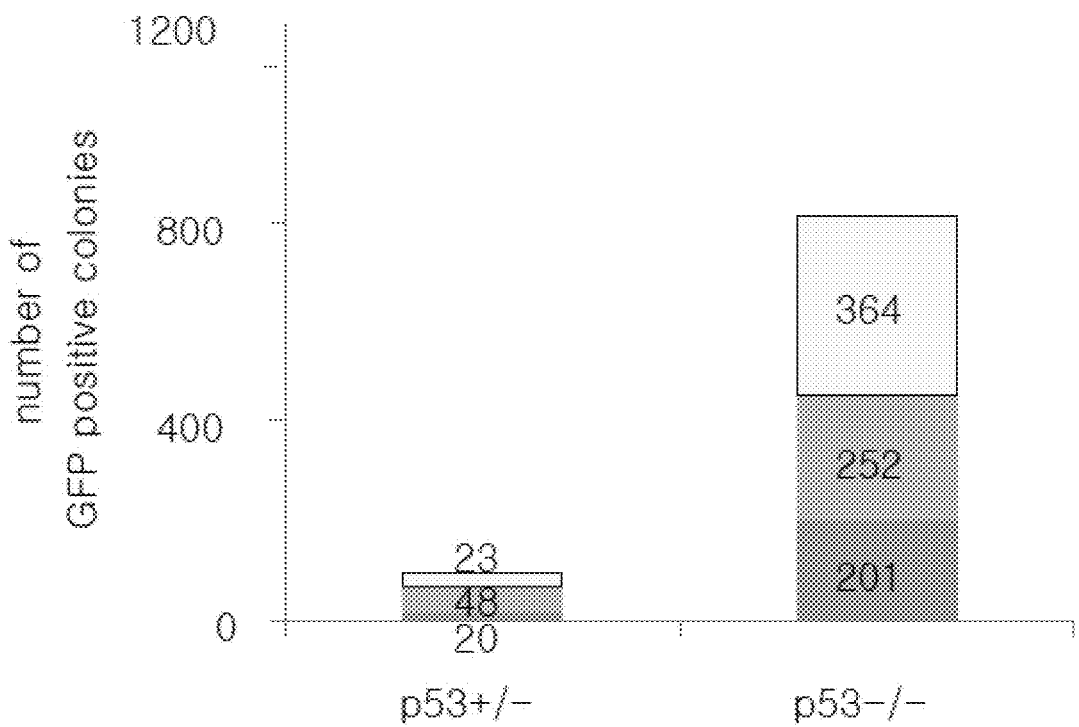

GFP-positive colonies were counted on day 21 for the 4 factors, and on day 28 for the 3 factors. The total results of three experiments are shown in FIGS. 1A-1B. Compared with the p53 hetero-deficient cells constituting the control group, in the p53 homo-deficient cells, GFP-positive colonies increased about 2 times for the 4 factors, and about 9 times for the 3 factors.

Figure 2:
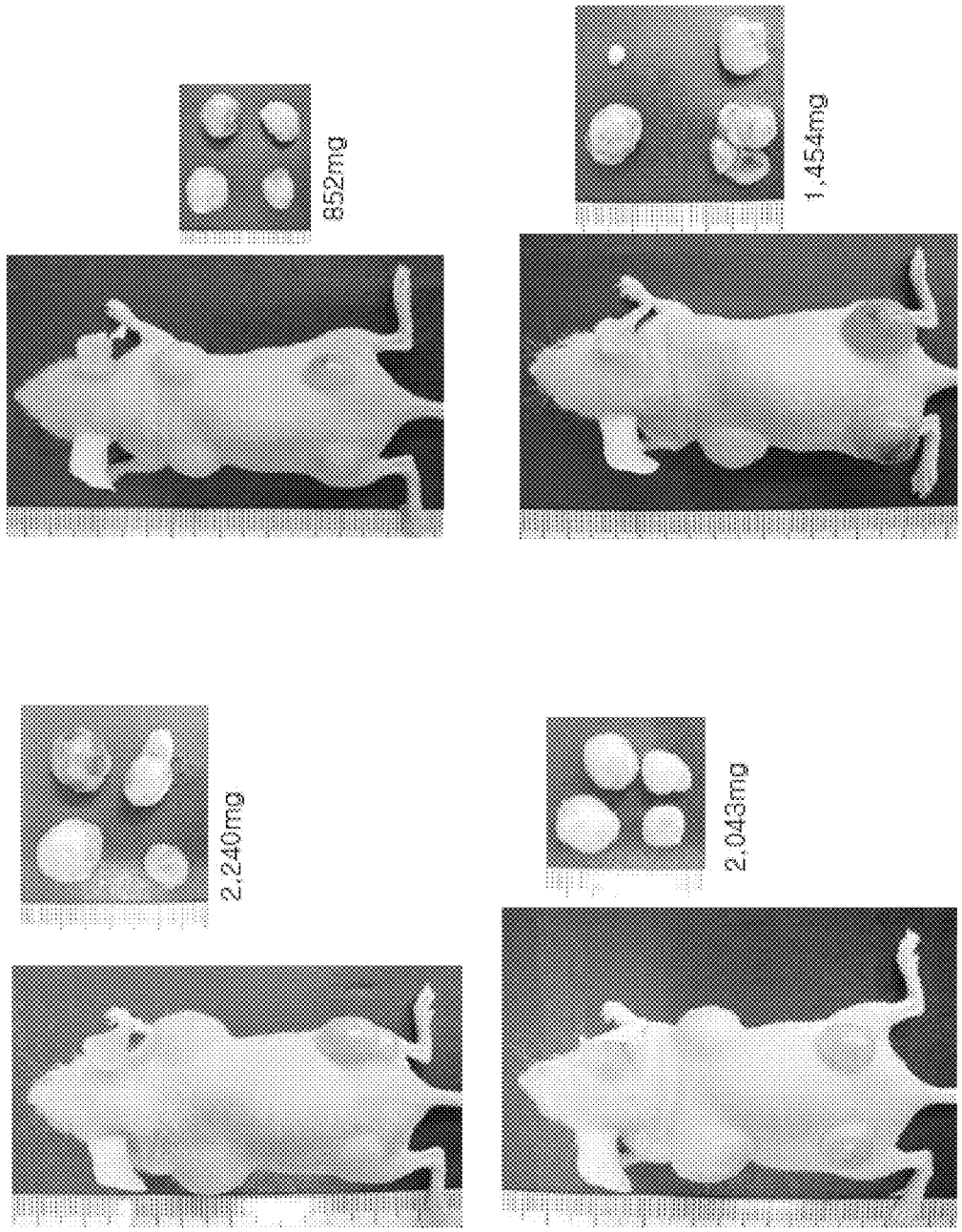
FIG. 2 is a photograph showing that a GFP-positive colony resulting from p53-homo-deficient cells infected with 4 factors (Oct3/4, Sox2, Klf4, c-Myc) was subcutaneously injected to an immunodeficient mouse, and that teratomas were formed.

Next, GFP-positive colonies were collected on day 21 for the 4 factors, and on day 28 for the 3 factors, and, after trypsinization, the cultivation was continued on the feeder cells (this time point was taken as subculture generation 1). When $1 \times 10^6$ cells were subcutaneously injected to immunodeficient mice, teratoma formation began to be observable 2 weeks later; whether the 3 factors or the 4 factors were introduced, the resulting GFP-positive colonies were identified as iPS cells. The results for the 4 factors are shown in FIG. 2.

From the results above, it was demonstrated that by deleting (knock-outing) p53, the efficiency of establishment of iPS cells was increased.

Example 2: Investigation with a Dominant Negative Mutant

The function of endogenous p53 was inhibited using a dominant negative mutant of p53, and its influence on the efficiency of establishment of iPS cells was investigated. The dominant negative mutant used was p53P275S, prepared by causing a point mutation of the proline at the position 275 located in the genome-binding region of p53 to serine (Annemieke de Vries (2002). *PNAS* 99, 2948-2953).

The retrovirus used for reprogramming was prepared by introducing retrovirus expression vector (pMXs-Oct3/4, pMXs-Sox2, pMXs-Klf4, pMXs-cMyc, pMXs-p53P275S) into Plat-E cells that had been sown to a 6-well culture plate (Falcon) at $0.6 \times 10^6$ cells per well on the previous day (for how to prepare pMXs-p53P275S, see Example 6 below). The culture broth used was DMEM/10% FCS (DMEM (Nacalai tesque) supplemented with 10% fetal bovine serum), and cultured at 37° C. and 5% $CO_2$. For vector transfer, 4.5 µL of the FuGene6 transfection reagent (Roche) was placed in 100 µL of Opti-MEM I Reduced-Serum Medium (Invitrogen), and this mixture was allowed to stand at room temperature for 5 minutes. Thereafter, 1.5 µg of each expression vector was added, and the mixture was further allowed to stand at room temperature for 15 minutes, and then added to Plat-E culture broth. On day 2, the Plat-E supernatant was exchanged with a fresh supply of the medium; on day 3, the culture supernatant was recovered and filtered through a 0.45 µm sterile filter (Whatman), polybrene (Nacalai) was added to obtain a concentration of 4 µg/mL, and this was used as the viral liquid.

Fibroblasts (MEFs) were isolated from a fetal p53 hetero-deficient mouse having a Nanog reporter (13.5 days after fertilization). A 6-well culture plate with feeder cells sown thereto previously was provided, and MEFs were sown at $4 \times 10^3$ cells per well for the 4 factors, and at $2 \times 10^4$ cells per well for the 3 factors. The feeder cells used were SNL cells that had been treated with mitomycin C to terminate the cell division. The culture broth used was DMEM/10% FCS, and were cultured at 37° C. and 5% $CO_2$. The following day, the cells were cultured in a viral liquid recovered from Plat-E overnight to introduce the gene. Starting on day 3 after the infection, the cells were cultured using an LIF-supplemented ES cell culture medium. Subsequently, the ES cell culture medium was exchanged with a fresh supply every two days until a colony was visible. Selection with puromycin (1.5 µg/mL) was performed starting on day 13 after the infection for the cells infected with both 4 factors (Oct3/4, Sox2, Klf4, c-Myc) and P275S, and on day 19 for the cells infected with both 3 factors (Oct3/4, Sox2, Klf4) and P275S. Colonies were visible about on day 10 for the 4 factors, and about on day for the 3 factors, and became GFP-positive gradually.

GFP-positive colonies were counted on day 21 for the 4 factors, and on day 28 for the 3 factors. An outline of the experimental procedure is shown in FIG. 3A, and experimental results are shown in FIGS. 3B-3D. Compared with the cells incorporating mutation-free p53 or red fluorescent protein (DsRedExpress) in place of p53P275S, in the cells incorporating P275S, the number of GFP-positive colonies increased about 4 times for the 4 factors, and about 3 times for the 3 factors.

The results for introduction of both the above-described 3 factors or 4 factors and p53 or DsRedExpress into the MEFs isolated from a fetal p53 homo-deficient mouse are shown in FIGS. 3E-3G. Compared with the cells incorporating the control DsRedExpress, in the cells incorporating p53, the number of GFP-positive colonies decreased.

From the results above, it was demonstrated that by inhibiting the function of endogenous p53, the efficiency of establishment of iPS cells was increased.

Example 3: Investigation Using p53 Inhibitory Agent

The effects of a p53 inhibitor on the efficiency of establishment of iPS cells were examined. The retrovirus used for reprogramming was prepared by introducing a retrovirus expression vector (pMXs-Oct3/4, pMXs-Sox2, pMXs-Klf4, pMXs-cMyc) into Plat-E cells that had been sown to a 6-well culture plate (Falcon) at $0.6 \times 10^6$ cells per well on the previous day. The culture broth used was DMEM/10% FCS (DMEM (Nacalai tesque) supplemented with 10% fetal bovine serum), and cultured at 37° C. and 5% $CO_2$. For vector transfer, 4.5 µL of the FuGene6 transfection reagent (Roche) was placed in 100 µL of Opti-MEM I Reduced-Serum Medium (Invitrogen), and this mixture was allowed to stand at room temperature for 5 minutes. Thereafter, 1.5 µg of each expression vector was added, and the mixture was further allowed to stand at room temperature for 15 minutes, and then added to Plat-E culture broth. On day 2, the Plat-E supernatant was exchanged with a fresh supply of the medium; on day 3, the culture supernatant was recovered and filtered through a 0.45 µm sterile filter (Whatman), polybrene (Nacalai) was added to obtain a concentration of 4 µg/mL, and this was used as the viral liquid.

Figure 4A:
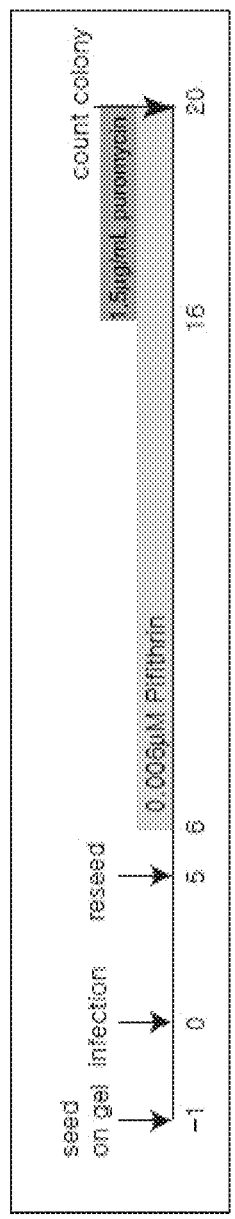
FIGS. 4A-4B show results of an examination of effects of treatment with Pifithrin, a p53 inhibitor, on the establishment of iPS cells.
Figure 4B:
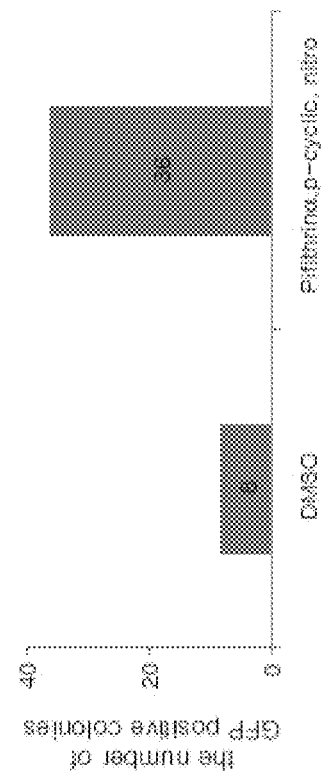

Fibroblasts (MEF) were isolated from a fetal p53 hetero-deficient mouse having the Nanog reporter (13.5 days after fertilization). These MEFs were sown to a 6-well culture plate (Falcon) coated with 0.1% gelatin (Sigma) at $1 \times 10^5$ cells per well. The culture broth used was DMEM/10% FCS, and the cells were cultured at 37° C. and 5% $CO_2$. The following day, the cells were infected with the viral liquid recovered from Plat-E overnight to introduce the gene. Starting on day 3 after the infection, the cells were cultured using an LIF-supplemented ES cell culture medium. On day 5 after the infection, the medium for MEF was removed, and the cells were washed by the addition of 1 mL of PBS. After the PBS was removed, 0.25% Trypsin/1 mM EDTA (Invitrogen) was added, and a reaction was allowed to proceed at 37° C. for about 5 minutes. After the cells floated up, the cells were suspended by the addition of ES cell culture medium, and $8 \times 10^2$ cells were sown to a 6-well culture plate with feeder cells sown thereto previously. Starting on day 6, Pifithrin α, p-Nitro, Cyclic (MERCK), 6 nM, was added to the medium, and the cultivation was continued. Pifithrin was used in solution in DMSO. Starting on day 16 after the infection, selection with puromycin (1.5 µg/mL) was performed. Colonies were visible on day 10, and became GFP-positive gradually. GFP-positive colonies were counted on day 20. The results are shown in FIGS. 4A-4B. Compared with the cells treated with DMSO, in the cells treated with Pifithrin, the number of GFP-positive colonies increased about 4 times. From the results above, it was demonstrated that by inhibiting the p53 function, the efficiency of establishment of iPS cells was increased.

Example 4: Effects of p53 Deficiency in Establishment of iPS from T Cell

A Nanog reporter mouse (hereinafter, Nanog-GFP Tg mouse: 17-week-old male) and a p53 homo-deficient mouse having a Nanog reporter (hereinafter, Nanog-GFP/Trp53$^{-/-}$ mouse: 24-week-old female) were euthanized, after which the spleens were extirpated. After the tissue was mechanically ground, CD90-positive cells were obtained using CD90 microbeads (Miltenyi biotec) and the MACS system. $1\times10^6$ cells were suspended in T cell culture medium (DMEM, 10% FBS, 10 μl/$1\times10^6$ cells CD3/CD28 T cell expander (Invitrogen), 10 units/ml IL-2) and sown to a 24-well plate coated with retronectin (50 μg/ml, Takara) ($1\times10^6$ cells/well).

The following day, the medium was replaced with 1 ml of a medium containing a retrovirus harboring 4 factors (Oct3/4, Sox2, Klf4, c-Myc) (prepared in the same manner as Example 1, virus-containing supernatant supplemented with 8 μg/ml polybrene and 10 units/ml IL-2), centrifugation was performed at 3000 rpm for 30 minutes (spin infection method), and the cells were cultured at 37° C. overnight. The following day, the medium was exchanged with a T cell culture medium, and thereafter medium exchange was performed every two days.

On day 12 after the establishment of T cells, the cells were re-sown onto mitomycin-treated SNL-PH cells ($5\times10^4$ cells/100-mm dish). Starting on the following day, the cells were cultured with an ES medium supplemented with 1.5 μg/ml puromycin.

Figure 5:
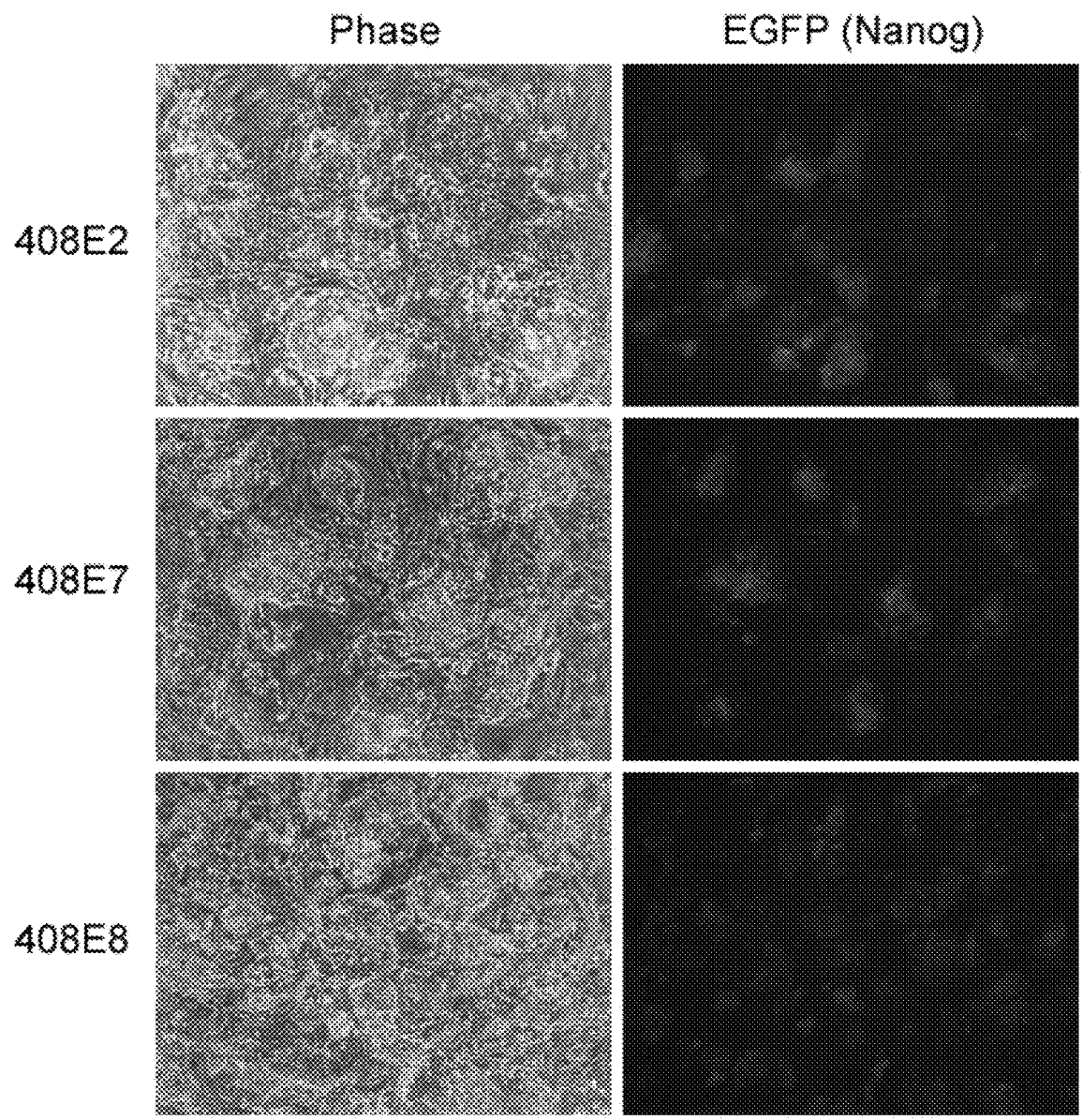
FIG. 5 is a photographic representation showing that ES-like cells resulting from T cells derived from a Nanog-GFP/Trp53$^{-/-}$ mouse infected with 4 factors (Oct3/4, Sox2, Klf4, c-Myc) are GFP-positive. Left panel: phase-contrast image, right panel: GFP-positive colony image. In the figure, 408E2, 408E7, and 408E8 indicate clone numbers.
Figure 6:
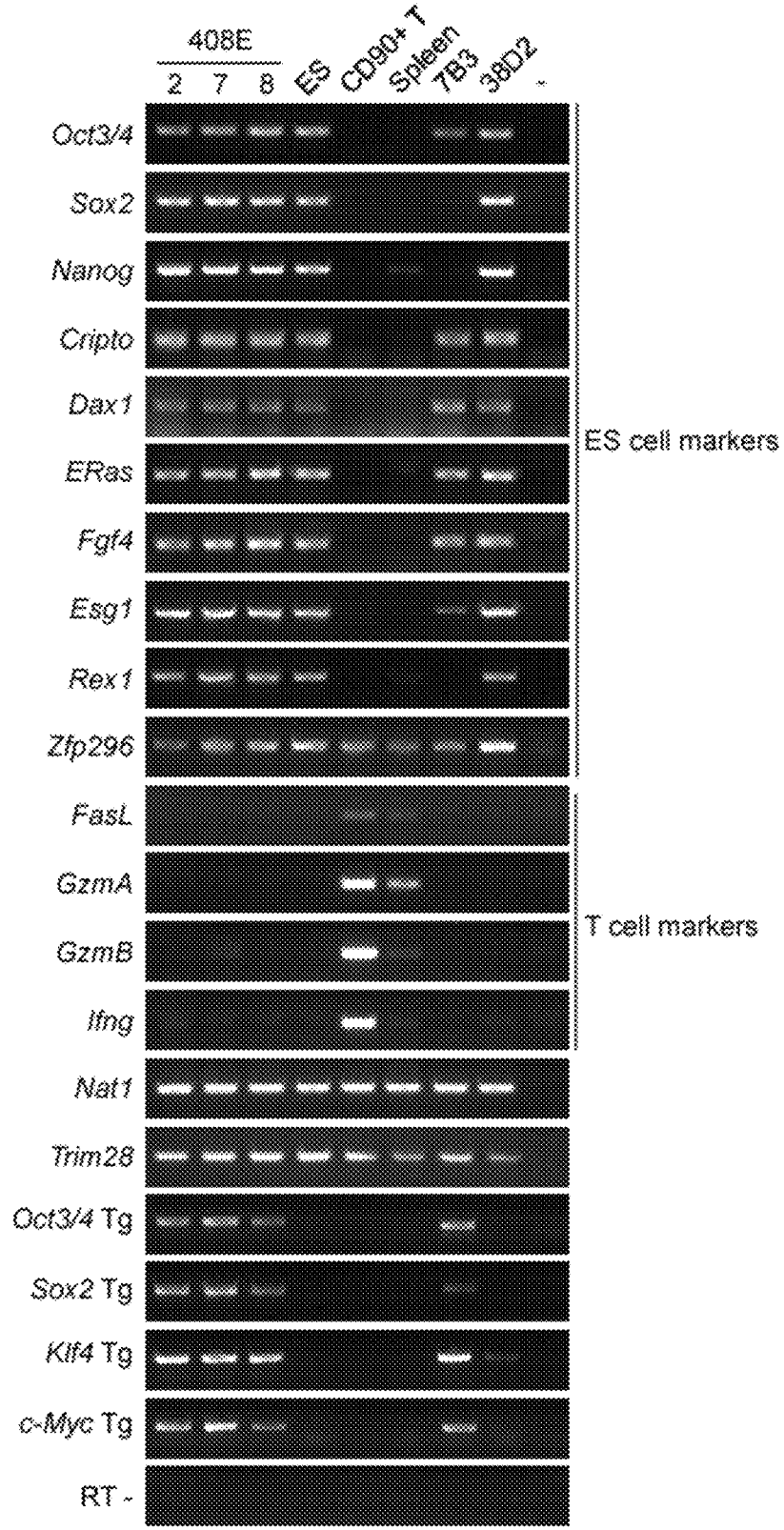
FIG. 6 is a photographic representation of RT-PCR showing that ES-like cells resulting from T cells derived from a Nanog-GFP/Trp53$^{-/-}$ mouse infected with 4 factors (Oct3/4, Sox2, Klf4, c-Myc) express ES-cell-specific genes. In the figure, Oct3/4 to Zfp296 are ES cell markers, and FasL to Ifng are T cell markers. Nat1 and Trim28 are positive controls, and Oct3/4 Tg to c-Myc Tg confirm the expression of the 4 factors introduced. In the figure, "CD90+T" and "Spleen" indicate the T cells and spleen that served as cell sources for iPS cell induction, respectively; 7B3 and 38D2 indicate Fbx15 iPS cells (*Nature* 448, 313-317(2007)) and Nanog iPS cells (*Nature* 448, 313-317(2007)), respectively.
Figure 7:
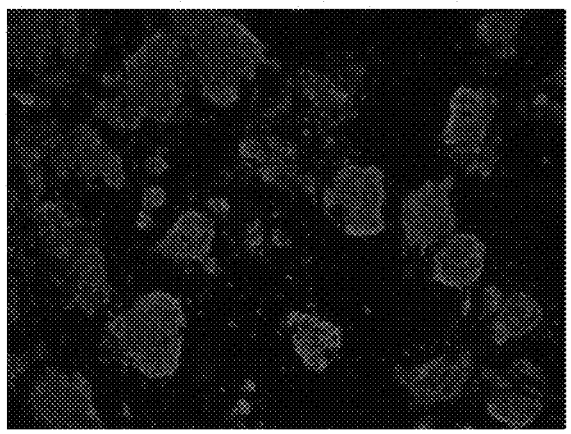
FIG. 7 is a photographic representation showing that ES-like cells resulting from T cells derived from a Nanog- GFP/Trp53$^{-/-}$ mouse infected with 4 factors (Oct3/4, Sox2, Klf4, c-Myc) are positive for ES cell markers SSEA1 and alkaline phosphatase.
Figure 7:
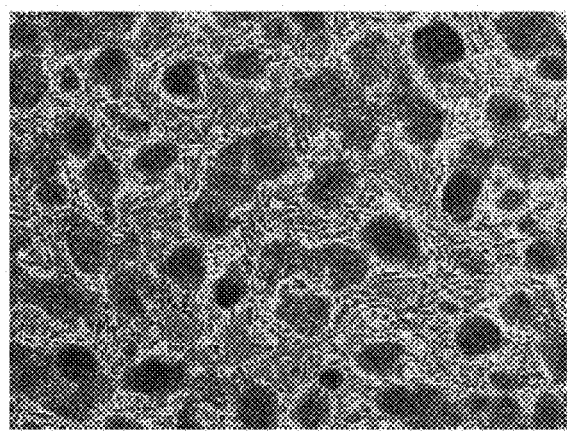
Figure 8:
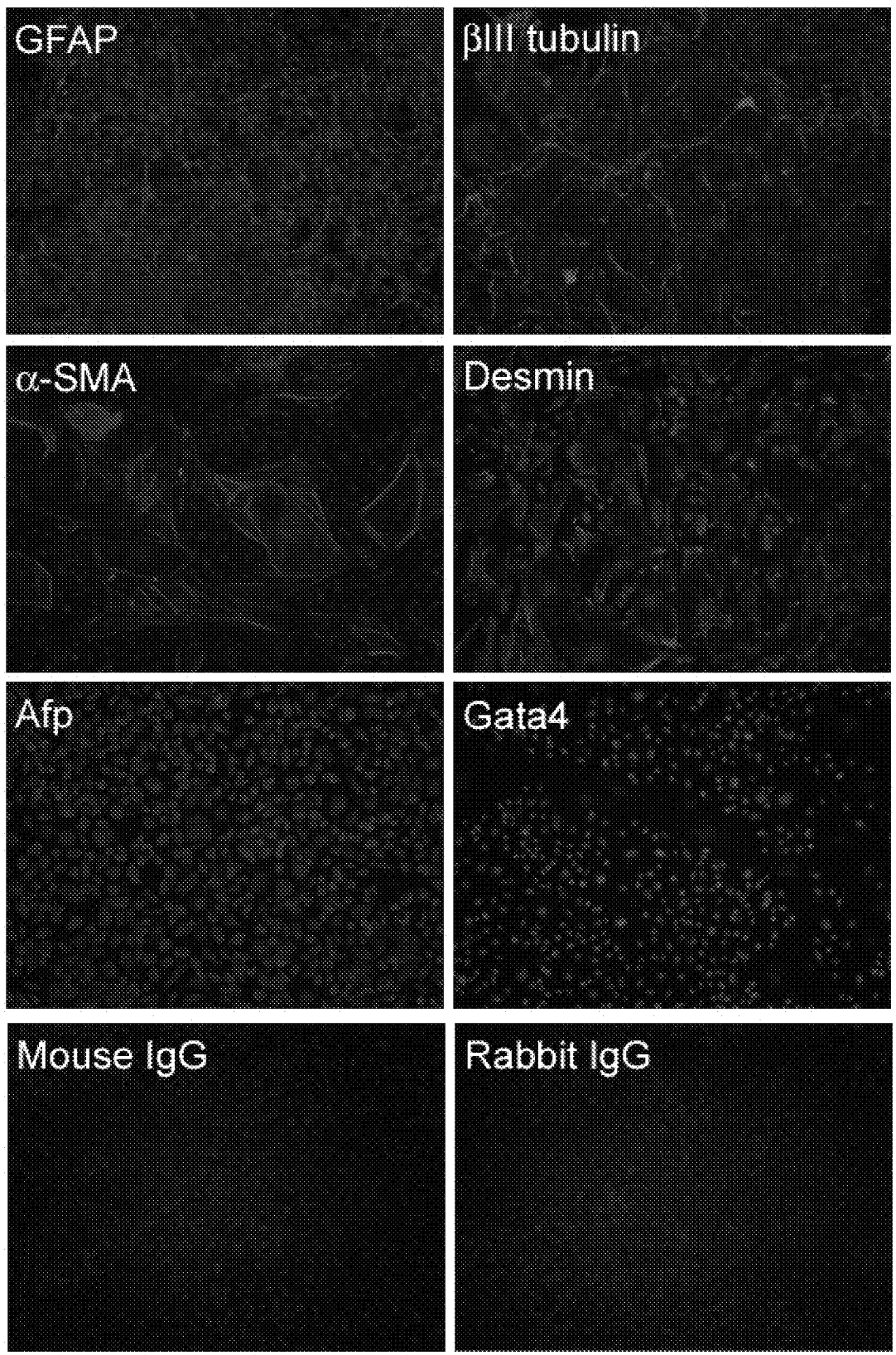
FIG. 8 is a photographic representation showing results confirming that ES-like cells resulting from T cells derived from a Nanog-GFP/Trp53$^{-/-}$ mouse infected with 4 factors (Oct3/4, Sox2, Klf4, c-Myc) possess a potential for differentiating into three germ layers, by staining using AFP, GATA4, α-SMA, Desmin, 13III-tubulin and GFAP antibodies.

On day 17 after the establishment of T cells, 11 GFP-positive colonies were observed, which were picked up and sown to a 24-well SNL-PH plate. As a result, 3 clones of ES-like cells were obtained (408E2, E7, E8). These clones exhibited a mouse ES cell-like morphology and were positive for Nanog-GFP (FIG. 5). The expression of ES cell-specific genes (Oct3/4, Sox2, Nanog, Cripto, Dax1, ERas, Fgf4, Esg1, Rex1) was confirmed by RT-PCR (FIG. 6). The silencing of the exogenous genes incorporated was incomplete (FIG. 6). None of these clones expressed a T cell marker (FasL, GzmA, GzmB, Ifng) (Rever Tra Ace kit, Takara, was used). Staining with anti-SSEA1 antibody (Santacruz) confirmed the expression thereof, and the clones were also positive for alkaline phosphatase activity (FIG. 7). Furthermore, as a result of in vitro differentiation induction by embryoid formation, staining using AFP (R&D systems), GATA4 (Santacruz), a-SMA (DAKO), Desmin (Neomarker), bIII-tubulin (Chemicon), and GFAP (DAKO) antibodies confirmed the expression thereof, it was found that the clones possessed the potential for differentiating into three germ layers (FIG. 8). It was also confirmed that the clones also contributed to the genesis of chimeric mice (data not shown). Thus, the resulting GFP-positive colonies were identified as iPS cells.

When the same experiment was performed, but using Nanog-GFP Tg mouse-derived T cells, absolutely no GFP-positive colony was produced. From the experimental results above, it was demonstrated that by deleting (inactivating) p53, the establishment of iPS cells was promoted, and that by inactivating p53, iPS cells could be established from finally differentiated T cells.

Figure 10:
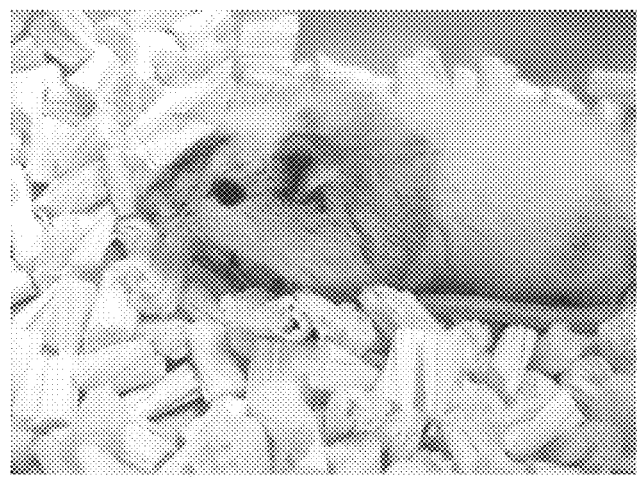
FIG. 10 shows an adult chimeric mouse resulting from an ES-like cell derived from a T cell of a Nanog-GFP/Trp53$^{-/-}$ mouse infected with 4 factors (Oct3/4, Sox2, Klf4, c-Myc).

By microinjecting iPS cells established from T cells as described above into ICR-mouse-derived blastocysts, adult chimeric mice created (FIG. 10). However, all chimeric mice experienced tumorigenesis within 7 weeks.

Figure 11:
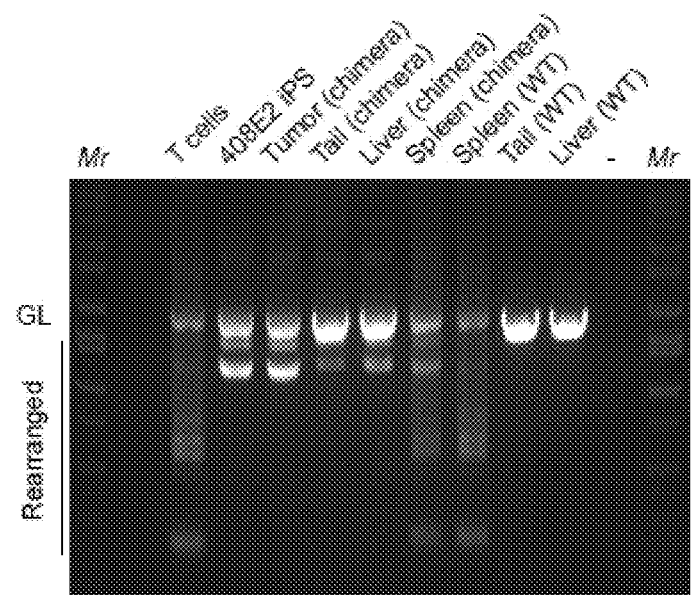
FIG. 11 is a photographic representation showing results confirming the rearrangement of the V-(D)-J DNA of the Tcrpβ gene by genomic PCR. In the figure, "GL" indicates a germline band.

Next, these established iPS cells, various tissues of the chimera, and tumors of the chimera were examined by PCR for rearrangement of the T cell receptor gene (V-(D)-J DNA of Tcrβ gene). Specifically, this examination was performed in accordance with the method described in Curr Biol 11(19), 1553 (2001). Briefly, an attempt was made to detect Dβ2-Jβ2 rearrangement of the Tcrβ gene by conducting PCR amplification on genomic DNA using primer sets Dβ2 (GTAGGCACCTGTGGGGAAGAAACT; SEQ ID NO:29) and Jβ2 (TGAGAGCTGTCTCCTACTATCGATT; SEQ ID NO:30), and electrophoresing the resulting PCR product on 1.2% agarose gel. As a result, a band of the rearranged T cell receptor was detected; the iPS cells were identified as being derived from T cells. The rearranged band in chimera tumor was as dense as that of the iPS cells, it was suggested that the tumor might be derived from the iPS cells (FIG. 11).

Example 5: Microarray Analysis

Figures 9A, 9B, 9C:
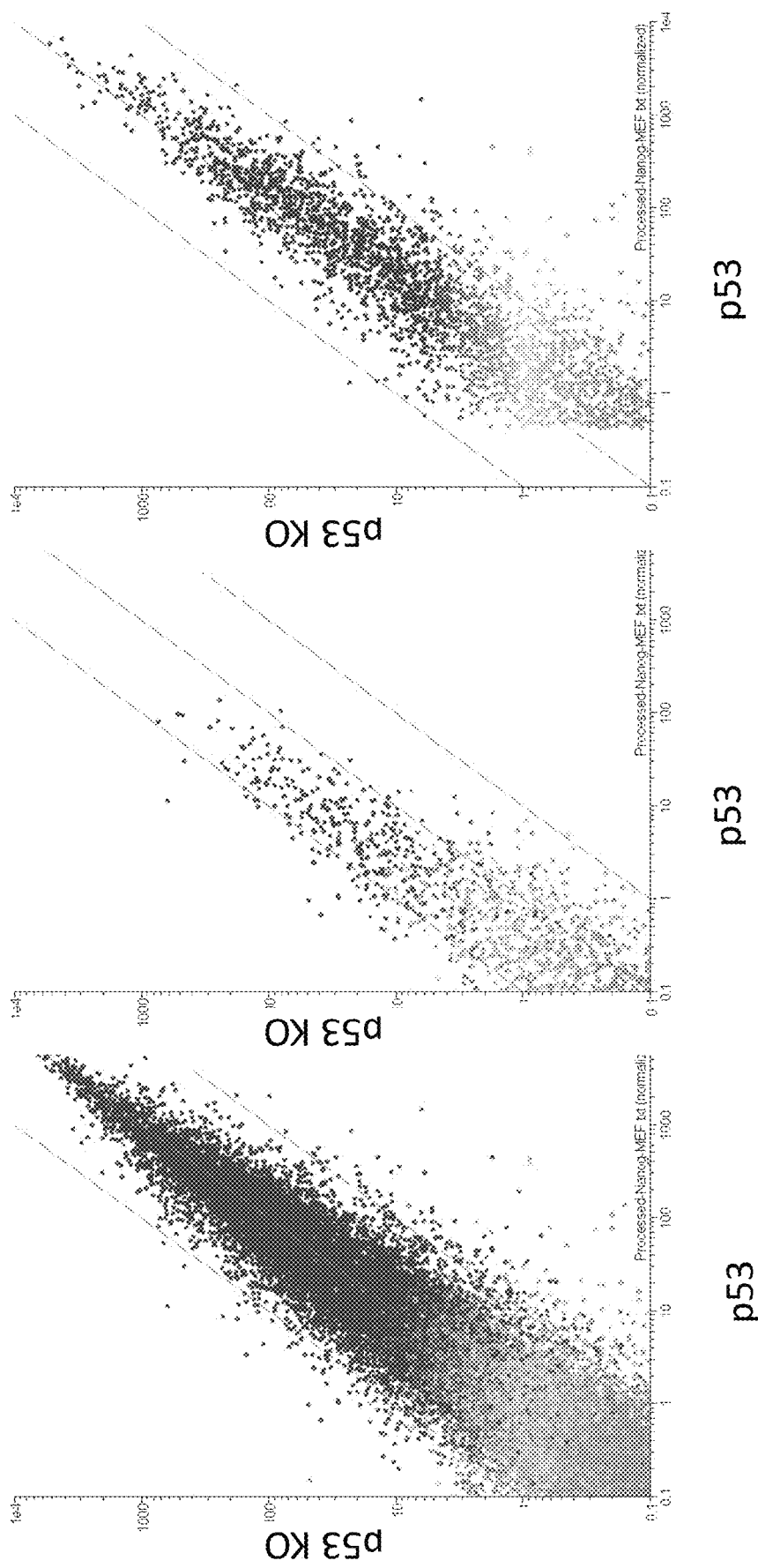
FIGS. 9A-9C are a graphic representation of results of a DNA microarray analysis performed to determine whether there is a difference in expression pattern between MEF isolated from a p53-homo-deficient mouse and MEF isolated from an ordinary, non-p53-deficient mouse. For FIG. 9A, all genes were detected. For FIG. 9B, genes expressed specifically in ES cells only were detected. For FIG. 9C, genes expressed specifically in fibroblasts (MEF) only were detected.

To determine whether there was a difference in expression pattern between MEFs isolated from a p53 homo-deficient mouse and MEFs isolated from an ordinary, non-p53-deficient mouse, DNA microarray analysis was performed. The analysis was performed using total RNA derived from MEFs isolated from each mouse, by the technique described in Cell, 131, 861-872(2007). The results are shown in FIGS. 9A-9C. An attempt was made to detect genes expressed specifically in ES cells (genes expressed at levels 10 times or more higher in the ES cells than in the fibroblasts); in the MEFs derived from the p53-deficient mouse, compared with the wild-type MEFs, these genes expressed specifically in the ES cells were expressed much more (FIG. 9B). Conversely, an attempt was made to detect genes expressed specifically in fibroblasts (a group of genes expressed at levels 10 times or more higher in the fibroblasts than in the ES cells); in the MEFs derived from the p53-deficient mouse, compared with the wild-type MEFs, the expression of these genes expressed specifically in the fibroblasts was extremely lower (FIG. 9C). From the results above, it was shown that by deleting p53, a state close to ES cells was generated.

Figure 12C:
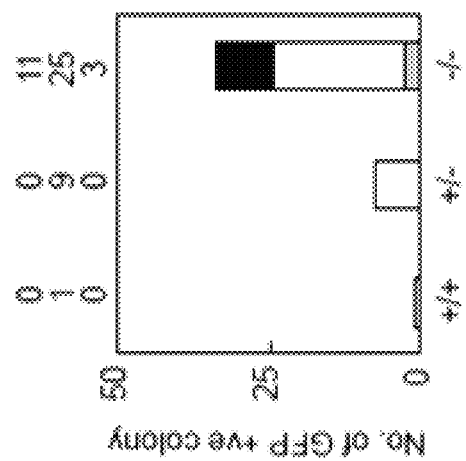
FIGS. 12A-12C show iPS generation from p53-null MEF by the four or three factors.
Figure 12B:
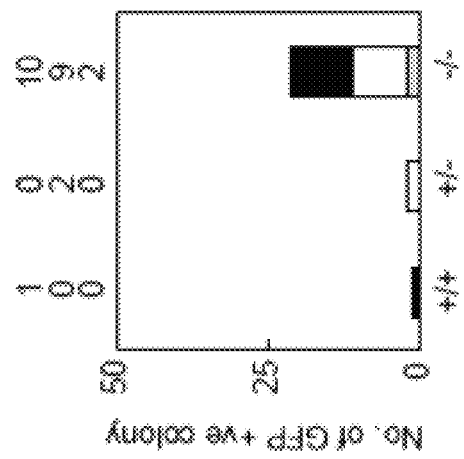

Example 6: Effects of p53 Deficiency and Introduction of a Dominant Negative Mutant We used either the Nanog-GFP or Oct3/4-GFP reporter system for sensitive and specific identification of iPS cells (Okita K. et al. *Nature* 448, 313 (2007)). Wild type, p53$^{+/-}$, or p53$^{-/-}$ MEFs, which also contain the Nanog-GFP reporter, were seeded at $1\times10^5$ cells per well of 6 well plates. The cells were infected next day (day 0) with retrovirus made from Plat-E. On day 5, cells were reseeded either at one cell per well of 96-plates by a cell sorter (FACS Aria, Beckton Dekinson) or 5000 cells per 100 mm-dish. Puromycin selection (1.5 g/ml) was initiated on day 13 in the four-factor protocol and on day 19 in the three factor protocol. Numbers of GFP positive colonies were determined on day 21 for the four-factor protocol and on day 28 in the three factor protocol. The results are shown in FIGS. 12A-12C.

Figure 12A:
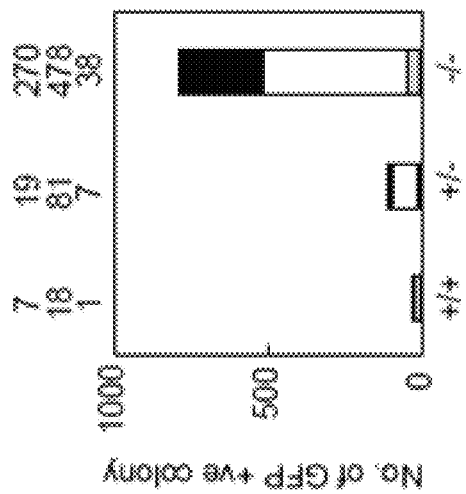

When the three factors devoid of Myc were introduced into Nanog-GFP, p53-wild type MEF, we obtained 1~18 GFP-positive colonies from 5000 transduced fibroblasts (FIG. 12A). From Nanog-GFP, p53-heterozygous mutant MEFs, we observed 7~81 GFP-positive colonies. In contrast, from Nanog-GFP, p53-null fibroblasts, 38~478 GFP-positive colonies emerged.

We next tried to generate iPS cells from a single fibroblast. By using a flow cytometer, we plated one Nanog-GFP cell (p53 wild-type, heterozygous mutant, or homozygous mutant), which was transduced with the three factors five days before the re-plating, into a well of 96-well plates. Twenty-three days after the re-plating, we observed GFP-positive colonies in zero or one well per a 96-well plate with p53 wild-type fibroblasts (FIG. 12B). By great contrast, we observed GFP-positive colonies in ~2 and ~10 wells per a 96-well plate with p53-heterozyous fibroblasts and p53-null fibroblasts, respectively. These data showed that loss of p53 function markedly increase the efficiency of direct reprogramming and up to 10% of transduced cells can become iPS cells with the three factors devoid of Myc.

We performed the same experiment with the four factors including c-Myc. We observed GFP-positive colonies in zero or one well per a 96-well plate with p53 wild-type fibroblasts (FIG. 12B). By great contrast, we observed GFP-positive colonies in ~9 and ~25 wells per a 96-well plate with p53-heterozyous fibroblasts and p53-null fibroblasts, respectively. These data showed that addition of the Myc retrovirus further increased the efficiency of direct reprogramming up to 20%.

To confirm the suppressive role of p53 in iPS cell generation, we performed two sets of experiments. First, we tested the effect of dominant negative mutants of p53 on the generation of iPS cells. Complimentary DNA of mouse p53 gene was amplified by RT-PCR with p53-1S (CAC CAG GAT GAC TGC CAT GGA GGA GTC; SEQ ID NO:31) and p53-1223AS (gtg tct cag ccc tga agt cat aa; SEQ ID NO:32), and subcloned into pENTER-D-TOPO (Invitrogen). After sequencing verification, cDNA was transferred to pMXs-gw by Gateway cloning technology (Invitrogen). Retroviral vectors for p53 mutants were generated by two step PCR. For the P275S mutant (Annemieke de Vries (2002), supra), the first PCR was performed with two primer sets, p53-P275S-S(tgt ttg tgc ctg ctc tgg gag aga ccg c; SEQ ID NO:33) and p53-1223AS, and p53-P275S-AS (gcg gtc tct ccc aga gca ggc aca aac a; SEQ ID NO:34) and p53-1S. For the D278N mutant (Shinmura K. et al. Oncogene 26(20), 2939 (2007)), the first PCR was performed with two primer sets, p53-D278N-S(tgc cct ggg aga aac cgc cgt aca gaa; SEQ ID NO:35) and p53-1223AS, and p53-D278N-AS (ttc tgt acg gcg gtt tct ccc agg gca; SEQ ID NO:36) and p53-1S. For the S58A mutant (Cecchinelli B. et al. *Cell Death Differ* 13(11), 1994 (2006)), the first PCR was performed with two primer sets, p53-S58A-S(ttt gaa ggc cca GCt gaa gcc ctc cga; SEQ ID NO:37) and p53-1223AS, and p53-S58A-AS (tcg gag ggc ttc aGC tgg gcc ttc aaa; SEQ ID NO:38) and p53-1S. The two PCR products of each first PCR were mixed and used as a template for the secondary PCR with the primer set, p53-1S and p53-1223AS. These mutants were cloned into pENTR-D-TOPO, and then transferred to pMXs-gw by Gateway cloning technology. The retroviruses expressing p53 mutants obtained were co-transduced with the three factors into Oct4-GFP, p53$^{+/-}$ or p53$^{-/-}$ MEFs. The results are shown in FIGS. 13A-13B.

When the dominant negative mutant P275S was introduced into Oct4-GFP, p53-heterozygous MEF, we observed substantial increase in the number of GFP-positive colonies (FIG. 13A). By contrast, the wild-type p53 decreased the efficiency of iPS cell generation.

Second, we placed cDNA encoding the wild-type p53 or transactivation-negative mutant (D278N or S58A) into the pMXs retroviral vector (Morita S. et al. *Gene Ther* 7(12), 1063 (2000)) and introduced it together with the retroviruses for the three reprogramming factors into Nanog-GFP, p53-null MEFs. We found that the wild-type p53 markedly decreased the number of GFP-positive colonies (FIG. 13B). The transactivation-negative p53 mutants, in contrast, showed weaker effects than did the wild-type protein. These data confirmed that loss of p53 is responsible to the observed increase in the efficiency of direct reprogramming.

Figure 14:
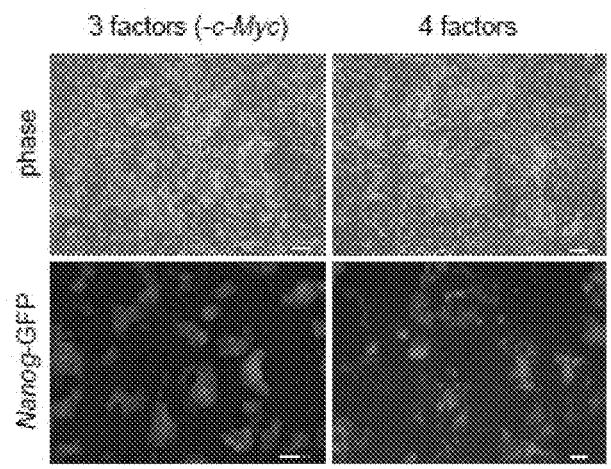
Figure 15:
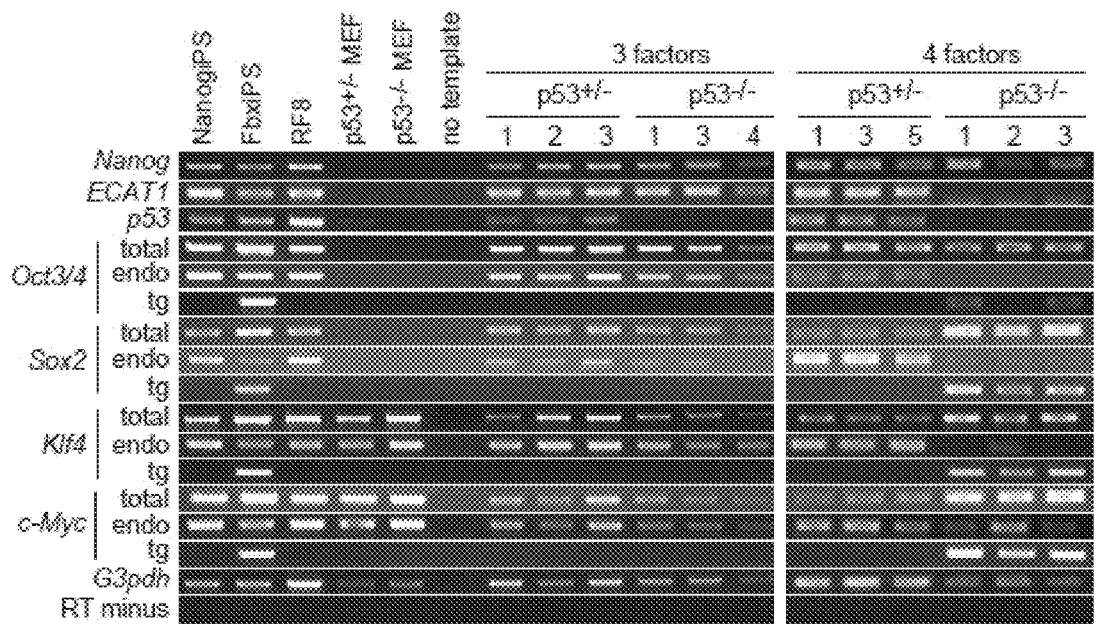
Figure 16A:
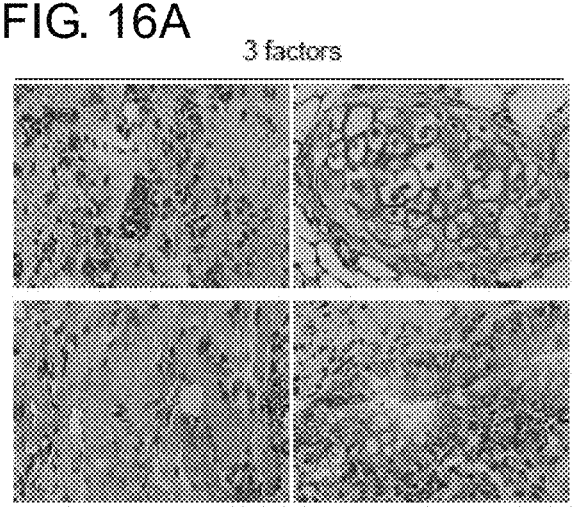

Next, we randomly expanded ten clones of GFP-positive, p53-null cells, generated by the three factors. All the clones showed morphology similar to that of mouse ES cells (FIG. 14, left). The iPS cells generated by the three factors expressed ES cell marker genes at comparable levels to those in ES cells (FIG. 15, left). The expression of the three transgenes was effectively silenced. When transplanted into nude mice, they gave rise to teratomas containing various tissues (FIG. 16A). These data confirmed pluripotency of iPS cells generated by the three factors from p53-null MEFs.

Figure 16B:
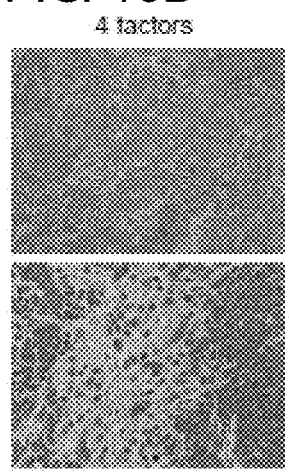

We found that iPS cells generated by the four factors including c-Myc also showed a morphology indistinguishable from that of ES cells (FIG. 14, right). However, the expressions of ES-cell markers were lower in these cells than in ES cells (FIG. 15, right). In addition, transgene expression of the four factors remained active in these cells. Consistent with this observation, tumors derived from these cells in nude mice largely consist of undifferentiated cells, with only small areas of differentiated tissues (FIG. 16B). Thus c-Myc, in the p53-null background, suppresses retroviral silencing and inhibits differentiation.

Example 7: Effects of p53 Suppression on Establishment of Human iPS Cells (A) We then examined whether p53 deletion increased efficiency of human iPS cell generation. To this end, we introduced the dominant negative mutatants of p53 (p275S or DD (Bowman T. et al. *Genes Dev* 10(7), 826 (1996))) into adult human dermal fibroblasts (HDFs) together with the three or four reprogramming factors. Retroviral vector for the P275S mutant was generated as described in Example 6. Retroviral vector for the DD mutant was generated by two step PCR. The first PCR was performed with two primer sets, p53-DD-S(cgg ata tca gcc tca aga gag cgc tgc c; SEQ ID NO:39) and p53-1223AS, and p53-DD-AS (ggc agc gct ctc ttg agg ctg ata tcc g; SEQ ID NO:40) and p53-1S. Retroviruses for dominant negative mutants, and the four or three reprogramming factors were produced in PLAT-E cells. For iPS cell generation, equal amounts of PLAT-E supernatants containing each retrovirus were mixed and transduced to HDF.

Figure 17A:
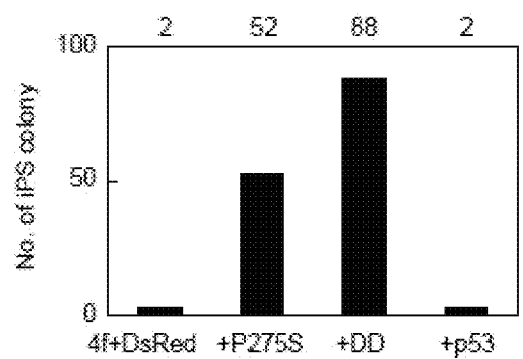
Figure 17B:
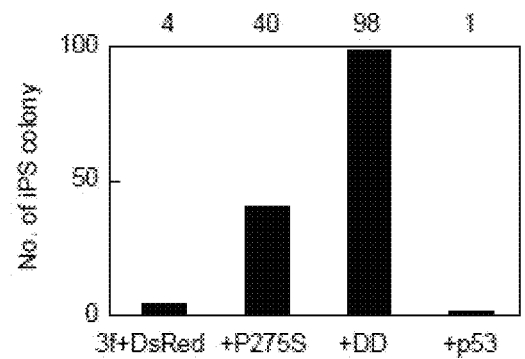
Figure 17C:
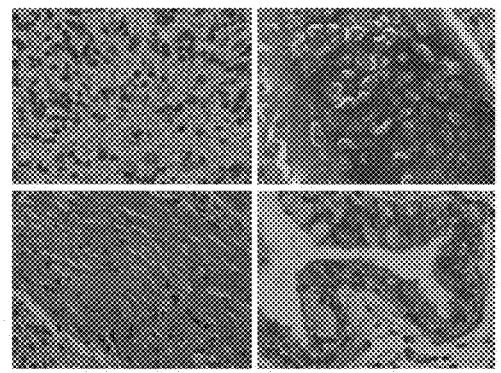

We found that the numbers of iPS cell colonies markedly increaed with the two independent p53 dominant negative mutants (FIGS. 17A-17B). When transplanted into testes of SCID mice, the human iPS cells generated by the three factors and the p53DD mutant developed teratomas containing various tissues of three germ layers (FIG. 17C).

(B) In another experiment, we examined effects of shRNA against human p53 (shRNA2; Stewart S. A. et al. RNA 9(4), 493 (2003)). Retroviral vectors for shRNA expression, pMKO.1-puro (Addgene #8452), pMKO.1-puro p53 shRNA1 (Addgene #10671) and pMKO.1-puro p53 shRNA2 (Addgene #10672; shRNA sequence is shown in SEQ ID NO:28), were obtained from Addgene. Retroviruses for shRNAs, and the four or three reprogramming factors were produced in PLAT-E cells. For iPS cell generation, equal amounts of PLAT-E supematants containing each retrovirus were mixed and transduced to HDF.

Figure 18:
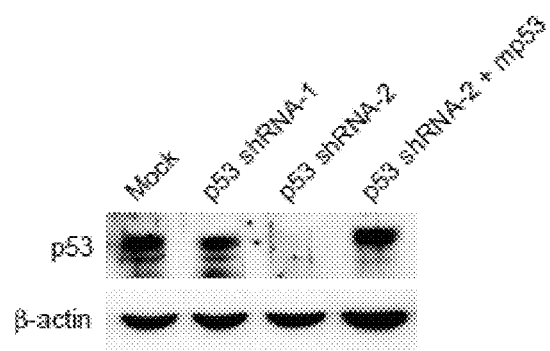
Figure 19:
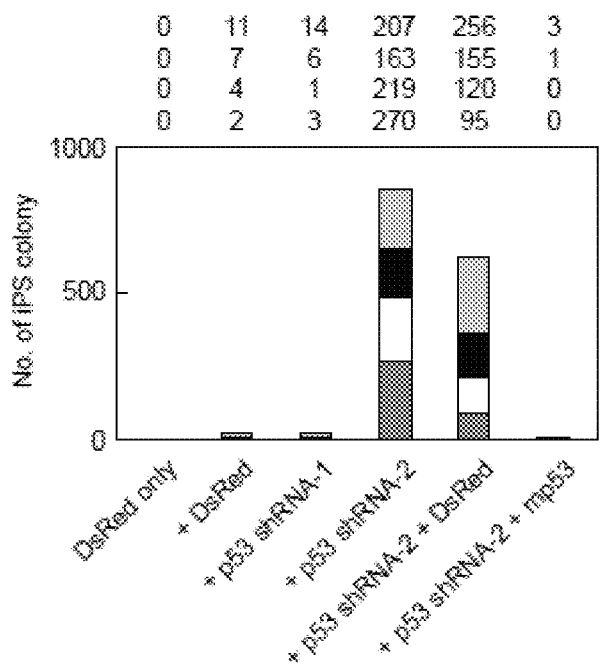
Figure 20A:
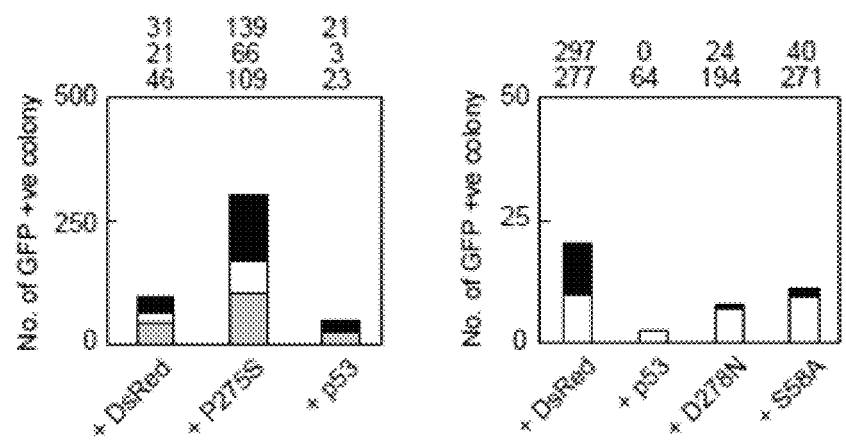
Figure 20B:
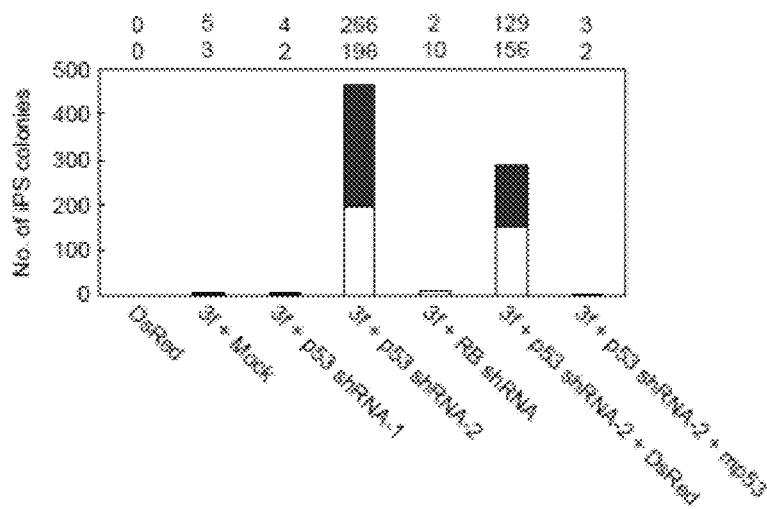

We confirmed that p53 shRNA2 effectively suppressed the p53 protein level (FIG. 18) in HDFs. When co-introduced with the four reprogramming factors, the p53 shRNA markedly increased numbers of human iPS cell coloneis (FIG. 19). A control shRNA containing one nucleotide deletion in the antisense sequece (shRNA1) did not show such effects (FIG. 18 and FIG. 19). Co-introduction of the mouse p53 suppressed the effect of shRNA2. Similar results were obtained when co-introduced with the three reprogramming factors (FIGS. 20A-20B). These data demonstrated that p53 suppresses direct reprogramming not only in mice, but also in human.

Example 8: Functional Inhibition of p53 by MDM2

The effects of MDM2 that binds with and inhibits p53 were examined. Specifically, human MDM2 gene (SEQ ID NO:41) was co-introduced with the four or three reprogramming factors into HDFs using retroviral vectors, and iPS colonies were formed in the same manner as in Example 7 (n=4).

Figure 21A:
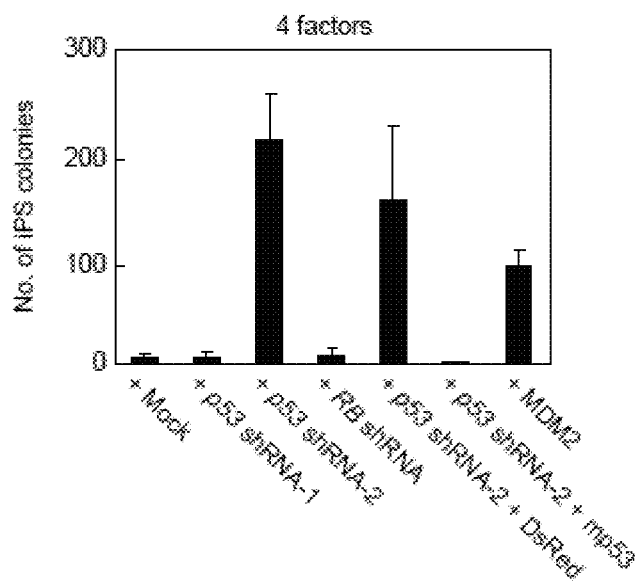
FIGS. 21A and 21B show effects of MDM2 co-transduction on iPS generation from HDFs by the four or three reprogramming factors. The retroviral vector expressing MDM2, p53 shRNA or RB shRNA, or control vector was transduced into HDFs together with the four factors (FIG. 21A) or three factors (FIG. 21B). Shown are the numbers of iPS colonies from 5×10$^4$ cells of HDF.
Figure 21B:
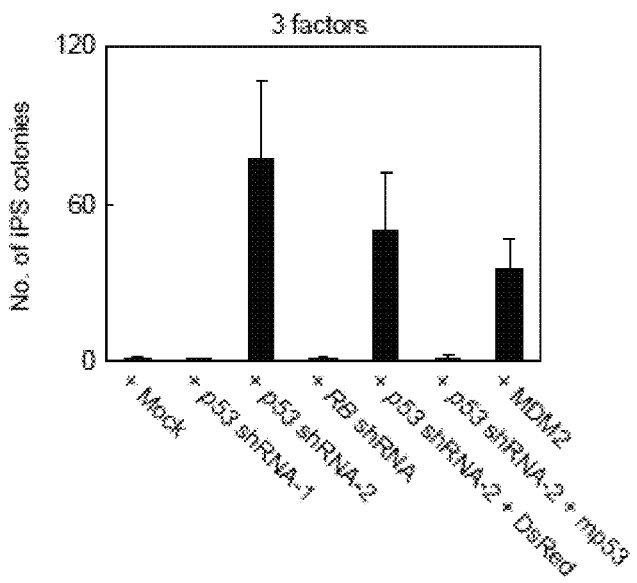

As a result, the co-introduction of MDM2 gene improved the establishment efficiency of iPS cells (FIGS. 21A-21B). While MDM2 also interacts with and inhibits another tumor suppressor, Retinoblastoma (Rb), suppression of Rb by shRNA did not increase the efficiency of iPS cell generation. These data suggest that the effects of MDM2 are caused by suppression of the p53 function.

Example 9: In Vitro Differentiation Induction and Immunostaining

Figure 22:
FIG. 22 shows photographs demonstrating the expression of endoderm-(AFP), mesoderm-(α-SMA) and ectoderm-(βIII-tublin) differentiation markers in the cells that differentiated from the iPS clones.

Next, the present inventors confirmed whether the cells generated with the three reprogramming factors and the p53 shRNA in Example 7(B) were pluripotent by in vitro differentiation. To form embryoid bodies, the cells were harvested and transferred to poly-hydroxyethyl methacrylate (HEMA)-coated dishes and incubated for 8 days. After floating culture, the embryoid bodies formed were plated onto gelatin-coated plates and incubated for another 6 days. After incubation, the cells were fixed with 4% paraformaldehyde and permeabilized and blocked with PBS containing 5% normal goat serum, 1% BSA and 0.2% TritonX-100. The expression of differentiation markers (AFP, α-SMA, βIII-tublin) was examined by immunocytochemistry. As primary antibodies, anti-α-fetoprotein (AFP) (1:100, R&D systems), anti-α-smooth muscle actin (α-SMA) (1:500, DAKO) and anti-P3III-tublin (1:100, Chemicon) were used. Cy3-labeled anti-mouse IgG (1:500, Chemicon) was used as secondary antibody. Nuclei were stained with Hoechst 33342 (Invitrogen). The results are shown in FIG. 22. The iPS cells differentiated into three germ layers such as endoderm (AFP), mesoderm (α-SMA) and ectoderm (P3III-tublin). No significant difference in differentiation potentials was found between the iPS clones.

Example 10: RT-PCR Analysis of Undifferentiated Markers and Differentiated Markers The expression of stem cell markers (Oct3/4, Sox2, Nanog) and differentiation markers (FoxA2 and Sox17 (endoderm), Msx1 (mesoderm), Map2 and Pax6 (ectoderm)) in the human iPS cells obtained in Example 7(B) and the differentiated cells obtained in Example 9 were analyzed by RT-PCR using Rever Tra Ace Kit (Takara). The primer pairs used for amplifying the markers are shown in Table 1.

TABLE 1

| Gene | Sequence (5'-3') | NO: |
|---|---|---|
| Stem cell markers | | |
| Oct3/4 | GAC AGG GGG AGG GGA GGA GCT AGG | 43 |
|  | CTT CCC TCC AAC CAG TTG CCC CAA AC | 44 |
| Sox2 | GGG AAA TGG GAG GGG TGC AAA AGA GG | 45 |
|  | TTG CGT GAG TGT GGA TGG GAT TGG TG | 46 |
| Nanog | CAG CCC CGA TTC TTC CAC CAG TCC C | 47 |
|  | CGG AAG ATT CCC AGT CGG GTT CAC C | 48 |
| Differentiation markers | | |
| FoxA2 | TGG GAG CGG TGA AGA TGG AAG GGC AC | 49 |
|  | TCA TGC CAG CGC CCA CGT ACG ACG AC | 50 |
| Sox17 | CGC TTT CAT GGT GTG GGC TAA GGA CG | 51 |
|  | TAG TTG GGG TGG TCC TGC ATG TGC TG | 52 |
| Msx1 | CGA GAG GAC CCC GTG GAT GCA GAG | 53 |
|  | GGC GGC CAT CTT CAG CTT CTC CAG | 54 |
| Pax6 | ACC CAT TAT CCA GAT GTG TTT GCC CGA G | 55 |
|  | ATG GTG AAG CTG GGC ATA GGC GGC AG | 56 |
| Map2 | CAG GTG GCG GAC GTG TGA AAA TTG AGA GTG | 57 |
|  | CAC GCT GGA TCT GCC TGG GGA CTG TG | 58 |
| Internal standard | | |
| Nat1 | ATT CTT CGT TGT CAA GCC GCC AAA GTG GAG | 59 |
|  | AGT TGT TTG CTG CGG AGT TGT CAT CTC GTC | 60 |

Figure 23:
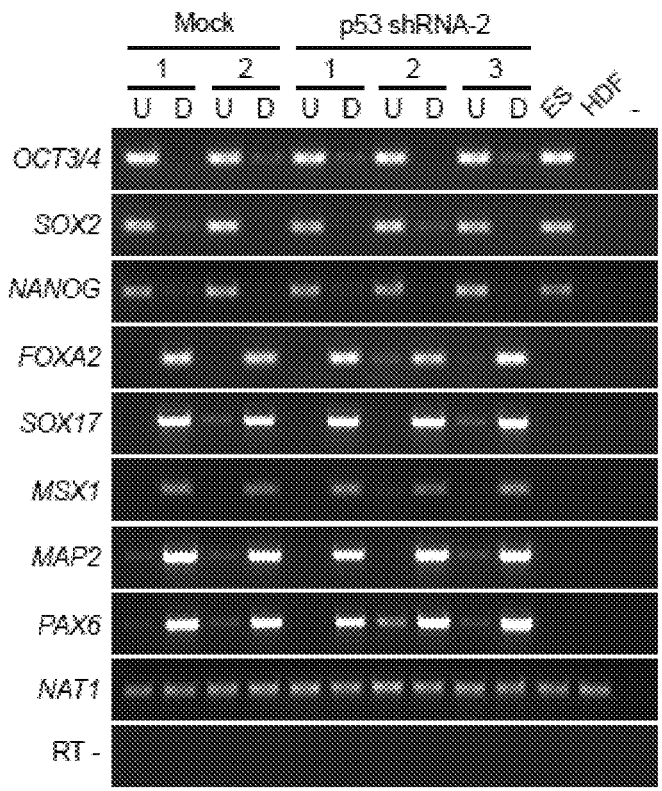
FIG. 23 shows marker gene expressions in undifferentiated cells (U) and in differentiated cells after embryoid body formation (D). "Mock" shows co-transduction of empty vector (pMKO.1-puro) with the three reprogramming factors. "p53 shRNA-2" shows co-transduction of p53 shRNA-2 with the three reprogramming factors.

As a result, the cells generated with the three reprogramming factors and the p53 shRNA expressed Nanog, endogenous Oct3/4, and endogenous Sox2 at comparable levels to those in ES cells (FIG. 23, lanes U). After embryoid body-mediated differentiation, these cells expressed marker genes of the three germ layers (FIG. 23, lanes D). These data demonstrated that p53 suppresses direct reprogramming not only in mice, but also in human.

Example 11: Role of p21 in Improving the Efficiency of Establishment of iPS Cells by p53 Suppression To elucidate p53 target genes that are responsible for the observed enhancement of iPS cell generation, we compared gene expression between p53 wild-type MEF and p53-null MEF by DNA microarrays, and between control HDF and p53 knockdown HDF. In MEF, 1590 genes increased and 1485 genes decreased >5 fold in p53-null MEF. In HDF, 290 genes increased and 430 genes decreased >5 fold by p53 shRNA. Between mouse and human, eight increased genes are common, including v-myb myeloblastosis viral oncogene homolog (MYB) and a RAS oncogenes family, RAB39B (Table 2). Twenty-seven decreased genes were common between the two species, including p53, cyclin-dependent kinase inhibitor 1A (p21, Cip1), BTG family, member 2 (BTG2), zinc finger, matrin type 3 (ZMAT3), and MDM2.

TABLE 2

| Accession No. | Gene Name |
| --- | --- |
| Increased genes | |
| NM_000809 | *Homo sapiens* gamma-aminobutyric acid (GABA) A receptor, alpha 4 (GABRA4) |
| NM_182767 | *Homo sapiens* solute carrier family 6 (neutral amino acid transporter), member 15 (SLC6A15), transcript variant 1 |
| NM_014264 | *Homo sapiens* polo-like kinase 4 (*Drosophila*) (PLK4) |
| NM_198391 | *Homo sapiens* fibronectin leucine rich transmembrane protein 3 (FLRT3), transcript variant 2 |
| NM_171998 | *Homo sapiens* RAB39B, member RAS oncogene family (RAB39B) |
| NM_001482 | *Homo sapiens* glycine amidinotransferase (L-arginine:glycine amidinotransferase) (GATM), nuclear gene encoding |
| NM_001130173 | *Homo sapiens* v-myb myeloblastosis viral oncogene homolog (avian) (MYB), transcript variant 1 |
| NM_004004 | *Homo sapiens* gap junction protein, beta 2, 26 kDa (GJB2) |
| Decreased genes | |
| NM_000546 | *Homo sapiens* tumor protein p53 (TP53), transcript variant 1 |
| NM_000389 | *Homo sapiens* cyclin-dependent kinase inhibitor 1A (p21, Cip1) (CDKN1A) |
| NM_001461 | *Homo sapiens* flavin containing monooxygenase 5 (FMO5) |
| NM_002474 | *Homo sapiens* myosin, heavy chain 11, smooth muscle (MYH11), transcript variant SM1A |
| NM_006763 | *Homo sapiens* BTG family, member 2 (BTG2) |
| NM_004455 | *Homo sapiens* exostoses (multiple)-like 1 (EXTL1) |
| NM_022470 | *Homo sapiens* zinc finger, matrin type 3 (ZMAT3), transcript variant 1 |
| NM_006536 | *Homo sapiens* CLCA family member 2, chloride channel regulator (CLCA2) |
| NM_001017915 | *Homo sapiens* inositol polyphosphate-5-phosphatase, 145 kDa (INPP5D), transcript variant 1 |
| NM_006879 | *Homo sapiens* Mdm2, transformed 3T3 cell double minute 2, p53 binding protein (mouse) (MDM2), transcript variant |
| NM_004469 | *Homo sapiens* c-fos induced growth factor (vascular endothelial growth factor D) (FIGF) |
| NM_016352 | *Homo sapiens* carboxypeptidase A4 (CPA4) |
| NM_024817 | *Homo sapiens* thrombospondin, type I, domain containing 4 (THSD4) |
| NM_000526 | *Homo sapiens* keratin 14 (KRT14) |
| NM_000846 | *Homo sapiens* glutathione S-transferase A2 (GSTA2) |
| NM_000198 | *Homo sapiens* hydroxy-delta-5-steroid dehydrogenase, 3 beta- and steroid delta-isomerase, 2 (HSD3B2) |
| NM_032866 | *Homo sapiens* cingulin-like 1 (CGNL1) |
| NM_000230 | *Homo sapiens* leptin (LEP) |
| NM_020405 | *Homo sapiens* plexin domain containing 1 (PLXDC1) |
| NM_004975 | *Homo sapiens* potassium voltage-gated channel, Shab-related subfamily, member 1 (KCNB1) |
| NM_001128310 | *Homo sapiens* SPARC-like 1 (hevin) (SPARCL1), transcript variant 1 |
| NM_032588 | *Homo sapiens* tripartite motif-containing 63 (TRIM63) |
| NM_022047 | *Homo sapiens* differentially expressed in FDCP 6 homolog (mouse) (DEF6) |
| NM_003322 | *Homo sapiens* tubby like protein 1 (TULP1) |
| NM_003012 | *Homo sapiens* secreted frizzled-related protein 1 (SFRP1) |
| NM_002164 | *Homo sapiens* indoleamine-pyrrole 2,3 dioxygenase (INDO) |
| NM_004060 | *Homo sapiens* cyclin G1 (CCNG1), transcript variant 1 |

Figure 24A:
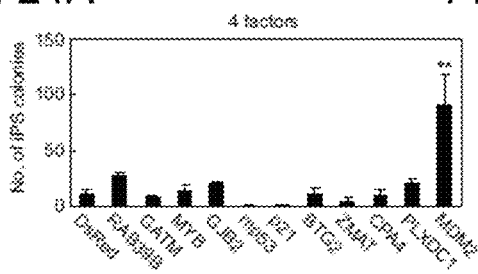
FIGS. 24A-24C show effects of p53 suppression on p21 and Myc. Genes regulated (4 increased and 7 decreased) by p53 suppression were introduced into HDFs together with the four reprogramming factors (FIG. 24A) or the four reprogramming factors and the p53 shRNA (FIG. 24B). On day 24 (FIG. 24A) or day 28 (FIG. 24B) post-transduction, numbers of iPS cell colonies were counted. ; p<0.01 compared to DsRed control (n=3). Luciferase reporters containing responsive elements of p53 or Myc, or that driven by the polymerase II promoter were introduced into HDFs, together with the mock retroviral vector, the p53 shRNA, the four reprogramming factors, or the three factors devoid of Myc. Two days later, luciferase activities were determined (c). ; p<0.01, *; p<0.05 compared to the mock control (n=3).
Figure 24B:
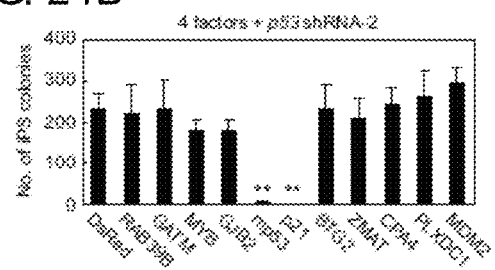

Among these we transduced four increased genes and seven decreased genes by retroviruses into HDF, together with either the four reprogramming factors alone, or with the four factors and the p53 shRNA. We reasoned that if some of these target genes are responsible for the observed enhancement of iPS cell generation, forced expression of increased genes in wild-type fibroblasts would mimic the effect of p53 suppression, whereas co-expression of decreased genes and the p53 shRNA would counteract the effect of p53 suppression. Among the four increased genes, none mimicked the effect of p53 suppression by forced expression of MDM2, which binds to and degrades the p53 proteins (FIG. 24A). Among seven decreased genes, only p53, derived from mouse, and p21 effectively counteracted the effect of the p53 shRNA (FIG. 24B). In addition, the forced expression of p21 markedly decreased iPS cell generation from p53-null MEF. These data highlighted importance of p21 as a p53 target during iPS cell generation in both mouse and human.

Suppression of p53-p21 results in inactivation of Rb. However, suppression of Rb by shRNA did not increase the efficiency of iPS cell generation (FIGS. 21A-21B). These data suggest that the effect of p53-p21 suppression on iPS cell generation is, at least in part, attributable to mechanisms other than regulation of Rb.

Figure 24C:
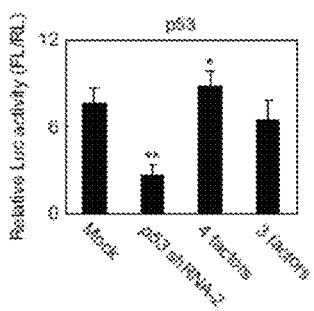
Figure 24C:
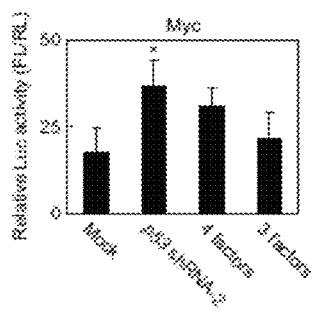
Figure 24C:
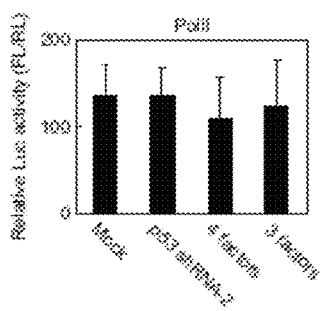

The p21 protein binds to Myc and suppresses its transcriptional activity (Kitaura, H. et al., *J Biol. Chem.*, 275 (14), 10477-10483 (2000)). This might contribute to the increased efficiency of iPS cell generation by p53-p21 suppression. We evaluated the Myc activity in HDF by introducing luciferase reporters driven by either a p53-responsive element or a Myc responsive element (FIG. 24C). We confirmed the p53 activity was reduced by the shRNA. In these knockdown cells, the Myc activity was significantly enhanced. The effect was stronger than that observed with the introduction of the four factors including c-Myc. These data suggest that the activation of Myc contributes to the enhanced iPS cell generation by p53-p21 suppression.

Example 12: Establishment of iPS Cells by Plasmid Introduction

Expression vector pCX-2A-Ms-OKS that expresses mouse Oct3/4, Klf4 and Sox2, and expression vector pCX-Ms-cMyc that expresses mouse c-Myc were both prepared according to Science, 322, pp. 949-953 (2008).

Figure 25A:
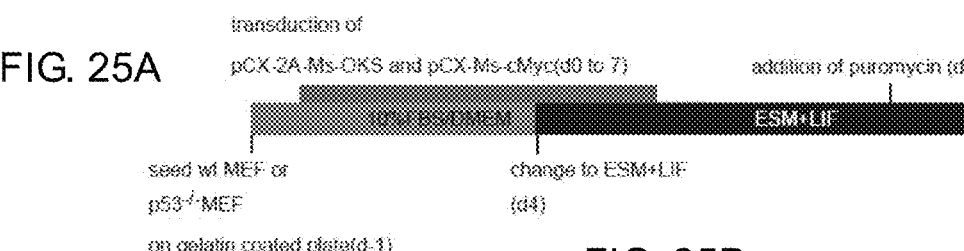
FIG. 25A shows an outline of the experimental procedure.
Figure 25B:
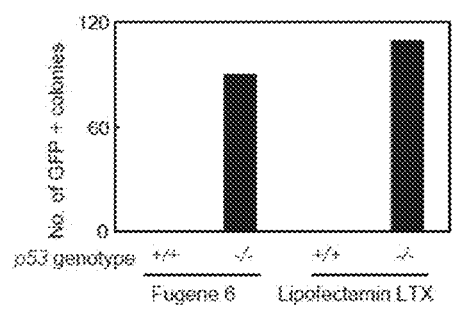
FIG. 25B shows results of introduction of 4 factors (Oct3/4, Sox2, Klf4, c-Myc). In the figures, "+/+" shows results for wild-type cells (control); "−/−" shows results for p53-homo-deficient cells. In the figures, the axis of ordinates indicates the number of GFP-positive colonies.

Fibroblasts (MEFs) were isolated from a fetal p53 homo-deficient mouse having the mouse Nanog reporter (13.5 days after fertilization) and wild-type mouse fetus (13.5 days after fertilization). The MEFs were sown to a 6-well culture plate (Falcon) coated with 0.1% gelatin (Sigma) at $1.3 \times 10^5$ per well. The culture broth used was DMEM/10% FBS (DMEM (Nacalai tesque) supplemented with 10% fetal bovine serum), and the cells were cultured at 37° C. and 5% $CO_2$. The following day, using FuGene6 transfection reagent (Roche) or Lipofectamin LTX (Invitrogen) and following the protocol attached to the reagent, pCX-2A-Ms-OKS and pCX-Ms-cMyc were introduced at once (day 0). Introduction was repeated every day up to day 7 from the introduction. On day 4 from the introduction, the medium was changed to an LIF-supplemented ES cell culture medium (prepared by adding 15% fetal bovine serum, 2 mM L-glutamine (Invitrogen), 100 µM non-essential amino acids (Invitrogen), 100 µM 2-mercaptoethanol (Invitrogen), 50 U/mL penicillin (Invitrogen) and 50 µg/mL streptomycin (Invitrogen) to DMEM (Nacarai Tesque)). Subsequently, the LIF-supplemented ES cell culture medium was exchanged with a fresh supply every two days until a colony was observable. Selection with puromycin (1.5 µg/mL) was performed from day 21 after the introduction and GFP-positive colonies were counted on day 33 after the introduction. Summary of the time schedule is shown in FIG. 25A, and the obtained number of GFP-positive colonies is shown in FIG. 25B. When 4 genes were introduced into wild-type MEF by plasmid (+/+ in FIG. 25B), no GFP-positive colony was formed. When 4 genes were introduced into p53 homo-deficient MEF by plasmid (−/− in FIG. 25B), many GFP-positive colonies were obtained.

To examine integration of plasmid DNAs into the genome, 16 kinds of PCR primers capable of amplifying each part of the plasmid were designed (see Science, 322, pp. 949-953 (2008), FIG. 2A), and 11 kinds of primers therefrom were used for Genomic PCR. The results are shown in FIG. 25C. Amplification of exogenous DNA was not observed in 6 clones out of the obtained 12 GFP-positive clones (FIG. 25C: upper panel). By Southern blot analysis using Oct3/4, Sox2, Klf4 and c-Myc as probes, moreover, integration of exogenous gene was not detected in those clones (FIG. 25C: lower panel). The above results reveal that these iPS cells do not integrate pCX-2A-Ms-OKS and pCX-Ms-cMyc plasmids into the host genome.

Figure 25D:
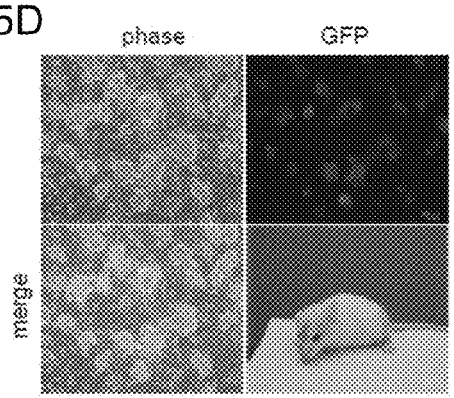
FIG. 25D shows photographs of the obtained cells (upper left: phase-contrast image, upper right: GFP-positive colony image, lower left: merge of phase-contrast image and GFP-positive colony image) and a chimeric mouse resulting from an ES-like cell obtained (lower right panel).
Figure 25C:
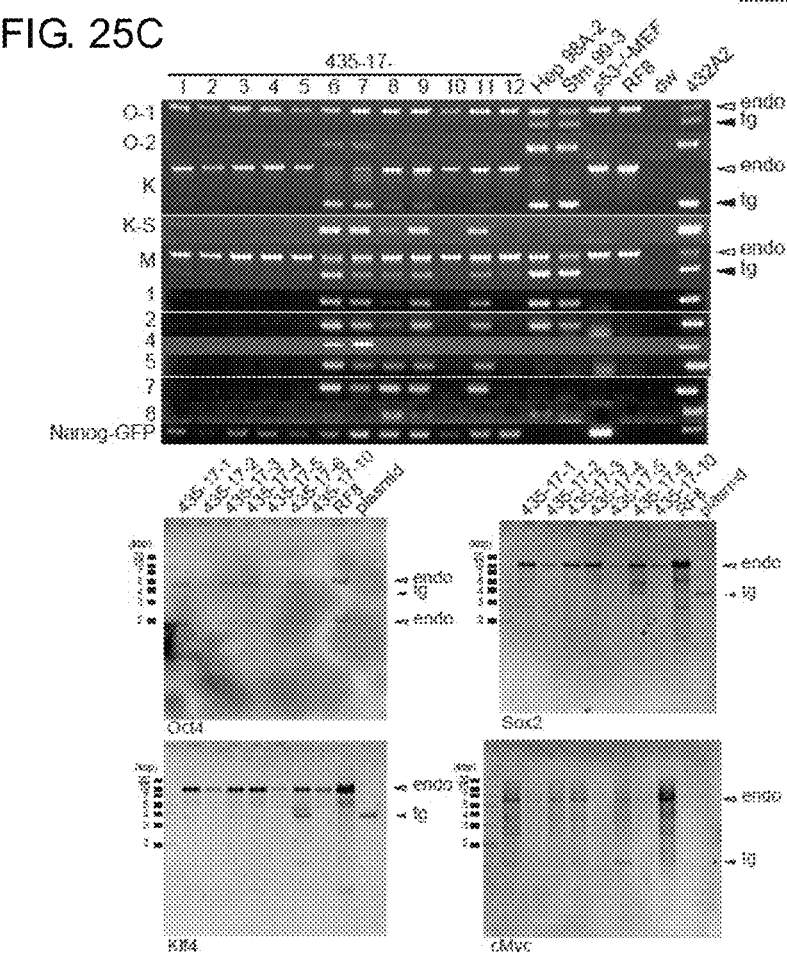
FIG. 25C shows results of examinations of integration of plasmid DNAs into the genome (upper panel: genomic PCR; lower panel: Southern blot analysis).

The photographs of the obtained cells are shown in FIG. 25D (upper left: phase-contrast image, upper right: GFP-positive colony image, lower left: merge of phase-contrast image and GFP-positive colony image). Since the cells had a form morphologically indistinguishable from that of mouse ES cells, and were GFP-positive, establishment of iPS cells was confirmed. Moreover, iPS clones free of plasmid integration were injected to ICR-mouse-derived blastocysts. The results are shown in FIG. 25D, lower right panel. Judging from the hair color, adult chimera could be produced from iPS clone. The results confirm that iPS cells free of plasmid integration have pluripotency.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on U.S. provisional patent application Nos. 61/076,487, 61/095,573, 61/194,700, 61/200,307 and 61/209,686, the contents of which are hereby incorporated by reference.

The invention claimed is:

1. An improved method of producing induced pluripotent stem (iPS) cells, the method comprising contacting isolated mouse somatic cells or adult human dermal fibroblasts with
   (a) nucleic acids encoding reprogramming substances selected from the group consisting of
      (i) Oct3/4, Klf4 and Sox2, and
      (ii) Oct3/4, Klf4, Sox2 and a Myc family member selected from the group consisting of c-Myc, L-Myc, and N-Myc, and
   (b) a p53 inhibitor selected from the group consisting of
      (i) a nucleic acid encoding a dominant negative mutant of p53, and
      (ii) a nucleic acid encoding murine double minute 2 (MDM2),
such that the mouse somatic cells or adult human dermal fibroblasts are reprogrammed into iPS cells, thereby improving the efficiency of establishment of the iPS cells as compared to the same method except that no p53 inhibitor is used.

2. The method of claim 1, wherein the inhibitor of p53 function is a nucleic acid encoding a dominant negative mutant of p53.

3. The method of claim 2, wherein the dominant negative mutant of p53 is p53P275S.

4. The method of claim 2, wherein the dominant negative mutant of p53 is p53DD.

* * * * *

SEQUENCE LISTING

```
<160> NUMBER OF SEQ ID NOS: 60

<210> SEQ ID NO 1
<211> LENGTH: 1782
<212> TYPE: DNA
<213> ORGANISM: Mus musculus
<220> FEATURE:
<221> NAME/KEY: CDS
<222> LOCATION: (129)..(1301)

<400> SEQUENCE: 1
aagttctgta gcttcagttc attgggacca tcctggctgt aggtagcgac tacagttagg      60
gggcacctag cattcaggcc ctcatcctcc tccttcccag cagggtgtca cgcttctccg     120 aagactgg atg act gcc atg gag gag tca cag tcg gat atc agc ctc gag     170
         Met Thr Ala Met Glu Glu Ser Gln Ser Asp Ile Ser Leu Glu
           1               5                  10 ctc cct ctg agc cag gag aca ttt tca ggc tta tgg aaa cta ctt cct     218
Leu Pro Leu Ser Gln Glu Thr Phe Ser Gly Leu Trp Lys Leu Leu Pro
 15                  20                  25                  30 cca gaa gat atc ctg cca tca cct cac tgc atg gac gat ctg ttg ctg     266
Pro Glu Asp Ile Leu Pro Ser Pro His Cys Met Asp Asp Leu Leu Leu
                 35                  40                  45 ccc cag gat gtt gag gag ttt ttt gaa ggc cca agt gaa gcc ctc cga     314
Pro Gln Asp Val Glu Glu Phe Phe Glu Gly Pro Ser Glu Ala Leu Arg
             50                  55                  60 gtg tca gga gct cct gca gca cag gac cct gtc acc gag acc cct ggg     362
Val Ser Gly Ala Pro Ala Ala Gln Asp Pro Val Thr Glu Thr Pro Gly
         65                  70                  75 cca gtg gcc cct gcc cca gcc act cca tgg ccc ctg tca tct ttt gtc     410
Pro Val Ala Pro Ala Pro Ala Thr Pro Trp Pro Leu Ser Ser Phe Val
     80                  85                  90
```

```
cct tct caa aaa act tac cag ggc aac tat ggc ttc cac ctg ggc ttc      458
Pro Ser Gln Lys Thr Tyr Gln Gly Asn Tyr Gly Phe His Leu Gly Phe
 95             100                 105                 110 ctg cag tct ggg aca gcc aag tct gtt atg tgc acg tac tct cct ccc      506
Leu Gln Ser Gly Thr Ala Lys Ser Val Met Cys Thr Tyr Ser Pro Pro
            115                 120                 125 ctc aat aag cta ttc tgc cag ctg gcg aag acg tgc cct gtg cag ttg      554
Leu Asn Lys Leu Phe Cys Gln Leu Ala Lys Thr Cys Pro Val Gln Leu
                130                 135                 140 tgg gtc agc gcc aca cct cca gct ggg agc cgt gtc cgc gcc atg gcc      602
Trp Val Ser Ala Thr Pro Pro Ala Gly Ser Arg Val Arg Ala Met Ala
145                 150                 155 atc tac aag aag tca cag cac atg acg gag gtc gtg aga cgc tgc ccc      650
Ile Tyr Lys Lys Ser Gln His Met Thr Glu Val Val Arg Arg Cys Pro
        160                 165                 170 cac cat gag cgc tgc tcc gat ggt gat ggc ctg gct cct ccc cag cat      698
His His Glu Arg Cys Ser Asp Gly Asp Gly Leu Ala Pro Pro Gln His
175                 180                 185                 190 ctt atc cgg gtg gaa gga aat ttg tat ccc gag tat ctg gaa gac agg      746
Leu Ile Arg Val Glu Gly Asn Leu Tyr Pro Glu Tyr Leu Glu Asp Arg
                195                 200                 205 cag act ttt cgc cac agc gtg gtg gta cct tat gag cca ccc gag gcc      794
Gln Thr Phe Arg His Ser Val Val Val Pro Tyr Glu Pro Pro Glu Ala
            210                 215                 220 ggc tct gag tat acc acc atc cac tac aag tac atg tgt aat agc tcc      842
Gly Ser Glu Tyr Thr Thr Ile His Tyr Lys Tyr Met Cys Asn Ser Ser
        225                 230                 235 tgc atg ggg ggc atg aac cgc cga cct atc ctt acc atc atc aca ctg      890
Cys Met Gly Gly Met Asn Arg Arg Pro Ile Leu Thr Ile Ile Thr Leu
240                 245                 250 gaa gac tcc agt ggg aac ctt ctg gga cgg gac agc ttt gag gtt cgt      938
Glu Asp Ser Ser Gly Asn Leu Leu Gly Arg Asp Ser Phe Glu Val Arg
255                 260                 265                 270 gtt tgt gcc tgc cct ggg aga gac cgc cgt aca gaa gaa gaa aat ttc      986
Val Cys Ala Cys Pro Gly Arg Asp Arg Arg Thr Glu Glu Glu Asn Phe
                275                 280                 285 cgc aaa aag gaa gtc ctt tgc cct gaa ctg ccc cca ggg agc gca aag     1034
Arg Lys Lys Glu Val Leu Cys Pro Glu Leu Pro Pro Gly Ser Ala Lys
            290                 295                 300 aga gcg ctg ccc acc tgc aca agc gcc tct ccc ccg caa aag aaa aaa     1082
Arg Ala Leu Pro Thr Cys Thr Ser Ala Ser Pro Pro Gln Lys Lys Lys
        305                 310                 315 cca ctt gat gga gag tat ttc acc ctc aag atc cgc ggg cgt aaa cgc     1130
Pro Leu Asp Gly Glu Tyr Phe Thr Leu Lys Ile Arg Gly Arg Lys Arg
320                 325                 330 ttc gag atg ttc cgg gag ctg aat gag gcc tta gag tta aag gat gcc     1178
Phe Glu Met Phe Arg Glu Leu Asn Glu Ala Leu Glu Leu Lys Asp Ala
335                 340                 345                 350 cat gct aca gag gag tct gga gac agc agg gct cac tcc agc tac ctg     1226
His Ala Thr Glu Glu Ser Gly Asp Ser Arg Ala His Ser Ser Tyr Leu
                355                 360                 365 aag acc aag aag ggc cag tct act tcc cgc cat aaa aaa aca atg gtc     1274
Lys Thr Lys Lys Gly Gln Ser Thr Ser Arg His Lys Lys Thr Met Val
            370                 375                 380 aag aaa gtg ggg cct gac tca gac tga ctgcctctgc atcccgtccc           1321
Lys Lys Val Gly Pro Asp Ser Asp
                385                 390 catcaccagc ctcccctct ccttgctgtc ttatgacttc agggctgaga cacaatcctc    1381
ccggtccctt ctgctgcctt ttttaccttg tagctagggc tcagcccct ctctgagtag    1441
```

```
tggttcctgg cccaagttgg ggaataggtt gatagttgtc aggtctctgc tggcccagcg    1501
aaattctatc cagccagttg ttggaccctg cacctacaa tgaaatctca ccctaccca     1561 caccctgtaa gattctatct tgggccctca tagggtccat atcctccagg gcctactttc    1621
cttccattct gcaaagcctg tctgcattta tccaccccc accctgtctc cctctttttt     1681 tttttttac cccttttat atatcaattt cctatttac aataaaattt tgttatcact      1741 taaaaaaaa aaaaaaaaaa aaaaaaaaaa aaaaaaaaa a                         1782
```

<210> SEQ ID NO 2
<211> LENGTH: 390
<212> TYPE: PRT
<213> ORGANISM: Mus musculus

<400> SEQUENCE: 2

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asp Ile Leu Pro Ser Pro His Cys Met Asp Asp Leu Leu Leu Pro Gln
            35                  40                  45

Asp Val Glu Glu Phe Phe Glu Gly Pro Ser Glu Ala Leu Arg Val Ser
        50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
                100                 105                 110

Ser Gly Thr Ala Lys Ser Val Met Cys Thr Tyr Ser Pro Pro Leu Asn
            115                 120                 125

Lys Leu Phe Cys Gln Leu Ala Lys Thr Cys Pro Val Gln Leu Trp Val
        130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Lys Pro Leu
```

```
                305                 310                 315                 320
Asp Gly Glu Tyr Phe Thr Leu Lys Ile Arg Gly Arg Lys Arg Phe Glu
                    325                 330                 335

Met Phe Arg Glu Leu Asn Glu Ala Leu Glu Leu Lys Asp Ala His Ala
                340                 345                 350

Thr Glu Glu Ser Gly Asp Ser Arg Ala His Ser Ser Tyr Leu Lys Thr
            355                 360                 365

Lys Lys Gly Gln Ser Thr Ser Arg His Lys Lys Thr Met Val Lys Lys
        370                 375                 380

Val Gly Pro Asp Ser Asp
385                 390

<210> SEQ ID NO 3
<211> LENGTH: 2586
<212> TYPE: DNA
<213> ORGANISM: Homo sapiens
<220> FEATURE:
<221> NAME/KEY: CDS
<222> LOCATION: (198)..(1379)

<400> SEQUENCE: 3
gattggggtt tcccctccc atgtgctcaa gactggcgct aaaagttttg agcttctcaa         60
aagtctagag ccaccgtcca gggagcaggt agctgctggg ctccggggac actttgcgtt       120
cgggctggga gcgtgctttc cacgacggtg acacgcttcc ctggattggc agccagactg       180
ccttccgggt cactgcc atg gag gag ccg cag tca gat cct agc gtc gag          230
                    Met Glu Glu Pro Gln Ser Asp Pro Ser Val Glu
                     1               5                  10 ccc cct ctg agt cag gaa aca ttt tca gac cta tgg aaa cta ctt cct        278
Pro Pro Leu Ser Gln Glu Thr Phe Ser Asp Leu Trp Lys Leu Leu Pro
            15                  20                  25 gaa aac aac gtt ctg tcc ccc ttg ccg tcc caa gca atg gat gat ttg        326
Glu Asn Asn Val Leu Ser Pro Leu Pro Ser Gln Ala Met Asp Asp Leu
        30                  35                  40 atg ctg tcc ccg gac gat att gaa caa tgg ttc act gaa gac cca ggt        374
Met Leu Ser Pro Asp Asp Ile Glu Gln Trp Phe Thr Glu Asp Pro Gly
    45                  50                  55 cca gat gaa gct ccc aga atg cca gag gct gct ccc ccc gtg gcc cct        422
Pro Asp Glu Ala Pro Arg Met Pro Glu Ala Ala Pro Pro Val Ala Pro
60                  65                  70                  75 gca cca gca gct cct aca ccg gcg gcc cct gca cca gcc ccc tcc tgg        470
Ala Pro Ala Ala Pro Thr Pro Ala Ala Pro Ala Pro Ala Pro Ser Trp
                80                  85                  90 ccc ctg tca tct tct gtc cct tcc cag aaa acc tac cag ggc agc tac        518
Pro Leu Ser Ser Ser Val Pro Ser Gln Lys Thr Tyr Gln Gly Ser Tyr
            95                  100                 105 ggt ttc cgt ctg ggc ttc ttg cat tct ggg aca gcc aag tct gtg act        566
Gly Phe Arg Leu Gly Phe Leu His Ser Gly Thr Ala Lys Ser Val Thr
        110                 115                 120 tgc acg tac tcc cct gcc ctc aac aag atg ttt tgc caa ctg gcc aag        614
Cys Thr Tyr Ser Pro Ala Leu Asn Lys Met Phe Cys Gln Leu Ala Lys
    125                 130                 135 acc tgc cct gtg cag ctg tgg gtt gat tcc aca ccc ccg ccc ggc acc        662
Thr Cys Pro Val Gln Leu Trp Val Asp Ser Thr Pro Pro Pro Gly Thr
140                 145                 150                 155 cgc gtc cgc gcc atg gcc atc tac aag cag tca cag cac atg acg gag        710
Arg Val Arg Ala Met Ala Ile Tyr Lys Gln Ser Gln His Met Thr Glu
                160                 165                 170 gtt gtg agg cgc tgc ccc cac cat gag cgc tgc tca gat agc gat ggt        758
```

```
Val Val Arg Arg Cys Pro His His Glu Arg Cys Ser Asp Ser Asp Gly
                175                 180                 185 ctg gcc cct cct cag cat ctt atc cga gtg gaa gga aat ttg cgt gtg    806
Leu Ala Pro Pro Gln His Leu Ile Arg Val Glu Gly Asn Leu Arg Val
            190                 195                 200 gag tat ttg gat gac aga aac act ttt cga cat agt gtg gtg gtg ccc    854
Glu Tyr Leu Asp Asp Arg Asn Thr Phe Arg His Ser Val Val Val Pro
205                 210                 215 tat gag ccg cct gag gtt ggc tct gac tgt acc acc atc cac tac aac    902
Tyr Glu Pro Pro Glu Val Gly Ser Asp Cys Thr Thr Ile His Tyr Asn
220                 225                 230                 235 tac atg tgt aac agt tcc tgc atg ggc ggc atg aac cgg agg ccc atc    950
Tyr Met Cys Asn Ser Ser Cys Met Gly Gly Met Asn Arg Arg Pro Ile
                240                 245                 250 ctc acc atc atc aca ctg gaa gac tcc agt ggt aat cta ctg gga cgg    998
Leu Thr Ile Ile Thr Leu Glu Asp Ser Ser Gly Asn Leu Leu Gly Arg
            255                 260                 265 aac agc ttt gag gtg cgt gtt tgt gcc tgt cct ggg aga gac cgg cgc    1046
Asn Ser Phe Glu Val Arg Val Cys Ala Cys Pro Gly Arg Asp Arg Arg
        270                 275                 280 aca gag gaa gag aat ctc cgc aag aaa ggg gag cct cac cac gag ctg    1094
Thr Glu Glu Glu Asn Leu Arg Lys Lys Gly Glu Pro His His Glu Leu
285                 290                 295 ccc cca ggg agc act aag cga gca ctg ccc aac aac acc agc tcc tct    1142
Pro Pro Gly Ser Thr Lys Arg Ala Leu Pro Asn Asn Thr Ser Ser Ser
300                 305                 310                 315 ccc cag cca aag aag aaa cca ctg gat gga gaa tat ttc acc ctt cag    1190
Pro Gln Pro Lys Lys Lys Pro Leu Asp Gly Glu Tyr Phe Thr Leu Gln
                320                 325                 330 atc cgt ggg cgt gag cgc ttc gag atg ttc cga gag ctg aat gag gcc    1238
Ile Arg Gly Arg Glu Arg Phe Glu Met Phe Arg Glu Leu Asn Glu Ala
            335                 340                 345 ttg gaa ctc aag gat gcc cag gct ggg aag gag cca ggg ggg agc agg    1286
Leu Glu Leu Lys Asp Ala Gln Ala Gly Lys Glu Pro Gly Gly Ser Arg
        350                 355                 360 gct cac tcc agc cac ctg aag tcc aaa aag ggt cag tct acc tcc cgc    1334
Ala His Ser Ser His Leu Lys Ser Lys Lys Gly Gln Ser Thr Ser Arg
365                 370                 375 cat aaa aaa ctc atg ttc aag aca gaa ggg cct gac tca gac tga        1379
His Lys Lys Leu Met Phe Lys Thr Glu Gly Pro Asp Ser Asp
380                 385                 390 cattctccac ttcttgttcc ccactgacag cctcccaccc ccatctctcc ctcccctgcc  1439
attttgggtt ttgggtcttt gaacccttgc ttgcaatagg tgtgcgtcag aagcacccag  1499
gacttccatt tgctttgtcc cggggctcca ctgaacaagt tggcctgcac tggtgttttg  1559
ttgtggggag gaggatgggg agtaggacat accagcttag attttaaggt ttttactgtg  1619
agggatgttt gggagatgta agaaatgttc ttgcagttaa gggttagttt acaatcagcc  1679
acattctagg tagggcccca cttcaccgta ctaaccaggg aagctgtccc tcactgttga  1739
attttctcta acttcaaggc ccatatctgt gaaatgctgg catttgcacc tacctcacag  1799
agtgcattgt gagggttaat gaaataatgt acatctggcc ttgaaaccac cttttattac  1859
atggggtcta gaacttgacc cccttgaggg tgcttgttcc ctctccctgt tggtcggtgg  1919
gttggtagtt tctacagttg ggcagctggt taggtagagg gagttgtcaa gtctctgctg  1979
gcccagccaa accctgtctg acaacctctt ggtgaacctt agtacctaaa aggaaatctc  2039
accccatccc acaccctgga ggatttcatc tcttgtatat gatgatctgg atccaccaag  2099
```

-continued

```
acttgtttta tgctcagggt caatttcttt ttttcttttt tttttttttt ttctttttct    2159
ttgagactgg gtctcgcttt gttgcccagg ctggagtgga gtggcgtgat cttggcttac    2219
tgcagccttt gcctccccgg ctcgagcagt cctgcctcag cctccggagt agctgggacc    2279
acaggttcat gccaccatgg ccagccaact tttgcatgtt ttgtagagat ggggtctcac    2339
agtgttgccc aggctggtct caaactcctg ggctcaggcg atccacctgt ctcagcctcc    2399
cagagtgctg ggattacaat tgtgagccac cacgtccagc tggaagggtc aacatctttt    2459
acattctgca agcacatctg catttccacc ccacccttcc cctccttctc ccttttata     2519 tcccatttt  atatcgatct cttattttac aataaaactt tgctgccacc tgtgtgtctg    2579
agggtg                                                              2586
```

<210> SEQ ID NO 4
<211> LENGTH: 393
<212> TYPE: PRT
<213> ORGANISM: Homo sapiens

<400> SEQUENCE: 4

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285
```

```
Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 5
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 5
tttgactgga tgactgccat ggttcaagag accatggcag tcatccagtc tttttt        56

<210> SEQ ID NO 6
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 6
tttgatatcc tgccatcacc tcttcaagag agaggtgatg gcaggatatc tttttt        56

<210> SEQ ID NO 7
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 7
tttggcccaa gtgaagccct ccttcaagag aggagggctt cacttgggcc tttttt        56

<210> SEQ ID NO 8
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 8
tttgtgaagc cctccgagtg tcttcaagag agacactcgg agggcttcac tttttt        56

<210> SEQ ID NO 9
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 9
```
tttgccctcc gagtgtcagg agttcaagag actcctgaca ctcggagggc tttttt          56

<210> SEQ ID NO 10
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 10
tttgtctgtt atgtgcacgt acttcaagag agtacgtgca cataacagac tttttt          56

<210> SEQ ID NO 11
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 11
tttgtactct cctcccctca atttcaagag aattgagggg aggagagtac tttttt          56

<210> SEQ ID NO 12
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 12
tttgctattc tgccagctgg cgttcaagag acgccagctg gcagaatagc tttttt          56

<210> SEQ ID NO 13
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 13
tttgacgtgc cctgtgcagt tgttcaagag acaactgcac agggcacgtc tttttt          56

<210> SEQ ID NO 14
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 14
tttgaagtca cagcacatga cgttcaagag acgtcatgtg ctgtgacttc tttttt          56

<210> SEQ ID NO 15
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 15
tttgtcacag cacatgacgg agttcaagag actccgtcat gtgctgtgac tttttt          56

<210> SEQ ID NO 16
<211> LENGTH: 56
<212> TYPE: DNA

```
<213> ORGANISM: Artificial Sequence
<220> FEATURE:
<223> OTHER INFORMATION: Synthetic sequence - shRNA against p53

<400> SEQUENCE: 16
tttggaaatt tgtatcccga gtttcaagag aactcgggat acaaatttcc tttttt        56

<210> SEQ ID NO 17
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 17
tttgtacatg tgtaatagct ccttcaagag aggagctatt acacatgtac tttttt        56

<210> SEQ ID NO 18
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 18
tttgactcca gtgggaacct tcttcaagag agaaggttcc cactggagtc tttttt        56

<210> SEQ ID NO 19
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 19
tttgtccttt gccctgaact gcttcaagag agcagttcag ggcaaaggac tttttt        56

<210> SEQ ID NO 20
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 20
tttgatccgc gggcgtaaac gcttcaagag agcgtttacg cccgcggatc tttttt        56

<210> SEQ ID NO 21
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 21
tttgaccaag aagggccagt ctttcaagag aagactggcc cttcttggtc tttttt        56

<210> SEQ ID NO 22
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 22
tttgaaagtg gggcctgact cattcaagag atgagtcagg ccccactttc tttttt        56
```

<210> SEQ ID NO 23
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 23
tttgttgggg aataggttga tattcaagag atatcaacct attccccaac tttttt       56

<210> SEQ ID NO 24
<211> LENGTH: 56
<212> TYPE: DNA
<213> ORGANISM: Artificial Sequence
<220> FEATURE:
<223> OTHER INFORMATION: Synthetic sequence - shRNA against p53

<400> SEQUENCE: 24
tttgattcta tcttgggccc tcttcaagag agagggccca agatagaatc tttttt       56

<210> SEQ ID NO 25
<211> LENGTH: 59
<212> TYPE: DNA
<213> ORGANISM: Artificial Sequence
<220> FEATURE:
<223> OTHER INFORMATION: Synthetic sequence - shRNA against p53

<400> SEQUENCE: 25
tttgcautac aggtacgtgt gtagtgtgct gtcctacaca tgtacttgta gtgtttttt    59

<210> SEQ ID NO 26
<211> LENGTH: 59
<212> TYPE: DNA
<213> ORGANISM: Artificial Sequence
<220> FEATURE:
<223> OTHER INFORMATION: Synthetic sequence - shRNA against p53

<400> SEQUENCE: 26
tttgcagtut acttccgcc gtagtgtgct gtcctatggc gggaagtaga ctgtttttt    59

<210> SEQ ID NO 27
<211> LENGTH: 10
<212> TYPE: DNA
<213> ORGANISM: Artificial Sequence
<220> FEATURE:
<223> OTHER INFORMATION: Synthetic sequence - p53 responsive element

<400> SEQUENCE: 27 rrrgwwcyyy       10

<210> SEQ ID NO 28
<211> LENGTH: 48
<212> TYPE: DNA
<213> ORGANISM: Artificial Sequence
<220> FEATURE:
<223> OTHER INFORMATION: Synthetic sequence - shRNA against p53

<400> SEQUENCE: 28
gactccagtg gtaatctact gctcgagcag tagattacca ctggagtc       48

<210> SEQ ID NO 29
<211> LENGTH: 24
<212> TYPE: DNA
<213> ORGANISM: Artificial Sequence
<220> FEATURE:

<223> OTHER INFORMATION: Primer

<400> SEQUENCE: 29
gtaggcacct gtggggaaga aact                                                  24

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
tgagagctgt ctcctactat cgatt                                                 25

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
caccaggatg actgccatgg aggagtc                                               27

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
gtgtctcagc cctgaagtca taa                                                   23

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
tgtttgtgcc tgctctggga gagaccgc                                              28

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
gcggtctctc ccagagcagg cacaaaca                                              28

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
tgccctggga gaaaccgccg tacagaa                                               27

```
<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
ttctgtacgg cggtttctcc cagggca                                         27

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
tttgaaggcc cagctgaagc cctccga                                         27

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
tcggagggct tcagctgggc cttcaaa                                         27

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
cggatatcag cctcaagaga gcgctgcc                                        28

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
ggcagcgctc tcttgaggct gatatccg                                        28

<210> SEQ ID NO 41
<211> LENGTH: 2357
<212> TYPE: DNA
<213> ORGANISM: Homo sapiens
<220> FEATURE:
<221> NAME/KEY: CDS
<222> LOCATION: (279)..(1772)

<400> SEQUENCE: 41
cgagcttggc tgcttctggg gcctgtgtgg ccctgtgtgt cggaaagatg gagcaagaag      60
ccgagcccga ggggcggccg cgaccctct gaccgagatc ctgctgcttt cgcagccagg     120
agcaccgtcc ctcccggat tagtgcgtac gagcgcccag tgccctggcc cggagagtgg     180
aatgatcccc gaggccaggg gcgtcgtgct tccgcgcgcc ccgtgaagga aactggggag     240
tcttgaggga cccccgactc caagcgcgaa aacccggg atg gtg agg agc agg caa    296
```

```
                        Met Val Arg Ser Arg Gln
                        1               5
atg tgc aat acc aac atg tct gta cct act gat ggt gct gta acc acc      344
Met Cys Asn Thr Asn Met Ser Val Pro Thr Asp Gly Ala Val Thr Thr
         10                  15                  20 tca cag att cca gct tcg gaa caa gag acc ctg gtt aga cca aag cca      392
Ser Gln Ile Pro Ala Ser Glu Gln Glu Thr Leu Val Arg Pro Lys Pro
             25                  30                  35 ttg ctt ttg aag tta tta aag tct gtt ggt gca caa aaa gac act tat      440
Leu Leu Leu Lys Leu Leu Lys Ser Val Gly Ala Gln Lys Asp Thr Tyr
 40                  45                  50 act atg aaa gag gtt ctt ttt tat ctt ggc cag tat att atg act aaa      488
Thr Met Lys Glu Val Leu Phe Tyr Leu Gly Gln Tyr Ile Met Thr Lys
55                  60                  65                  70 cga tta tat gat gag aag caa caa cat att gta tat tgt tca aat gat      536
Arg Leu Tyr Asp Glu Lys Gln Gln His Ile Val Tyr Cys Ser Asn Asp
             75                  80                  85 ctt cta gga gat ttg ttt ggc gtg cca agc ttc tct gtg aaa gag cac      584
Leu Leu Gly Asp Leu Phe Gly Val Pro Ser Phe Ser Val Lys Glu His
         90                  95                 100 agg aaa ata tat acc atg atc tac agg aac ttg gta gta gtc aat cag      632
Arg Lys Ile Tyr Thr Met Ile Tyr Arg Asn Leu Val Val Val Asn Gln
            105                 110                 115 cag gaa tca tcg gac tca ggt aca tct gtg agt gag aac agg tgt cac      680
Gln Glu Ser Ser Asp Ser Gly Thr Ser Val Ser Glu Asn Arg Cys His
    120                 125                 130 ctt gaa ggt ggg agt gat caa aag gac ctt gta caa gag ctt cag gaa      728
Leu Glu Gly Gly Ser Asp Gln Lys Asp Leu Val Gln Glu Leu Gln Glu
135                 140                 145                 150 gag aaa cct tca tct tca cat ttg gtt tct aga cca tct acc tca tct      776
Glu Lys Pro Ser Ser Ser His Leu Val Ser Arg Pro Ser Thr Ser Ser
                155                 160                 165 aga agg aga gca att agt gag aca gaa gaa aat tca gat gaa tta tct      824
Arg Arg Arg Ala Ile Ser Glu Thr Glu Glu Asn Ser Asp Glu Leu Ser
            170                 175                 180 ggt gaa cga caa aga aaa cgc cac aaa tct gat agt att tcc ctt tcc      872
Gly Glu Arg Gln Arg Lys Arg His Lys Ser Asp Ser Ile Ser Leu Ser
        185                 190                 195 ttt gat gaa agc ctg gct ctg tgt gta ata agg gag ata tgt tgt gaa      920
Phe Asp Glu Ser Leu Ala Leu Cys Val Ile Arg Glu Ile Cys Cys Glu
    200                 205                 210 aga agc agt agc agt gaa tct aca ggg acg cca tcg aat ccg gat ctt      968
Arg Ser Ser Ser Ser Glu Ser Thr Gly Thr Pro Ser Asn Pro Asp Leu
215                 220                 225                 230 gat gct ggt gta agt gaa cat tca ggt gat tgg ttg gat cag gat tca      1016
Asp Ala Gly Val Ser Glu His Ser Gly Asp Trp Leu Asp Gln Asp Ser
                235                 240                 245 gtt tca gat cag ttt agt gta gaa ttt gaa gtt gaa tct ctc gac tca      1064
Val Ser Asp Gln Phe Ser Val Glu Phe Glu Val Glu Ser Leu Asp Ser
            250                 255                 260 gaa gat tat agc ctt agt gaa gaa gga caa gaa ctc tca gat gaa gat      1112
Glu Asp Tyr Ser Leu Ser Glu Glu Gly Gln Glu Leu Ser Asp Glu Asp
        265                 270                 275 gat gag gta tat caa gtt act gtg tat cag gca ggg gag agt gat aca      1160
Asp Glu Val Tyr Gln Val Thr Val Tyr Gln Ala Gly Glu Ser Asp Thr
    280                 285                 290 gat tca ttt gaa gaa gat cct gaa att tcc tta gct gac tat tgg aaa      1208
Asp Ser Phe Glu Glu Asp Pro Glu Ile Ser Leu Ala Asp Tyr Trp Lys
295                 300                 305                 310
```

```
tgc act tca tgc aat gaa atg aat ccc ccc ctt cca tca cat tgc aac     1256
Cys Thr Ser Cys Asn Glu Met Asn Pro Pro Leu Pro Ser His Cys Asn
            315                 320                 325 aga tgt tgg gcc ctt cgt gag aat tgg ctt cct gaa gat aaa ggg aaa     1304
Arg Cys Trp Ala Leu Arg Glu Asn Trp Leu Pro Glu Asp Lys Gly Lys
        330                 335                 340 gat aaa ggg gaa atc tct gag aaa gcc aaa ctg gaa aac tca aca caa     1352
Asp Lys Gly Glu Ile Ser Glu Lys Ala Lys Leu Glu Asn Ser Thr Gln
    345                 350                 355 gct gaa gag ggc ttt gat gtt cct gat tgt aaa aaa act ata gtg aat     1400
Ala Glu Glu Gly Phe Asp Val Pro Asp Cys Lys Lys Thr Ile Val Asn
360                 365                 370 gat tcc aga gag tca tgt gtt gag gaa aat gat gat aaa att aca caa     1448
Asp Ser Arg Glu Ser Cys Val Glu Glu Asn Asp Asp Lys Ile Thr Gln
375                 380                 385                 390 gct tca caa tca caa gaa agt gaa gac tat tct cag cca tca act tct     1496
Ala Ser Gln Ser Gln Glu Ser Glu Asp Tyr Ser Gln Pro Ser Thr Ser
            395                 400                 405 agt agc att att tat agc agc caa gaa gat gtg aaa gag ttt gaa agg     1544
Ser Ser Ile Ile Tyr Ser Ser Gln Glu Asp Val Lys Glu Phe Glu Arg
        410                 415                 420 gaa gaa acc caa gac aaa gaa gag agt gtg gaa tct agt ttg ccc ctt     1592
Glu Glu Thr Gln Asp Lys Glu Glu Ser Val Glu Ser Ser Leu Pro Leu
    425                 430                 435 aat gcc att gaa cct tgt gtg att tgt caa ggt cga cct aaa aat ggt     1640
Asn Ala Ile Glu Pro Cys Val Ile Cys Gln Gly Arg Pro Lys Asn Gly
440                 445                 450 tgc att gtc cat ggc aaa aca gga cat ctt atg gcc tgc ttt aca tgt     1688
Cys Ile Val His Gly Lys Thr Gly His Leu Met Ala Cys Phe Thr Cys
455                 460                 465                 470 gca aag aag cta aag aaa agg aat aag ccc tgc cca gta tgt aga caa     1736
Ala Lys Lys Leu Lys Lys Arg Asn Lys Pro Cys Pro Val Cys Arg Gln
            475                 480                 485 cca att caa atg att gtg cta act tat ttc ccc tag ttgacctgtc         1782
Pro Ile Gln Met Ile Val Leu Thr Tyr Phe Pro
        490                 495 tataagagaa ttatatattt ctaactatat aaccctagga atttagacaa cctgaaattt   1842
attcacatat atcaaagtga gaaaatgcct caattcacat agatttcttc tctttagtat   1902
aattgaccta ctttggtagt ggaatagtga atacttacta taatttgact tgaatatgta   1962
gctcatcctt tacaccaact cctaatttta aataattct actctgtctt aaatgagaag    2022
tacttggttt ttttttttct taaatatgta tatgacattt aaatgtaact tattattttt   2082
tttgagaccg agtcttgctc tgttacccag gctggagtgc agtggcgtga tcttggctca   2142
ctgcaagctc tgcctcccgg gttcgcacca ttctcctgcc tcagcctccc aattagcttg   2202
gcctacagtc atctgccacc acacctggct aattttttgt acttttagta gagacagggt   2262
ttcaccgtgt tagccaggat ggtctcgatc tcctgacctc gtgatccgcc cacctcggcc   2322
tcccaaagtg ctgggattac aggcatgagc caccg                             2357

<210> SEQ ID NO 42
<211> LENGTH: 497
<212> TYPE: PRT
<213> ORGANISM: Homo sapiens

<400> SEQUENCE: 42

Met Val Arg Ser Arg Gln Met Cys Asn Thr Asn Met Ser Val Pro Thr
1               5                   10                  15
```

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
            100                 105                 110

Leu Val Val Val Asn Gln Gln Glu Ser Ser Asp Ser Gly Thr Ser Val
        115                 120                 125

Ser Glu Asn Arg Cys His Leu Glu Gly Gly Ser Asp Gln Lys Asp Leu
    130                 135                 140

Val Gln Glu Leu Gln Glu Lys Pro Ser Ser Ser His Leu Val Ser
145                 150                 155                 160

Arg Pro Ser Thr Ser Ser Arg Arg Ala Ile Ser Glu Thr Glu Glu
            165                 170                 175

Asn Ser Asp Glu Leu Ser Gly Glu Arg Gln Arg Lys Arg His Lys Ser
        180                 185                 190

Asp Ser Ile Ser Leu Ser Phe Asp Glu Ser Leu Ala Leu Cys Val Ile
    195                 200                 205

Arg Glu Ile Cys Cys Glu Arg Ser Ser Ser Glu Ser Thr Gly Thr
210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
            245                 250                 255

Val Glu Ser Leu Asp Ser Glu Asp Tyr Ser Leu Ser Glu Glu Gly Gln
        260                 265                 270

Glu Leu Ser Asp Glu Asp Asp Glu Val Tyr Gln Val Thr Val Tyr Gln
    275                 280                 285

Ala Gly Glu Ser Asp Thr Asp Ser Phe Glu Glu Asp Pro Glu Ile Ser
290                 295                 300

Leu Ala Asp Tyr Trp Lys Cys Thr Ser Cys Asn Glu Met Asn Pro Pro
            305                 310                 315                 320

Leu Pro Ser His Cys Asn Arg Cys Trp Ala Leu Arg Glu Asn Trp Leu
        325                 330                 335

Pro Glu Asp Lys Gly Lys Asp Lys Gly Glu Ile Ser Glu Lys Ala Lys
    340                 345                 350

Leu Glu Asn Ser Thr Gln Ala Glu Glu Gly Phe Asp Val Pro Asp Cys
355                 360                 365

Lys Lys Thr Ile Val Asn Asp Ser Arg Glu Ser Cys Val Glu Glu Asn
    370                 375                 380

Asp Asp Lys Ile Thr Gln Ala Ser Gln Ser Gln Glu Ser Glu Asp Tyr
385                 390                 395                 400

Ser Gln Pro Ser Thr Ser Ser Ile Ile Tyr Ser Ser Gln Glu Asp
            405                 410                 415

Val Lys Glu Phe Glu Arg Glu Thr Gln Asp Lys Glu Glu Ser Val
        420                 425                 430

Glu Ser Ser Leu Pro Leu Asn Ala Ile Glu Pro Cys Val Ile Cys Gln

-continued

```
                435                 440                 445
Gly Arg Pro Lys Asn Gly Cys Ile Val His Gly Lys Thr Gly His Leu
            450                 455                 460
Met Ala Cys Phe Thr Cys Ala Lys Lys Leu Lys Arg Asn Lys Pro
465                 470                 475                 480
Cys Pro Val Cys Arg Gln Pro Ile Gln Met Ile Val Leu Thr Tyr Phe
                485                 490                 495
Pro

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
gacaggggga ggggaggagc tagg                                          24

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
cttccctcca accagttgcc ccaaac                                        26

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
gggaaatggg aggggtgcaa aagagg                                        26

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
ttgcgtgagt gtggatggga ttggtg                                        26

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
cagccccgat tcttccacca gtccc                                         25

<210> SEQ ID NO 48
<211> LENGTH: 25
<212> TYPE: DNA
<213> ORGANISM: Artificial Sequence
<220> FEATURE:
```

<223> OTHER INFORMATION: Primer

<400> SEQUENCE: 48
cggaagattc ccagtcgggt tcacc                                              25

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
tgggagcggt gaagatggaa gggcac                                             26

<210> SEQ ID NO 50
<211> LENGTH: 26
<212> TYPE: DNA
<213> ORGANISM: Artificial Sequence
<220> FEATURE:
<223> OTHER INFORMATION: Primer

<400> SEQUENCE: 50
tcatgccagc gcccacgtac gacgac                                             26

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
cgctttcatg gtgtgggcta aggacg                                             26

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
tagttggggt ggtcctgcat gtgctg                                             26

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
cgagaggacc ccgtggatgc agag                                               24

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
ggcggccatc ttcagcttct ccag                                               24

```
<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
acccattatc cagatgtgtt tgcccgag                                          28

<210> SEQ ID NO 56
<211> LENGTH: 26
<212> TYPE: DNA
<213> ORGANISM: Artificial Sequence
<220> FEATURE:
<223> OTHER INFORMATION: Primer

<400> SEQUENCE: 56
atggtgaagc tgggcatagg cggcag                                            26

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
caggtggcgg acgtgtgaaa attgagagtg                                        30

<210> SEQ ID NO 58
<211> LENGTH: 26
<212> TYPE: DNA
<213> ORGANISM: Artificial Sequence
<220> FEATURE:
<223> OTHER INFORMATION: Primer

<400> SEQUENCE: 58
cacgctggat ctgcctgggg actgtg                                            26

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
attcttcgtt gtcaagccgc caaagtggag                                        30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
agttgtttgc tgcggagttg tcatctcgtc                                        30
```